US009434951B2

(12) United States Patent
Czech et al.

(10) Patent No.: US 9,434,951 B2
(45) Date of Patent: Sep. 6, 2016

(54) COMPOSITIONS AND METHODS FOR DECREASING LEUKOCYTE EXTRAVASATION AND VESSEL FLUID LEAKAGE

(71) Applicant: University of Massachusetts, Boston, MA (US)

(72) Inventors: Michael P. Czech, Westborough, MA (US); Rachel Roth Flach, Auburn, MA (US)

(73) Assignee: University of Massachusetts, Boston, MA (US)

( * ) Notice: Subject to any disclaimer, the term of this patent is extended or adjusted under 35 U.S.C. 154(b) by 0 days.

(21) Appl. No.: 14/401,629

(22) PCT Filed: May 21, 2013

(86) PCT No.: PCT/US2013/042065
§ 371 (c)(1),
(2) Date: Nov. 17, 2014

(87) PCT Pub. No.: WO2013/177194
PCT Pub. Date: Nov. 28, 2013

(65) Prior Publication Data
US 2015/0111947 A1    Apr. 23, 2015

Related U.S. Application Data

(60) Provisional application No. 61/650,113, filed on May 22, 2012.

(51) Int. Cl.
| A61K 48/00 | (2006.01) |
| C12N 15/113 | (2010.01) |
| A61K 31/713 | (2006.01) |
| A61K 45/06 | (2006.01) |
| A61K 9/00 | (2006.01) |

(52) U.S. Cl.
CPC ......... *C12N 15/1137* (2013.01); *A61K 31/713* (2013.01); *A61K 45/06* (2013.01); *A61K 9/0019* (2013.01); *C12N 2310/11* (2013.01); *C12N 2310/12* (2013.01); *C12N 2310/14* (2013.01); *C12N 2320/31* (2013.01); *C12Y 207/11001* (2013.01)

(58) Field of Classification Search
None
See application file for complete search history.

(56) References Cited

U.S. PATENT DOCUMENTS

| 2006/0111299 A1* | 5/2006 | Kisilevsky ............... C07K 7/08 514/1.9 |
| 2009/0023676 A1* | 1/2009 | McSwiggen ....... C12N 15/8218 514/44 R |
| 2009/0221676 A1 | 9/2009 | Czech |
| 2012/0059046 A1 | 3/2012 | Woolf |

OTHER PUBLICATIONS

Staels et al. (TRENDS in Mol. Med. vol. 8, Sep. 2002: 422-430).*
Notification Concerning Transmittal of International Preliminary Report on Patentability (Chapter I of the Patent Cooperation Treaty), International Application No. PCT/US2013/042065, mailed on Dec. 4, 2014, 9 pages.
Yao et al., "A Novel Human STE20-related Protein Kinase, HGK, That Specifically Activates the c-Jun N-terminal Kinase Signaling Pathway", J. Biol. Chem., vol. 274:2118-2125 (1999).
Xue et al., "Mesodermal patterning defect in mice lacking the Ste20 NCK interacting kinase (NIK)", Development, vol. 128:1559-1572 (2001).
Flach et al., "A Novel Role for Ste-20 Like Kinase MAP4K4 in Endothelial Cell Activation", The Metabolism of Lipids: Implications in Human Diseases, 34th Steenbock Symposium, University of Wisconsin, Madison USA (May 22-May 25, 2011).
Flack et al., "Beta adrenergic stimulation of adipose tissue activates adipose resident endothelium", Keystone Symposia meeting on Genetic and Molecular Basis of Obesity and Body Weight Regulation, Santa Fe Community Convention Center (Jan. 29-Feb. 3, 2012).
Aouadi, M. et al., "Orally delivered siRNA targeting macrophage Map4k4 suppresses systemic inflammation", Nature, Apr. 30, 2009, vol. 458 (7242), pp. 1180-1184, 16 pages author manuscript.
Bouzakri, K. et al., "MAP4K4 gene silencing in human skeletal muscle prevents tumor necrosis factor-a-induced insulin resistance". The Journal of Biological Chemistry, 2007, vol. 282, No. 11, pp. 7783-7789.
Austin, R. L et al., "siRNA-mediated reduction of inhibitor of nuclear factor-Kfi kinase prevents tumor necrosis factor-a-induced insulin resistance in human skeletal muscle", Diabetes, Aug. 2008, vol. 57, pp. 2066-2073.
Notification of Transmittal of the International search Report and the Written Opinion of the International Searching Authority, or the Declaration for PCT/US2013/042065 mailed on Aug. 28, 2013, 13 pages.
Eeckhoute et al., "Coordinated Regulation of PPARγ Expression and Activity through Control of Chromatin Structure in Adipogenesis and Obesity," *PPAR Research*, vol. 2012, 9 pp.

(Continued)

*Primary Examiner* — Kimberly Chong
(74) *Attorney, Agent, or Firm* — Fish & Richardson P.C.

(57) ABSTRACT

Provided herein are methods of decreasing leukocyte extravasation from a lymph or blood vessel into a tissue in a mammal, methods of decreasing fluid leakage from a lymph or blood vessel in a mammal in need thereof, methods of decreasing formation of atherosclerotic plaques in a mammal in need thereof, and methods of treating atherosclerosis in a mammal that include administering to the mammal an oligonucleotide that decreases Mitogen-activated protein kinase kinase kinase kinase 4 (Map4k4) mRNA expression in an endothelial cell. Also provided are methods of identifying a candidate agent useful for decreasing leukocyte extravasation or decreasing fluid leakage from a lymph or blood vessel in a mammal, and compositions containing an oligonucleotide that decreases Map4k4 mRNA expression in an endothelial cell and additional therapeutic agents.

17 Claims, 13 Drawing Sheets

(56) References Cited

OTHER PUBLICATIONS

Ehrlich et al., "ICF, an immunodeficiency syndrome: DNA methyltransferase 3B involvement, chromosome anomalies, and gene dysregulation," *Autoimmunity* 41(4):253-271 (2008).

Kim et al., "Regulation of Peroxisome Proliferator—Activated Receptor-γ Activity by Mammalian Target of Rapamycin and Amino Acids in Adipogenesis," *Diabetes* 53:2748-2756 (2004).

Liu et al., "ShRNA-Targeted MAP4K4 Inhibits Hepatocellular Carcinoma Growth," *Clin. Cancer Res.* 17:710-720, 2010.

Miled et al., "A Genomic Map of p53 Binding Sites Identifies Novel p53 Targets involved in an Apoptotic Network," *Cancer Res.* 65:5096-5104, 2005.

Puri et al., "RNAi screens reveal novel metabolic regulators: RIP140, MAP4k4 and the lipid droplet associated fat specific protein (FSP) 27," *Acta Physiol.* (Oxf.), 192:103-115, 2008.

Tang et al., "An RNA interference-based screen identifies MAP4K4/NIK as a negative regulator of PPAR, adipogenesis, and insuling-responsive hexose transport," *Proc. Natl. Acad. Sci. U.S.A.* 103:2087-2092, 2006.

Zhang et al., "Identification of Direct Serum-response Factor Gene Targets during Me2SO-induced P19 Cardiac Cell Differentiation," *J. Biol. Chem.* 280:19115-19126, 2005.

* cited by examiner

COMPOSITIONS AND METHODS FOR DECREASING LEUKOCYTE EXTRAVASATION AND VESSEL FLUID LEAKAGE

CROSS-REFERENCE TO RELATED APPLICATIONS

This application is a national stage application under 35 U.S.C. §371 of International Patent Application No. PCT/US2013/042065, filed on May 21, 2013, which claims priority to U.S. Provisional Patent Application No. 61/650,113, filed May 22, 2012 each of these applications are hereby incorporated herein by reference in their entirety.

TECHNICAL FIELD

This invention relates to the field of molecular biology and medicine.

BACKGROUND

Endothelial cells line blood vessels and lymph vessels, and remain in a quiescent state until inflammatory cues in underlying tissues cause them to become activated. Endothelial cell activation consists of changes in morphology, as well as gene expression. Activated endothelial cells promote vascular/lymphatic vessel fluid leakage and the extravasation of leukocytes from the lumen of blood and lymph vessels to adjoining tissues. The extravasation of leukocytes from the lumen of blood and lymph vessels into an adjoining tissue is induced by the expression of leukocyte adhesion molecules in activated endothelial cells that line lymph and blood vessels. The expression of leukocyte adhesion molecules in these activated endothelial cells promotes the rolling of leukocytes in the blood or lymph vessel, firm adhesion of leukocytes within the blood or lymph vessel, and finally, extravasation of leukocytes out of the blood or lymph vessels and into the adjoining tissue.

Increased extravasation of leukocytes and blood/lymph vessel fluid leakage plays a role in inflammation, inflammatory disorders, and vessel (blood and lymph vessel) fluid leakage disorders. For example, increases in endothelial cell adhesion molecule expression and leukocyte extravasation are associated with several inflammatory disorders, including cardiovascular disease and atherosclerosis. Conversely, loss of endothelial cell adhesion molecules can cause one to be immune-compromised, thus illustrating the important role for endothelial cells in the promotion of inflammation, and the maintenance of vascular and lymphatic homeostasis.

Models of inflammation in murine animal models are well documented. Mice lacking the leukocyte adhesion molecules intercellular adhesion molecule-1 (ICAM-1), vascular cell adhesion molecule-1 (VCAM-1), and E- or P-selectin (or combinations thereof) display reduced levels of acute inflammation. Furthermore, mice lacking apolipoprotein E (ApoE) or low-density lipoprotein (LDL) receptors, which are prone to atherosclerosis, display reduced atherosclerosis when these leukocyte adhesion molecules are absent.

SUMMARY

The inventions described herein are based, at least in part, on the discovery that oligonucleotides that decrease the expression of Mitogen-activated protein kinase kinase kinase kinase 4 (Map4k4) mRNA in an endothelial cell reduce the induction of leukocyte adhesion molecules in endothelial cells and also reduce endothelial cell monolayer permeability. In view of these discoveries, provided herein are methods of decreasing leukocyte extravasation from a lymph or blood vessel into a tissue in a mammal that include or consist of administering to the mammal an oligonucleotide that decreases Map4k4 mRNA expression in an endothelial cell. Also provided are methods of decreasing fluid leakage from a lymph or blood vessel in a mammal, methods of decreasing the formation of atherosclerotic plaques in a blood vessel in a mammal in need thereof, and methods of treating a mammal having atherosclerosis that include or consist of administering to the mammal an oligonucleotide that decreases Map4k4 mRNA expression in an endothelial cell, and screening methods for identifying a candidate agent useful for decreasing leukocyte extravasation or decreasing fluid leakage from a lymph or blood vessel in a mammal. Compositions containing an oligonucleotide that decreases Map4k4 mRNA expression in an endothelial cell and one or more cholesterol-improving agents are also provided.

Provided herein are methods of decreasing leukocyte extravasation from a lymph or blood vessel into a tissue in a mammal in need thereof that include or consist of administering to the mammal an oligonucleotide selected from the group consisting of an inhibitory RNA, an antisense oligonucleotide, and a ribozyme that decreases Map4k4 mRNA expression in an endothelial cell, in an amount sufficient to decrease expression of leukocyte adhesion molecules in endothelial cells lining blood or lymph vessels, thereby decreasing extravasation of leukocytes from the lymph or blood vessel into a tissue in a mammal. In some embodiments, the mammal has been diagnosed as having acute inflammation, chronic inflammation, atherosclerosis, or an autoimmune disease. In some embodiments, the administration of the oligonucleotide results in treatment of acute inflammation, chronic inflammation, atherosclerosis, or the autoimmune disease. In some embodiments, the oligonucleotide is administered by intravenous or intraarterial administration. In some embodiments, the leukocyte is a monocyte, a T-lymphocyte, an eosinophil, a basophil, a neutrophil, or a B-lymphocyte.

Also provided are methods of decreasing fluid leakage from a lymph or blood vessel in a mammal in need thereof that include or consist of administering to the mammal an oligonucleotide selected from the group consisting of an inhibitory RNA, an antisense oligonucleotide, and a ribozyme that decreases Map4k4 mRNA expression in an endothelial cell, where the oligonucleotide is administered in an amount sufficient to decrease fluid leakage from a lymph or blood vessel in the mammal. In some embodiments, the mammal has been diagnosed as having acute inflammation, chronic inflammation, lymphedema, edema, or an autoimmune disease. In some embodiments, the administration results in treatment of acute inflammation, chronic inflammation, lymphedema, edema, or the autoimmune disease. In some embodiments, the oligonucleotide is administered by intravenous or intraarterial administration.

Also provided herein are methods of reducing formation of atherosclerotic plaques in a blood vessel in a mammal in need thereof that include or consist of administering to the mammal an oligonucleotide selected from the group consisting of an inhibitory RNA, an antisense oligonucleotide, and a ribozyme that decreases Map4k4 mRNA expression in an endothelial cell, in an amount sufficient to decrease expression of leukocyte adhesion molecules in endothelial cells lining blood or lymph vessels, thereby reducing formation of atherosclerotic plaques in a blood vessel in a mammal. In some embodiments, the mammal has been diagnosed as having atherosclerosis. In some embodiments, the administration of the oligonucleotide results in treatment of atherosclerosis. In some embodiments, the oligonucleotide is administered by intravenous or intraarterial administration.

Also provided herein are methods of treating atherosclerosis in a mammal that include or consist of administering to the mammal an oligonucleotide selected from the group consisting of an inhibitory RNA, an antisense oligonucleotide, and a ribozyme that decreases Map4k4 mRNA expression in an endothelial cell, in an amount sufficient to treat atherosclerosis in a mammal. In some embodiments, the mammal has been diagnosed as having atherosclerosis. In some embodiments, the oligonucleotide is administered by intravenous or intraarterial administration.

In some embodiments of any of the methods described herein, the mammal is a human. In some embodiments of any of the methods described herein, the oligonucleotide is an inhibitory RNA (e.g., a small inhibitory RNA). In some embodiments of any of the above methods described herein, the oligonucleotide is an antisense oligonucleotide. In some embodiments of any of the methods described herein, the oligonucleotide is a ribozyme. In some embodiments of any of the methods described herein, the oligonucleotide is administered in a liposome or a nanoparticle.

Also provided are methods of identifying a candidate agent useful for decreasing leukocyte extravasation from a lymph or blood vessel into a tissue in a mammal or decreasing fluid leakage from a lymph or blood vessel in a mammal. These methods include or consist of providing a mammalian endothelial cell, contacting the mammalian endothelial cell with a candidate agent, determining a test level of Map4k4 expression in the mammalian endothelial cell, comparing the test level of Map4k4 expression in the mammalian endothelial cell to a reference level of Map4k4 expression in a control mammalian endothelial cell untreated with the candidate agent, and identifying a candidate agent that results in a test level of Map4k4 expression that is lower than the reference level of Map4k4 expression as being useful for decreasing leukocyte extravasation or fluid leakage from a lymph or blood vessel into a tissue in a mammal.

In some embodiments, the mammalian endothelial cell is in vitro. In some embodiments, the mammalian cell is in a mammal. In some embodiments, Map4k4 expression is Map4k4 protein expression. In some embodiments, Map4k4 expression is Map4k4 mRNA expression.

Also provided are compositions that include or consist of an oligonucleotide selected from the group of an inhibitory RNA, an antisense oligonucleotide, and a ribozyme that decreases Map4k4 mRNA expression in an endothelial cell; and one or more cholesterol-improving therapeutic agents (e.g., a statin, gemfibrozil, or fenofibrate). In some embodiments, the composition is formulated for intraarterial or intravenous administration. In some embodiments, the composition is formulated in a liposome or a nanoparticle.

Also provided herein are methods of using an oligonucleotide that decreases the expression of Map4k4 mRNA in an endothelial cell in the manufacture of a medicament for treating inflammation, or treating an inflammatory disorder, e.g., atherosclerosis or psoriasis, or a vessel fluid leakage disorder in a mammal.

Also provided herein are oligonucleotides that decrease the expression of Map4k4 mRNA in an endothelial cell for use in treating inflammation, or treating an inflammatory disorder or a vessel fluid leakage disorder in a mammal.

Also provided herein are methods of using an oligonucleotide that decreases the expression of Map4k4 mRNA in an endothelial cell in the manufacture of a medicament for decreasing leukocyte extravasation from a lymph or blood vessel into a tissue in a mammal (e.g., a human) in need thereof.

Also provided herein are oligonucleotides that decrease the expression of Map4k4 mRNA in an endothelial cell for use in decreasing leukocyte extravasation from a lymph or blood vessel into a tissue in a mammal (e.g., a human) in need thereof.

Also provided herein are methods of using an oligonucleotide that decreases the expression of Map4k4 mRNA in an endothelial cell in the manufacture of a medicament for reducing the formation of atherosclerotic plaques in a blood vessel in a mammal in need thereof and/or treating atherosclerosis in a mammal (e.g., a human).

Also provided herein are oligonucleotides that decrease the expression of Map4k4 mRNA in an endothelial cell for use in reducing the formation of atherosclerotic plaques in a blood vessel in a mammal in need thereof and/or treating atherosclerosis in a mammal (e.g., a human).

Also provided herein are methods of using an oligonucleotide that decreases the expression of Map4k4 mRNA in an endothelial cell in the manufacture of a medicament for decreasing fluid leakage from a lymph or blood vessel in a mammal (e.g., a human) in need thereof.

Also provided herein are oligonucleotides that decrease the expression of Map4k4 mRNA in an endothelial cell for use in decreasing fluid leakage from a lymph or blood vessel in a mammal (e.g., a human) in need thereof.

By the term "extravasation" is meant the migration of a mammalian leukocyte from the interior (lumen) of a blood or lymph vessel into a tissue surrounding the blood or lymph vessel in a mammal. In some embodiments, the mammalian leukocyte that migrates from the interior of a blood or lymph vessel into a surrounding tissue is a monocyte, a T-lymphocyte, an eosinophil, a basophil, a neutrophil, or a B-lymphocyte.

By the phrase "decrease expression" is meant a reduction in the level of a specific protein or a reduction in the level of an mRNA encoding a specific protein in a mammalian cell (e.g., a mammalian endothelial cell) upon contacting the endothelial cell with an agent (e.g., an oligonucleotide that decreases Map4k4 mRNA expression in an endothelial cell) as compared to a control endothelial cell not contacted with the agent. In some embodiments, a level of a Map4k4 protein or an mRNA encoding a Map4k4 protein (a Map4k4 mRNA) is reduced in a mammalian endothelial cell. In some embodiments, a level of one of more leukocyte adhesion molecules or one or more mRNAs encoding a leukocyte adhesion molecule is reduced in a mammalian endothelial cell.

By the term "leukocyte adhesion molecule" is meant a protein (e.g., a glycoprotein) expressed on the surface of a mammalian endothelial cell lining a blood or lymph vessel that is specifically recognized and bound by a protein present (expressed) on the surface of a leukocyte (e.g., any of the leukocytes described herein). Non-limiting examples of leukocyte adhesion molecules include ICAM-1, VCAM-1, and E-selectin.

By the term "fluid leakage" is meant the escape of blood or plasma from a mammalian blood vessel or the escape of lymph from a mammalian lymph vessel.

By the term "Map4k4 protein" or "Mitogen-activated protein kinase kinase kinase kinase 4 protein" is meant an endogenous mammalian Map4k4 protein. In some embodiments, the Map4k4 protein is a human Map4k4 protein (e.g., SEQ ID NO: 1, 3, 5, 7, or 9). Additional examples of Map4k4 protein are described herein.

By the term "Map4k4 mRNA" or "Mitogen-activated protein kinase kinase kinase kinase 4 mRNA" is meant an endogenous messenger RNA that encodes a mammalian Map4k4 protein. In some embodiments, the Map4k4 mRNA is a human Map4k4 mRNA (e.g., SEQ ID NO: 2, 4, 6, 8, or 10).

By the term "cholesterol-improving therapeutic agent" is meant a pharmaceutical agent that mediates a decrease in the level of low density lipoprotein (LDL), a decrease in the level of total cholesterol (high density lipoprotein (HDL)+LDL+other lipid components), and/or an increase in the level of HDL in a mammal. In some embodiments, the cholesterol-improving therapeutic agent is a statin, gemfibrozil, or fenofibrate.

The term "reducing the formation of atherosclerotic plaques" means causing a decrease in the development of new atherosclerotic plaques over time and/or causing a decrease in the rate of expansion of one or more pre-existing atherosclerotic plaques in a mammal (e.g., a human) following the administration of a treatment as compared to a control mammal (e.g., a human) that is not administered the same treatment or receives a placebo. For example, the mammal that receives the treatment can have the same disease (e.g., atherosclerosis) as the control mammal. For example, the mammal that receives the treatment can be a human diagnosed with atherosclerosis, and the control mammal (e.g., human) can also be diagnosed with atherosclerosis. In other examples, the mammal (e.g., human) that receives that treatment can be identified as having an increased risk of developing atherosclerosis, and the control mammal (e.g., human) can also be identified as having an increased risk of developing atherosclerosis.

Other definitions appear in context throughout this disclosure. Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DETAILED DESCRIPTION

Figure 1:
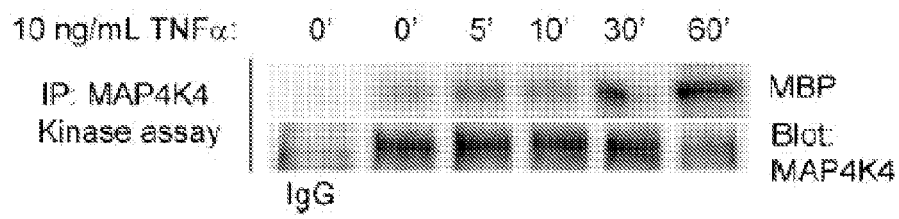
FIG. 1 is an image of a section of a Western blot of proteins immunoprecipitated from human umbilical vein endothelial cells (HUVECs) using an antibody against human Map4k4 protein (bottom row), and a section of a polyacrylamide gel showing the phosphorylation ($P^{32}$) of myelin basic protein (MBP) following incubation of MBP substrate and $P^{32}$-ATP with human Map4k4 immunoprecipitated from HUVECs (bottom row). In each experiment, the HUVECs were either untreated or treated with 10 ng/mL TNFα for up to 60 minutes before lysis and immunoprecipitation with the anti-human Map4k4 antibody.

The inventions described herein are based, at least in part, on the discovery that decreasing Map4k4 expression in endothelial cells results in a decrease in the expression of several different leukocyte adhesion molecules, and results in a decrease in the permeability of endothelial cell monolayers. Thus, provided herein are methods of decreasing leukocyte extravasation from a lymph or blood vessel into a tissue in a mammal and methods of decreasing fluid leakage from a lymph or blood vessel in a mammal that include or consist of administering an oligonucleotide that decreases the level of Map4k4 mRNA in an endothelial cell.

Also provided are methods of identifying candidate agents that are useful for decreasing leukocyte extravasation from a lymph or blood vessel in a mammal or decreasing fluid leakage from a lymph or blood vessel in a mammal. The screening methods include, inter alia, contacting an endothelial cell with a candidate agent and determining the level of Map4k4 expression in the endothelial cell.

Also provided are compositions that contain or consist of an oligonucleotide that decreases the expression of Map4k4 mRNA in an endothelial cell and a cholesterol-improving therapeutic agent. Various, non-limiting features of each aspect of the invention are described below.

Map4k4

Mitogen-activated protein kinase kinase kinase kinase 4 (Map4k4; also known as NCK-interacting Kinase, or NIK) is a serine/threonine kinase that regulates diverse signaling pathways and is essential for mammalian development (Xue et al., *Development*, 128(9):1559-1572, 2001). The N-terminus of the human Map4k4 polypeptide has a catalytic kinase domain with 11 kinase subdomains (Yao et al., *J. Biol. Chem.*, 274: 2118-2125, 1999).

Non-limiting examples of Map4k4 proteins are endogenous Map4k4 proteins, e.g., an endogenous human Map4k4 protein (e.g., a Map4k4 protein containing the sequence of SEQ ID NO: 1, 3, 5, 7, or 9) and an endogenous dog Map4k4 protein (e.g., SEQ ID NO: 11). In some embodiments, an endogenous form of Map4k4 protein contains a sequence that is at least 80% identical (e.g., at least 85%, 90%, 91%, 92%, 93%, 94%, 95%, 96%, 97%, 98%, 99%, or 100% identical) to SEQ ID NO: 1, 3, 5, 7, 9, or 11. A number of additional endogenous mammalian forms of Map4k4 protein are known in the art.

Examples of Map4k4 proteins include for example, the following proteins: human Map4k4 protein isoform 1 (SEQ ID NO: 1), human Map4k4 protein isoform 2 (SEQ ID NO: 3), human Map4k4 protein isoform 3 (SEQ ID NO: 5), human Map4k4 protein isoform 4 (SEQ ID NO: 7), human Map4k4 protein isoform 5 (SEQ ID NO: 9), and dog Map4k4 protein (SEQ ID NO: 11).

Non-limiting examples of Map4k4 cDNA that encode human and dog Map4k4 protein are: human Map4k4 isoform 1 cDNA (SEQ ID NO: 2), human Map4k4 isoform 2 cDNA (SEQ ID NO: 4), human Map4k4 isoform 3 cDNA (SEQ ID NO: 6), human Map4k4 isoform 4 cDNA (SEQ ID NO: 8), human Map4k4 isoform 5 cDNA (SEQ ID NO: 10), and dog Map4k4 cDNA (SEQ ID NO: 12). In some embodiments, the Map4k4 mRNA contains a sequence that is at least 80% identical (e.g., at least 85%, 90%, 91%, 92%, 93%, 94%, 95%, 96%, 97%, 98%, 99%, or 100% identical) to SEQ ID NO: 2, 4, 6, 8, 10, or 12. Additional examples of Map4k4 mRNA that encode other endogenous forms of mammalian Map4k4 protein are known in the art.

Methods of Decreasing Leukocyte Extravasation and Decreasing Vessel Fluid Leakage Also provided are methods of decreasing leukocyte extravasation from a lymph or blood vessel in a mammal in need thereof, that include or consist of administering to the mammal an oligonucleotide that decreases Map4k4 mRNA expression in an endothelial cell, in an amount sufficient to decrease expression of leukocyte adhesion molecules in endothelial cells lining blood or lymph vessels; thereby decreasing extravasation of leukocytes from the lymph or blood vessel into a tissue in a mammal.

In addition, methods of decreasing fluid leakage from a lymph or blood vessel in a mammal are provided that include or consist of administering to the mammal an oligonucleotide that decreases Map4k4 mRNA expression in an endothelial cell, where the oligonucleotide is administered in an amount sufficient to decrease fluid leakage from a lymph or blood vessel in the mammal.

In some embodiments of all the methods described herein, the oligonucleotide that decreases the expression of Map4k4 mRNA in an endothelial cell is "synthetic," i.e., is synthesized in vitro. In some embodiments of all the methods described herein, the oligonucleotide that decreases the expression of Map4k4 mRNA in an endothelial cell includes or consists of one or more (e.g., at least 2, 3, 4, 5, 6, 7, 8, 9, 10, 11, 12, 13, 14, 15, 16, 17, 18, 19, 20, 21, 22, 23, 24, 25, or 26) modified nucleotides (e.g., one or more different types of modified nucleotides known in the art or described herein).

In some embodiments, the oligonucleotide that decreases the expression of Map4k4 mRNA in an endothelial cell is a small inhibitory or interfering RNA (e.g., siRNA), an antisense oligonucleotide, or a ribozyme (e.g., any of the oligonucleotides that decrease the expression of Map4k4 mRNA in an endothelial cell described herein).

In some embodiments, the mammal (e.g., human) has been previously diagnosed or is suspected of having inflammation (e.g., acute inflammation or chronic inflammation) or an inflammatory disorder (e.g., atherosclerosis or an autoimmune disease). Non-limiting examples of autoimmune diseases include acute disseminated encephalomyelitis, acute necrotizing hemorrhagic leukoencephalitis, Addison's disease, alopecia areata, amyloidosis, ankylosing spondylitis, nephritis, autoimmune angioedema, autoimmune hepatitis, autoimmune inner ear disease, autoimmune myocarditis, autoimmune pancreatitis, autoimmune retinopathy, autoimmune thrombocytopenic purpura, autoimmune thyroid disease, autoimmune urticarial, axonal and neuronal neuropathies, Behçet's disease, Bullous pemphigoid, cardiomyopathy, Celiac disease, Chagas disease, chronic inflammatory demyelinating polyneuropathy, chronic recurrent multifocal osteomyelitis, cicatricial pemphigoid/benign mucosal pemphigoid, Crohn's disease, demyelinating neuropathies, dermatomyositis, endometriosis, eosinophilic fasciitis, erythema nodosum, experimental allergic encephalomyelitis, fibrosing alveolitis, giant cell arteritis (temporal arteritis), glomerulonephritis, Goodpasture's syndrome, Graves' disease, Guillain-Barre syndrome, Hashimoto's encephalitis, Hashimoto's thyroiditis, IgA nephropathy, IgG4-related sclerosing disease, inclusion body myositis, interstitial cystitis, juvenile arthritis, leukocytoclastic vasculitis, ligneous conjunctivitis, mixed connective tissue disease, multiple sclerosis, myositis, ocular cicatricial pemphigoid, optic neuritis, palindromic rheumatism, *pemphigus*, peripheral neuropathy, perivenous encephalomyelitis, type I, II, and III autoimmune polyglandular syndromes, polymyalgia rheumatic, polymyositis, postmyocardial infarction syndrome, postpericardiotomy syndrome, progesterone dermatitis, primary biliary cirrhosis, primary sclerosing cholangitis, psoriasis, psoriatic arthritis, idiopathic pulmonary fibrosis, pyoderma gangrenosum, pure red cell aplasia, rheumatoid arthritis, sarcoidosis, scleritis, *scleroderma*, sperm and testicular autoimmunity, Takayasu's arteritis, temporal arteritis/Giant cell arteritis, thrombocytopenic purpura (TTP), transverse myelitis, ulcerative colitis, undifferentiated connective tissue disease (UCTD), uveitis, vasculitis, vesiculobullous dermatosis, vitiligo, and Wegener's granulomatosis. In some embodiments, the mammal (e.g., human) has been previously diagnosed or is suspected of having lymphedema or edema.

A mammal can be diagnosed as having inflammation or an inflammatory disorder by a medical or veterinary professional by interviewing (when the mammal is a human) and/or physically examining the mammal. In some embodiments, a medical professional may diagnose a human as having inflammation or an inflammatory disorder by the observation of one or more symptoms of inflammation or an inflammatory disorder in a mammal. The symptoms experienced by a mammal will depend on the specific inflammatory disorder. For example, non-limiting examples of symptoms of an autoimmune disease include fever, hair loss, skin rash, skin bruising, skin ulcers, dry eyes, blurred vision, dry mouth, hoarseness, difficulty swallowing, fatigue, muscle weakness, joint stiffness, swelling in hands and feet, significant weight loss or gain, nausea, vomiting, diarrhea, irritability, lack of coordination, unsteady gait, numbness in one or more limbs, tremor, increased thirst, loss of appetite, amenoresis, shortness of breath, tightness in chest, high cholesterol levels, unexplained anemia, and alteration in blood sugar levels (hypoglycemia or hyperglycemia).

Non-limiting symptoms of atherosclerosis include chest pain (angina), sudden numbness or weakness in arms or legs, difficulty speaking or slurred speech, drooping facial muscles, and leg pain (intermittent claudication). Non-limiting examples of symptoms of lymphedema include swelling in at least part of an arm or leg, a feeling of heaviness or tightness in an arm or leg, restricted range of motion in an arm or leg, aching or discomfort in an arm or leg, recurring infections in a limb, and hardening or thickening of the skin of an arm or leg. Non-limiting symptoms of edema include swelling or puffiness of the tissue under the skin, stretched or shiny skin, skin that retains a dimple after being pressed for several seconds, and increased abdominal size.

A decrease in leukocyte extravasation in a mammal can be indicated by a decrease in one or more of the symptoms of inflammation or an inflammatory disorder in a mammal (e.g., any of the symptoms described herein). A decrease in leukocyte extravasation in a mammal can also be indicated by a decrease in the pain, swelling, or redness in an affected tissue. In some embodiments, a decrease in leukocyte extravasation in a mammal is indicated by a decrease in the levels of one or more pro-inflammatory mediators secreted by activated leukocytes (e.g., a decrease in the level of one or more cytokines, e.g., TNFα, IL-6, IL-1, IL-8, and IL-2, in the mammal). A decrease in fluid leakage of a lymph or blood vessel can be indicated by a decrease in the swelling, a decrease in the pain or loss of motion in a limb, or a decrease in the abnormal accumulation of blood, plasma, or lymph in a tissue (e.g., a limb).

The mammal may be female or male, and may be an adult or juvenile (e.g., an infant). The mammal may have been previously treated with another anti-inflammatory or cholesterol-improving therapeutic agent. The mammal may have been diagnosed or be suspected of having inflammation (e.g., acute inflammation or chronic inflammation) or an inflammatory disorder (e.g., atherosclerosis or an autoimmune disease). The mammal may have been diagnosed or be suspected of having lymphedema or edema. The mammal may also have a sibling, parent, or grandparent with elevated levels of LDL or elevated levels of total cholesterol. The mammal may have a body mass index (BMI) of between 25 to 30, or a BMI of greater than 30. The mammal may have an elevated level of triglycerides. The mammal may also have a sibling, parent, or grandparent that has had a heart attack or stroke. Where the mammal is an adult, the mammal may be, e.g., between 18 to 20 years old or at least or about 20, 25, 30, 35, 40, 45, 50, 55, 60, 65, 70, 75, 80, 85, 90, 95, or at least or about 100 years old).

The oligonucleotide that decreases the expression of Map4k4 mRNA in an endothelial cell may be administered by intravenous, intraarterial, subcutaneous, intraperitoneal, intramuscular, ocular, or intrathecal administration. In some instances, the oligonucleotide that decreases the expression of Map4k4 mRNA in an endothelial cell is administered by local administration to an inflamed tissue or a locus of the pain in the mammal. In some embodiments, the oligonucleotide that decreases the expression of Map4k4 mRNA in an endothelial cell is directly injected into a blood vessel or lymph vessel in the mammal. In other instances, the oligonucleotide that decreases the expression of Map4k4 mRNA is systemically delivered to the mammal. Combinations of such treatments are contemplated by the present invention.

The oligonucleotide that decreases Map4k4 mRNA in an endothelial cell can be administered by a medical professional (e.g., a physician, a physician's assistant, a nurse, a nurse's assistant, or a laboratory technician) or veterinary professional. Alternatively or in addition, the oligonucleotide that decreases the expression of Map4k4 mRNA in an endothelial cell can be self-administered by a human, e.g., the patient her/himself. The oligonucleotide that decreases the expression of Map4k4 mRNA in an endothelial cell can be administered in a hospital, a clinic, or a primary care facility (e.g., a nursing home), or any combination thereof.

The appropriate amount (dosage) of the oligonucleotide that decreases the expression of Map4k4 mRNA in an endothelial cell administered can be determined by a medical professional or a veterinary professional based on a number of factors including, but not limited to, the route of administration, the severity of inflammation, the mammal's responsiveness to other anti-inflammatory agents, the health of the mammal, the mammal's mass, the other therapies administered to the mammal, the age of the mammal, the sex of the mammal, and any other co-morbidity present in the mammal.

A medical professional or veterinary professional having ordinary skill in the art can readily determine the effective amount of the oligonucleotide that decreases the expression of Map4k4 mRNA in an endothelial cell that is required. For example, a physician or veterinarian could start with doses of the oligonucleotide that decreases the expression of Map4k4 mRNA in an endothelial cell (e.g., any of the oligonucleotides that decrease the expression of Map4k4 mRNA in an endothelial cell described herein) at levels lower than that required to achieve the desired therapeutic effect and then gradually increase the dose until the desired effect is achieved.

In some embodiments, the mammal is administered a dose of between 1 mg to 500 mg of any of the oligonucleotides that decrease the expression of Map4k4 mRNA in an endothelial cell described herein (e.g., between 1 mg to 400 mg, between 1 mg to 300 mg, between 1 mg and 250 mg, between 1 mg and 200 mg, between 1 mg and 150 mg, between 1 mg and 100 mg, between 1 mg and 50 mg, between 5 mg and 50 mg, and between 5 mg and 40 mg).

In some embodiments, the mammal is further administered an anti-inflammatory agent, an analgesic, and/or a cholesterol-improving therapeutic agent (e.g., any of the anti-inflammatory agents, analgesics, and/or cholesterol-improving therapeutic agents described herein). In some embodiments, the mammal is administered a dose of between 1 mg to 500 mg (e.g., each) of an anti-inflammatory agent, an analgesic, and/or a cholesterol-improving therapeutic agent (e.g., between 1 mg to 400 mg, between 1 mg to 300 mg, between 1 mg and 250 mg, between 1 mg and 200 mg, between 1 mg and 150 mg, between 1 mg and 100 mg, between 1 mg and 50 mg, between 5 mg and 50 mg, between 5 mg and 40 mg, between 20 mg and 400 mg, between 20 mg and 300 mg, between 50 mg and 300 mg, and between 50 mg and 200 mg). The anti-inflammatory agent, analgesic, and/or cholesterol-improving therapeutic agent can be administered to the mammal at substantially the same time as the oligonucleotide that decreases the expression of Map4k4 mRNA in an endothelial cell.

Alternatively or in addition, the anti-inflammator agent, the analgesic, and/or the cholesterol-improving therapeutic agent may be administered to the mammal at one or more time points other than the time point at which the oligonucleotide that decreases the expression of Map4k4 mRNA is administered. In some embodiments, the anti-inflammatory agent, the analgesic, and/or the cholesterol-improving therapeutic agent is formulated together with an oligonucleotide that decreases the expression of Map4k4 mRNA in an endothelial cell (e.g., using any of the examples of formulations and compositions described herein).

In some embodiments, the anti-inflammatory agent, the analgesic, and/or the cholesterol-improving therapeutic agent are formulated in a first dosage form, and the oligonucleotide that decreases the expression of Map4k4 mRNA in an endothelial cell is formulated in a second dosage form. In some embodiments where the anti-inflammatory agent, the analgesic, and/or the cholesterol-improving therapeutic agent are formulated in a first dosage form, and the oligonucleotide that decreases the expression of Map4k4 mRNA is formulated in a second dosage form, the first dosage form and the second dosage form can be formulated for the same route of administration (e.g., oral, subcutaneous, intramuscular, intravenous, intaarterial, intrathecal, and intraperitoneal administration) or can be formulated for different routes of administration (e.g., the first dosage form formulated for oral administration and the second dosage form formulated for subcutaneous administration). Combinations of such treatment regimes are clearly contemplated in the present invention.

The amount of the oligonucleotide that decreases the expression of Map4k4 mRNA in an endothelial cell (and optionally, an anti-inflammatory agent, an analgesic, and/or a cholesterol-improving therapeutic agent) administered will depend on whether the administration is local or systemic. In some embodiments, the mammal is administered more than one dose of the oligonucleotide that decreases the expression of Map4k4 mRNA in an endothelial cell. In some embodiments, the mammal is administered more than one dose of any of the compositions described herein. In some embodiments, the mammal is administered a dose of an oligonucleotide that decreases the expression of Map4k4 mRNA in an endothelial cell at least once a month (e.g., at least twice a month, at least three times a month, at least four times a month, at least once a week, at least twice a week, three times a week, once a day, or twice a day).

In some embodiments, an oligonucleotide that decreases the expression of Map4k4 mRNA in an endothelial cell is administered to a mammal chronically. In some embodiments, any of the compositions described herein is administered to the mammal chronically. Chronic treatments include any form of repeated administration for an extended period of time, such as repeated administrations for one or more months, between a month and a year, one or more years, or longer. In some embodiments, chronic treatments can involve regular administrations, for example one or more times a day, one or more times a week, or one or more times a month. In general, a suitable dose such as a daily dose of the oligonucleotide that decreases the expression of Map4k4 mRNA in an endothelial cell will be the amount of the oligonucleotide that is the lowest dose effective to produce a desired therapeutic effect. Such an effective dose will generally depend upon the factors described herein. If desired, the effective daily dose of the oligonucleotide that decreases the expression of Map4k4 mRNA in an endothelial cell can be administered as two, three, four, five, or six or more sub-doses administered separately at appropriate intervals throughout the day, optionally, in unit dosage forms.

In some embodiments, the oligonucleotide that decreases the expression of Map4k4 mRNA in an endothelial cell is formulated for sustained-release (e.g., formulated in a biodegradable polymer or a nanoparticle). In some embodiments, the oligonucleotide that decreases the expression of Map4k4 mRNA in an endothelial cell is administered locally to the site of pain or inflammation in the mammal. In some embodiments, the oligonucleotide that decreases the expression of Map4k4 mRNA in an endothelial cell is administered systemically (e.g., oral, intravenous, intaarterial, intraperitoneal, intramuscular, or subcutaneous administration). In some embodiments, the oligonucleotide that decreases the expression of Map4k4 mRNA in an endothelial cell is formulated for oral, intraglandular, periglandular, subcutaneous, interductal, intramuscular, intraperitoneal, intramuscular, intraarterial, transdermal, interlymphatic, or intravenous administration).

Methods of Treating Inflammation, Inflammatory or Vessel Fluid Leakage Disorders, and Decreasing Atherosclerotic Plaque Formation Also provided herein are methods of treating inflammation (e.g., acute or chronic inflammation), an inflammatory disorder (e.g., an autoimmune disease (e.g., any of the inflammatory diseases described herein) or atherosclerosis), or a vessel fluid leakage disorder (e.g., lymphedema or edema), and methods of reducing the formation of atherosclerotic plaques in a blood vessel (e.g., an artery) in a mammal in need thereof. These methods include or consist of administering to a mammal in need thereof an oligonucleotide that decreases the expression of a Map4k4 mRNA in an endothelial cell (e.g., any of the oligonucleotides that decrease the expression of a Map4k4 mRNA in an endothelial cell described herein) in an amount sufficient to treat inflammation, the inflammatory disorder (e.g., atherosclerosis), or the vessel fluid leakage disorder in the mammal, or in an amount sufficient to decrease expression of leukocyte adhesion molecules in endothelial cells lining blood or lymph vessels.

In some embodiments of all the methods described herein, the oligonucleotide that decreases the expression of Map4k4 mRNA an endothelial cell is "synthetic," i.e., is synthesized in vitro. In some embodiments of all the methods described herein, the oligonucleotide that decreases the expression of Map4k4 mRNA in an endothelial cell includes or consists of one or more (e.g., at least 2, 3, 4, 5, 6, 7, 8, 9, 10, 11, 12, 13, 14, 15, 16, 17, 18, 19, 20, 21, 22, 23, 24, 25, or 26) modified nucleotides (e.g., one or more different types of modified nucleotides known in the art or described herein).

In some embodiments, the mammal has been previously diagnosed or is suspected of having inflammation (e.g., acute or chronic inflammation). In some embodiments, the mammal is identified as having an increased risk of developing atherosclerosis. In some embodiments, the mammal has been previously diagnosed or is suspected of having an inflammatory disorder (e.g., an autoimmune disease (e.g., any of the autoimmune disorders described herein) or atherosclerosis). In some embodiments, the mammal has been previously diagnosed or is suspected of having a vessel fluid leakage disorder (e.g., lymphedema or edema). The mammal may be female or male, and may be an adult or juvenile (e.g., an infant). Where the mammal is an adult, the mammal may be, e.g., between 18 to 20 years old or at least or about 20, 25, 30, 35, 40, 45, 50, 55, 60, 65, 70, 75, 80, 85, 90, 95, or at least or about 100 years old).

A mammal can be diagnosed as having inflammation (e.g., chronic or acute inflammation), an inflammatory disorder (e.g., atherosclerosis), or a vessel fluid leakage disorder by a medical profession by observation of one or more symptoms in the mammal (e.g., one or more of any of the symptoms of inflammation, an inflammatory disorder, or a vessel fluid leakage disorder described herein or known in the art). In some embodiments, the mammal may already be receiving a treatment for inflammation, an inflammatory disorder (e.g., atherosclerosis), or a vessel fluid leakage disorder. In some embodiments, the prior treatment for inflammation, an inflammatory disorder (e.g., atherosclerosis), or a vessel fluid leakage disorder has been unsuccessful.

The oligonucleotide that decreases the expression of Map4k4 mRNA in an endothelial cell may be administered by intravenous, intraarterial, subcutaneous, intraperitoneal, interlymphatic, intramuscular, ocular, or intrathecal administration. The oligonucleotide can be formulated using any of the examples of techniques described herein (e.g., formulated for subcutaneous, intravenous, intraarterial, interlymphatic, or intrathecal administration, and/or formulated in a liposome or nanoparticle).

The oligonucleotide that decreases Map4k4 mRNA in an endothelial cell can be administered by a medical professional (e.g., a physician, a physician's assistant, a nurse, a nurse's assistant, or a laboratory technician) or veterinary professional. Alternatively or in addition, the oligonucleotide that decreases the expression of Map4k4 mRNA in an endothelial cell can be self-administered by a human, e.g., the patient her/himself. The oligonucleotide that decreases the expression of Map4k4 mRNA in an endothelial cell can be administered in a hospital, a clinic, or a primary care facility (e.g., a nursing home), or any combination thereof.

In some embodiments, the mammal is administered a dose of between 1 mg to 500 mg of any of the oligonucleotides that decrease the expression of Map4k4 mRNA in an endothelial cell described herein (e.g., using any of the doses, formulations, and routes of administration described herein).

Successful treatment of inflammation or an inflammatory disorder (e.g., atherosclerosis) can be indicated by a decrease in the number or the severity or frequency of one or more of the symptoms of inflammation or an inflammatory disorder in a mammal (e.g., any of the symptoms described herein). Successful treatment of inflammation or an inflammatory disorder can also indicated by a decrease in the pain, swelling, or redness in an affected tissue. In some embodiments, successful treatment of inflammation or an inflammatory disorder in a mammal can be indicated by a decrease in the levels of one or more inflammatory mediators secreted by activated leukocytes in the mammal (e.g., a decrease in the level of one or more cytokines, e.g., TNFα, IL-6, IL-1, IL-8, and IL-2). Successful treatment of a vessel fluid leakage disorder can be indicated by a decrease in the swelling, a decrease in the pain or loss of motion in a limb, or a decrease in the abnormal accumulation of blood, plasma, or lymph in a tissue (e.g., a limb).

In another example, successful treatment of the inflammatory disorder of atherosclerosis can be observed by a decrease in the number, frequency, and/or duration of one or more symptoms of atherosclerosis in the mammal (e.g., chest pain (angina), sudden numbness or weakness in arms or legs, shortness of breath, arrhythmia, dizziness, sudden and severe headache, sleep problems, fatigue, difficulty speaking or slurred speech, confusion, drooping facial muscles, detection of a bruit, and leg pain (intermittent claudication)). Successful treatment of atherosclerosis can also be detected using imaging (e.g., Doppler tests using ultrasound or sound waves, magnetic resonance arteriography, CT angiography, arteriograms, and/or angiography). A reduction in the formation of atherosclerotic plaques in a mammal can be detected by a decrease in the number, frequency, and/or duration of one or more symptoms of atherosclerosis in the mammal (e.g., chest pain (angina), sudden numbness or weakness in arms or legs, shortness of breath, arrhythmia, dizziness, sudden and severe headache, sleep problems, fatigue, difficulty speaking or slurred speech, confusion, drooping facial muscles, detection of a bruit, and leg pain (intermittent claudication)), a decrease in the rate of the development of new symptoms of atherosclerosis (e.g., any of those symptoms described herein), or a decrease in the rate of worsening of one or more symptoms of atherosclerosis (e.g., any of the symptoms described herein) in a mammal (e.g., a human) receiving any of the treatments described herein, as compared to a control mammal (e.g., a human) having atherosclerosis but receiving a different treatment or a placebo. A reduction in the formation of atherosclerotic plaques in a mammal (e.g., a human) over time can also be detected using periodic imaging (e.g., Doppler tests using ultrasound or sound waves, magnetic resonance arteriography, CT angiography, arteriograms, and/or angiography). For example, the rate of formation of atherosclerotic plaques in a mammal (e.g., a human) receiving any of the treatments described herein can be detected over time at two or more time points (e.g., using any of the imaging techniques described herein), and the changes in atherosclerotic plaques over time in the mammal (e.g., human) receiving the treatment can be compared to the changes in atherosclerotic plaques over a similar time frame in a control mammal (e.g., a human) receiving a different treatment or a placebo. In these examples, the mammal that is administered a treatment as described herein and the control mammal can have the same disease (e.g., atherosclerosis), the same risk of disease (e.g., increased risk of developing atherosclerosis), or be diagnosed with the same disease (e.g., atherosclerosis). A mammal can be identified as having an increased risk of developing atherosclerosis using methods known in the art. For example, one or more of the following indicates that a mammal has an increased risk of developing atherosclerosis: high LDL level, low HDL level, current smoking habit, high blood pressure (e.g., 140/90 or greater), diagnosed with diabetes, and family history of heart attacks.

In some embodiments, the mammal is further administered an anti-inflammatory agent, an analgesic, and/or a cholesterol-improving therapeutic agent (e.g., any of the cholesterol-improving agents described herein). In some embodiments, the mammal is further administered an anti-inflammatory agent, an analgesic, and/or a cholesterol-improving therapeutic agent using any of the dosages, formulations, and routes of administration described herein. The anti-inflammatory agent, analgesic, and/or cholesterol-improving therapeutic agent can be administered to the mammal at substantially the same time as the oligonucleotide that decreases the expression of Map4k4 mRNA in an endothelial cell.

Alternatively or in addition, the anti-inflammatory agent, the analgesic, and/or the cholesterol-improving therapeutic agent may be administered to the mammal at one or more time points other than the time point at which the oligonucleotide that decreases the expression of Map4k4 mRNA is administered. In some embodiments, the anti-inflammatory agent, the analgesic, and/or the cholesterol-improving therapeutic agent is formulated together with an oligonucleotide that decreases the expression of Map4k4 mRNA in an endothelial cell (e.g., using any of the examples of formulations and compositions described herein). In some embodiments, the anti-inflammatory agent, the analgesic, and the cholesterol-improving therapeutic agent are formulated in a first dosage form, and the oligonucleotide that decreases the expression of Map4k4 mRNA in an endothelial cell is formulated in a second dosage form. In some embodiments where the anti-inflammatory agent, the analgesic, and/or the cholesterol-improving therapeutic agent are formulated in a first dosage form, and the oligonucleotide that decreases the expression of Map4k4 mRNA is formulated in a second dosage form, the first dosage form and the second dosage form can be formulated for the same route of administration (e.g., oral, subcutaneous, intramuscular, intravenous, intaarterial, intrathecal, interlymphatic, and intraperitoneal administration) or can be formulated for different routes of administration (e.g., the first dosage form formulated for oral administration and the second dosage form formulated for subcutaneous administration). Combinations of such treatment regimes are clearly contemplated in the present invention.

In some embodiments where arteriosclerosis is treated in a mammal, the mammal is further administered one of more additional agents useful for treating atherosclerosis selected from the group of: an anti-inflammatory agent, an analgesic, a cholesterol-improving therapeutic agent (e.g., a statin), a fibrate (e.g., gemfibrozil or fenofibrate), nicotinic acid, bile acid sequestrants (e.g., bcholestyramine, colestipol, and colesevelam), omega-3 oil supplement (Lovaza or Vascepa), and/or an anti-platelet drug or blood thinner (e.g., aspirin, clopidogrel, ticagrelor, prasugrel, and warfarin) using any of the dosages, formulations, and routes of administration described herein. The anti-inflammatory agent, the analgesic, the cholesterol-improving therapeutic agent, the fibrate, the nicotinic acid, the bile acid sequestrant, the omega-3 oil supplement, and/or the anti-platelet drug or blood thinner can be administered to the mammal at substantially the same time as the oligonucleotide that decreases the expression of Map4k4 mRNA in an endothelial cell.

Alternatively or in addition, the anti-inflammatory agent, the analgesic, the cholesterol-improving therapeutic agent, the fibrate, the nicotinic acid, the bile acid sequestrant, the omega-3 oil supplement, and/or the anti-platelet drug or blood thinner may be administered to the mammal at one or more time points other than the time point at which the oligonucleotide that decreases the expression of Map4k4 mRNA is administered. In some embodiments, the anti-inflammatory agent, the analgesic, the cholesterol-improving therapeutic agent, the fibrate, the nicotinic acid, the bile acid sequestrant, the omega-3 oil supplement, and/or the anti-platelet drug or blood thinner is formulated together with an oligonucleotide that decreases the expression of Map4k4 mRNA in an endothelial cell (e.g., using any of the examples of formulations and compositions described herein).

In some embodiments, the anti-inflammatory agent, the analgesic, the cholesterol-improving therapeutic agent, the fibrate, the nicotinic acid, the bile acid sequestrant, the omega-3 oil supplement, and/or the anti-platelet drug or blood thinner are formulated in a first dosage form, and the oligonucleotide that decreases the expression of Map4k4 mRNA in an endothelial cell is formulated in a second dosage form. In some embodiments where the anti-inflammatory agent, the analgesic, the cholesterol-improving therapeutic agent, the fibrate, the nicotinic acid, the bile acid sequestrant, the omega-3 oil supplement, and/or the anti-platelet drug or blood thinner are formulated in a first dosage form, and the oligonucleotide that decreases the expression of Map4k4 mRNA is formulated in a second dosage form, the first dosage form and the second dosage form can be formulated for the same route of administration (e.g., oral, subcutaneous, intramuscular, intravenous, intaarterial, intrathecal, interlymphatic, and intraperitoneal administration) or can be formulated for different routes of administration (e.g., the first dosage form formulated for oral administration and the second dosage form formulated for subcutaneous administration). Combinations of such treatment regimes are clearly contemplated in the present invention.

The amount of the oligonucleotide that decreases the expression of Map4k4 mRNA in an endothelial cell (and optionally, an anti-inflammatory agent, an analgesic, and/or a cholesterol-improving therapeutic agent) administered will depend on whether the administration is local or systemic. In some embodiments, the mammal is administered more than one dose of the oligonucleotide that decreases the expression of Map4k4 mRNA in an endothelial cell. In some embodiments, the mammal is administered more than one dose of any of the compositions described herein. In some embodiments, the mammal is administered a dose of an oligonucleotide that decreases the expression of Map4k4 mRNA in an endothelial cell at least once a month (e.g., at least twice a month, at least three times a month, at least four times a month, at least once a week, at least twice a week, three times a week, once a day, or twice a day).

In some embodiments, an oligonucleotide that decreases the expression of Map4k4 mRNA in an endothelial cell is administered to a mammal chronically. In some embodiments, any of the compositions described herein is administered to the mammal chronically. Chronic treatments include any form of repeated administration for an extended period of time, such as repeated administrations for one or more months, between a month and a year, one or more years, or longer. In some embodiments, chronic treatments can involve regular administrations, for example one or more times a day, one or more times a week, or one or more times a month. In general, a suitable dose such as a daily dose of the oligonucleotide that decreases the expression of Map4k4 mRNA in an endothelial cell will be the amount of the oligonucleotide that is the lowest dose effective to produce a desired therapeutic effect. Such an effective dose will generally depend upon the factors described herein. If desired, the effective daily dose of the oligonucleotide that decreases the expression of Map4k4 mRNA in an endothelial cell can be administered as two, three, four, five, or six or more sub-doses administered separately at appropriate intervals throughout the day, optionally, in unit dosage forms.

In some embodiments, the oligonucleotide that decreases the expression of Map4k4 mRNA in an endothelial cell is formulated for sustained-release (e.g., formulated in a biodegradable polymer or a nanoparticle). In some embodiments, the oligonucleotide that decreases the expression of Map4k4 mRNA in an endothelial is formulated in a nanoparticle as described in U.S. Patent Application Serial Nos. WO 2010/042555, WO 2011/084620, and WO 2012/040623. In some embodiments, the oligonucleotide that decreases the expression of Map4k4 mRNA in an endothelial cell is administered locally to the site of pain, inflammation, edema, or lymphedema in the mammal. In some embodiments, the oligonucleotide that decreases the expression of Map4k4 mRNA in an endothelial cell is administered systemically (e.g., oral, intravenous, intaarterial, intraperitoneal, intramuscular, interlymphatic, or subcutaneous administration). In some embodiments, the oligonucleotide that decreases the expression of Map4k4 mRNA in an endothelial cell is formulated for oral, intraglandular, periglandular, subcutaneous, interductal, intramuscular, intraperitoneal, intramuscular, intraarterial, transdermal, interlymphatic, or intravenous administration).

Oligonucleotides that Decrease the Expression of Map4k4 mRNA

Non-limiting examples of oligonucleotides that can decrease the expression of Map4k4 mRNA in a mammalian endothelial cell include inhibitory nucleic acids (e.g., small inhibitory nucleic acids (siRNA)), antisense oligonucleotides, and ribozymes. Exemplary aspects of these different oligonucleotides are described below. Any of the examples of oligonucleotides that can decrease expression of Map4k4 mRNA in an endothelial cell can be synthetic, i.e., can be synthesized in vitro.

Antisense Oligonucleotides

Oligonucleotides that decrease the expression of Map4k4 mRNA expression in a mammalian endothelial cell include antisense nucleic acid molecules, i.e., nucleic acid molecules whose nucleotide sequence is complementary to all or part of an mRNA based on the sequence of a gene encoding a Map4k4 protein (e.g., complementary to all or a part of SEQ ID NO: 2, 4, 6, 8, 10, or 12). An antisense nucleic acid molecule can be antisense to all or part of a non-coding region of the coding strand of a nucleotide sequence encoding a Map4k4 protein. Non-coding regions (5' and 3' untranslated regions) are the 5' and 3' sequences that flank the coding region in a gene and are not translated into amino acids.

Based upon the sequences disclosed herein, one of skill in the art can easily choose and synthesize any of a number of appropriate antisense molecules to target a Map4k4 gene described herein. For example, a "gene walk" comprising a series of oligonucleotides of 15-30 nucleotides spanning the length of a Map4k4 gene can be prepared, followed by testing for inhibition of expression of the Map4k4 gene. Optionally, gaps of 5-10 nucleotides can be left between the oligonucleotides to reduce the number of oligonucleotides synthesized and tested. Antisense oligonucleotides targeting Map4k4 can also be designed using the software available at the Integrated DNA Technologies website.

An antisense oligonucleotide can be, for example, about 5, 10, 15, 20, 25, 30, 35, 40, 45, or 50 nucleotides or more in length. An antisense nucleic acid can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used.

Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules described herein can be prepared in vitro and administered to a mammal, e.g., a human. Alternatively, they can be generated in situ such that they hybridize with or bind to cellular mRNA and/or genomic DNA encoding a Map4k4 protein to thereby inhibit expression, e.g., by inhibiting transcription and/or translation. The hybridization can be by conventional nucleotide complementarities to form a stable duplex, or, for example, in the case of an antisense nucleic acid molecule that binds to DNA duplexes, through specific interactions in the major groove of the double helix. An example of a route of administration of antisense nucleic acid molecules includes direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies that bind to cell surface receptors or antigens. The antisense nucleic acid molecules can also be delivered to cells using the vectors described herein. For example, to achieve sufficient intracellular concentrations of the antisense molecules, vector constructs can be used in which the antisense nucleic acid molecule is placed under the control of a strong pol II or pol III promoter. In some embodiments, the vector used to express the oligonucleotide that decreases the expression of Map4k4 mRNA in a mammalian fibroblast can be a lentivirus, a retrovirus, or an adenovirus vector.

An antisense nucleic acid molecule of the invention can be an α-anomeric nucleic acid molecule. An α-anomeric nucleic acid molecule forms specific double-stranded hybrids with complementary RNA in which, contrary to the usual, β-units, the strands run parallel to each other (Gaultier et al., *Nucleic Acids Res.* 15:6625-6641, 1987). The antisense nucleic acid molecule can also comprise a 2'-O-methylribonucleotide (Inoue et al., *Nucleic Acids Res.*, 15:6131-6148, 1987) or a chimeric RNA-DNA analog (Inoue et al., *FEBS Lett.*, 215:327-330, 1987).

Antisense molecules that are complementary to all or part of a Map4k4 gene are also useful for assaying expression of a Map4k4 gene using hybridization methods known in the art. For example, the antisense molecule is labeled (e.g., with a radioactive molecule) and an excess amount of the labeled antisense molecule is hybridized to an RNA sample. Unhybridized labeled antisense molecule is removed (e.g., by washing) and the amount of hybridized antisense molecule measured. The amount of hybridized molecule is measured and used to calculate the amount of expression of the Map4k4 mRNA. In general, antisense molecules used for this purpose can hybridize to a sequence from a Map4k4 gene under high stringency conditions such as those described herein. When the RNA sample is first used to synthesize cDNA, a sense molecule can be used. It is also possible to use a double-stranded molecule in such assays as long as the double-stranded molecule is adequately denatured prior to hybridization.

Non-limiting examples of antisense oligonucleotides that decrease Map4k4 mRNA expression in an endothelial cell include: CTTCTCCACTCTCTCCCACA (SEQ ID NO: 13), CCTCTTCTTCCTCACTCCCAC (SEQ ID NO: 14), CTTCTCCACTCTCTCCCAC (SEQ ID NO: 15), GCTTCTCCACTCTCTCCCAC (SEQ ID NO: 16), and GCTTCTCCACTCTC TCCACA (SEQ ID NO: 17). All antisense sequences are predicted to bind within the 1000-3000 bp region of the Map4k4 gene sequence.

Ribozymes

Also provided are ribozymes that have specificity for sequences encoding a Map4k4 protein described herein (e.g., specificity for a Map4k4 mRNA, e.g., specificity for SEQ ID NO: 2, 4, 6, 8, 10, or 12). Ribozymes are catalytic RNA molecules with ribonuclease activity that are capable of cleaving a single-stranded nucleic acid, such as an mRNA, to which they have a complementary region. Thus, ribozymes (e.g., hammerhead ribozymes (described in Haselhoff and Gerlach, *Nature,* 334:585-591, 1988)) can be used to catalytically cleave mRNA transcripts to thereby inhibit translation of the protein encoded by the mRNA. A ribozyme having specificity for a nucleic acid molecule of the invention can be designed based upon the nucleotide sequence of a cDNA disclosed herein. For example, a derivative of a Tetrahymena L-19 IVS RNA can be constructed in which the nucleotide sequence of the active site is complementary to the nucleotide sequence to be cleaved in a Map4k4 mRNA (Cech et al. U.S. Pat. No. 4,987,071; and Cech et al., U.S. Pat. No. 5,116,742). Alternatively, a Map4k4 mRNA can be used to select a catalytic RNA having a specific ribonuclease activity from a pool of RNA molecules. See, e.g., Bartel and Szostak, *Science,* 261:1411-1418, 1993.

Also provided herein are nucleic acid molecules that form triple helical structures. For example, expression of a Map4k4 polypeptide can be inhibited by targeting nucleotide sequences complementary to the regulatory region of the gene encoding the Map4k4 polypeptide (e.g., the promoter and/or enhancer, e.g., a sequence that is at least 1 kb, 2 kb, 3 kb, 4 kb, or 5 kb upstream of the transcription initiation start site) to form triple helical structures that prevent transcription of the gene in target cells. See generally Helene, *Anticancer Drug Des.* 6(6):569-84, 1991; Helene, *Ann. N.Y. Acad. Sci.,* 660:27-36, 1992; and Maher, *Bioassays,* 14(12):807-15, 1992.

In various embodiments, nucleic acid molecules (e.g., nucleic acid molecules used to decrease expression of Map4k4 mRNA in a mammalian fibroblast) can be modified at the base moiety, sugar moiety, or phosphate backbone to improve, e.g., the stability, hybridization, or solubility of the molecule. For example, the deoxyribose phosphate backbone of the nucleic acids can be modified to generate peptide nucleic acids (see Hyrup et al., Bioorganic & Medicinal Chem., 4(1): 5-23, 1996). Peptide nucleic acids (PNAs) are nucleic acid mimics, e.g., DNA mimics, in which the deoxyribose phosphate backbone is replaced by a pseudopeptide backbone and only the four natural nucleobases are retained. The neutral backbone of PNAs allows for specific hybridization to DNA and RNA under conditions of low ionic strength. The synthesis of PNA oligomers can be performed using standard solid phase peptide synthesis protocols, e.g., as described in Hyrup et al., 1996, supra; Perry-O'Keefe et al., Proc. Natl. Acad. Sci. USA, 93: 14670-675, 1996.

PNAs can be used in therapeutic and diagnostic applications. For example, PNAs can be used as antisense or antigene agents for sequence-specific modulation of gene expression by, e.g., inducing transcription or translation arrest or inhibiting replication. PNAs can also be used, e.g., in the analysis of single base pair mutations in a gene by, e.g., PNA directed PCR clamping; as artificial restriction enzymes when used in combination with other enzymes, e.g., S1 nucleases (Hyrup, 1996, supra; or as probes or primers for DNA sequence and hybridization (Hyrup, 1996, supra; Perry-O'Keefe et al., Proc. Natl. Acad. Sci. USA, 93: 14670-675, 1996).

PNAs can be modified, e.g., to enhance their stability or cellular uptake, by attaching lipophilic or other helper groups to PNA, by the formation of PNA-DNA chimeras, or by the use of liposomes or other techniques of drug delivery known in the art. For example, PNA-DNA chimeras can be generated which may combine the advantageous properties of PNA and DNA. Such chimeras allow DNA recognition enzymes, e.g., RNAse H and DNA polymerases, to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup, 1996, supra). The synthesis of PNA-DNA chimeras can be performed as described in Hyrup, 1996, supra, and Finn et al., Nucleic Acids Res., 24:3357-63, 1996. For example, a DNA chain can be synthesized on a solid support using standard phosphoramidite coupling chemistry and modified nucleoside analogs. Compounds such as 5'-(4-methoxytrityl)amino-5'-deoxy-thymidine phosphoramidite can be used as a link between the PNA and the 5' end of DNA (Mag et al., Nucleic Acids Res., 17:5973-88, 1989). PNA monomers are then coupled in a stepwise manner to produce a chimeric molecule with a 5' PNA segment and a 3' DNA segment (Finn et al., Nucleic Acids Res., 24:3357-63, 1996). Alternatively, chimeric molecules can be synthesized with a 5' DNA segment and a 3' PNA segment (Peterser et al., Bioorganic Med. Chem. Lett., 5:1119-11124, 1975).

In some embodiments, the oligonucleotide includes other appended groups such as peptides (e.g., for targeting host cell receptors in vivo), or agents facilitating transport across the cell membrane (see, e.g., Letsinger et al., Proc. Natl. Acad. Sci. USA, 86:6553-6556, 1989; Lemaitre et al., Proc. Natl. Acad. Sci. USA, 84:648-652, 1989; WO 88/09810) or the blood-brain barrier (see, e.g., WO 89/10134). In addition, oligonucleotides can be modified with hybridization-triggered cleavage agents (see, e.g., Krol et al., Bio/Techniques, 6:958-976, 1988) or intercalating agents (see, e.g., Zon, Pharm. Res., 5:539-549, 1988). To this end, the oligonucleotide may be conjugated to another molecule, e.g., a peptide, hybridization triggered cross-linking agent, transport agent, hybridization-triggered cleavage agent, etc.

siRNA

Another means by which expression of a Map4k4 mRNA can be decreased in mammalian endothelial cells is by RNA interference (RNAi). RNAi is a process in which mRNA is degraded in host cells. To inhibit an mRNA, double-stranded RNA (dsRNA) corresponding to a portion of the gene to be silenced (e.g., a gene encoding a Map4k4 polypeptide) is introduced into a cell. The dsRNA is digested into 21-23 nucleotide-long duplexes called short interfering RNAs (or siRNAs), which bind to a nuclease complex to form what is known as the RNA-induced silencing complex (or RISC). The RISC targets the homologous transcript by base pairing interactions between one of the siRNA strands and the endogenous mRNA. It then cleaves the mRNA about 12 nucleotides from the 3' terminus of the siRNA (see Sharp et al., Genes Dev. 15:485-490, 2001, and Hammond et al., Nature Rev. Gen., 2:110-119, 2001).

RNA-mediated gene silencing can be induced in mammalian cells in many ways, e.g., by enforcing endogenous expression of RNA hairpins (see, Paddison et al., Proc. Natl. Acad. Sci. USA, 99:1443-1448, 2002) or, as noted above, by transfection of small (21-23 nt) dsRNA (reviewed in Caplen, Trends in Biotech., 20:49-51, 2002). Methods for modulating gene expression with RNAi are described, e.g., in U.S. Pat. No. 6,506,559 and U.S. Patent Publication No. 2003/0056235, which are hereby incorporated by reference.

Standard molecular biology techniques can be used to generate siRNAs. Short interfering RNAs can be chemically synthesized, recombinantly produced, e.g., by expressing RNA from a template DNA, such as a plasmid, or obtained from commercial vendors such as Dharmacon. The RNA used to mediate RNAi can include synthetic or modified nucleotides, such as phosphorothioate nucleotides. Methods of transfecting cells with siRNA or with plasmids engineered to make siRNA are routine in the art.

The siRNA molecules used to decrease expression of a Map4k4 mRNA can vary in a number of ways. For example, they can include a 3' hydroxyl group and strands of 21, 22, or 23 consecutive nucleotides. They can be blunt ended or include an overhanging end at either the 3' end, the 5' end, or both ends. For example, at least one strand of the RNA molecule can have a 3' overhang from about 1 to about 6 nucleotides (e.g., 1-5, 1-3, 2-4 or 3-5 nucleotides (whether pyrimidine or purine nucleotides) in length. Where both strands include an overhang, the length of the overhangs may be the same or different for each strand.

To further enhance the stability of the RNA duplexes, the 3' overhangs can be stabilized against degradation (by, e.g., including purine nucleotides, such as adenosine or guanosine nucleotides or replacing pyrimidine nucleotides by modified analogues (e.g., substitution of uridine 2 nucleotide 3' overhangs by 2'-deoxythymidine is tolerated and does not affect the efficiency of RNAi). Any siRNA can be used in the methods of decreasing Map4k4 mRNA, provided it has sufficient homology to the target of interest (e.g., a sequence present in SEQ ID NO: 2, 4, 6, 8, 10, or 12). There is no upper limit on the length of the siRNA that can be used (e.g., the siRNA can range from about 21 base pairs of the gene to the full length of the gene or more (e.g., 50-60, 60-70, 70-80, 80-90, or 90-100 base pairs).

Non-limiting examples of siRNAs that can be used to decrease Map4k4 mRNA expression in an endothelial cell include: TGCTGTCTGGTGAAGAATTA (SEQ ID NO: 18), GACCAACTCTGGCTTGTTATT (SEQ ID NO: 19), CAGAAGTGGCCAAGGGAAA (SEQ ID NO: 20), AGAAGAAGGTGCA GGTTTA (SEQ ID NO: 21), AGAGAAG GCAATAGAGATA (SEQ ID NO: 22), GCTTACATCTCCAGGGAAA (SEQ ID NO: 23). SiRNAs that can be used to decrease the expression of Map4k4 mRNA in an endothelial cell can also be purchased from Dharmacon (e.g., SEQ ID NO: 19).

Compositions and Kits

Oligonucleotides that decrease the expression of Map4k4 mRNA in an endothelial can be used to treat or prevent the development of atherosclerosis in a mammal (e.g., a human). Provided herein are compositions that contain an oligonucleotide that decreases the expression of Map4k4 mRNA in an endothelial cell (e.g., any of the oligonucleotides that decrease expression of Map4k4 mRNA in an endothelial cell described herein) and one or more of a cholesterol-improving therapeutic agent (e.g., any of the exemplary cholesterol-improving therapeutic agents described herein or known in the art), a fibrate, a nicotinic acid, a bile acid sequestrant, an omega-3 oil supplement, and/or an anti-platelet drug or blood thinner. Such compositions can be useful for treating or reducing the rate of development of atherosclerosis or reducing the formation of atherosclerotic plaques in a blood vessel in a mammal. In some embodiments, the composition can contain one or more of: a pharmaceutically acceptable excipient or buffer, an antimicrobial or antifungal agent, or a stabilizing protein (e.g., human serum albumin).

In some embodiments, the cholesterol-improving therapeutic agent is an agent that decreases the level of LDL in a mammal, increases the level of HDL in a mammal, or decreases the total cholesterol level in a mammal. In some embodiments, the cholesterol-improving therapeutic agent is a statin (e.g., lovastatin, atorvastatin, rosuvastatin, sitagliptin, simvastatin, fluvastatin, atorvastatin, pitavastatin, and pravastatin), gemfibrozil, fenofibrate, niacin, cholestyramine, colestipol, clofibrate, ezetimibe, and amlodipine.

In some embodiments, the compositions can further include one or more of an anti-inflammatory agent and/or an analgesic. Non-limiting examples of anti-inflammatory agents include corticosteroids, non-steroidal anti-inflammatory drugs (NSAIDs, e.g., cyclooxygenase I (COX I) inhibitors and cyclooxygenase II (COX-II) inhibitors), immune selective anti-inflammatory derivatives (ImSAIDs), and biologics. Non-limiting examples of NSAIDs that can be salicylates (e.g., aspirin, diflusinal, and salsalate), propionic acid derivatives (e.g., ibuprofen, dexiboprofen, naproxen, fenoprofen, ketoprofen, dexketoprofen, flurbiprofen, oxaprozin, and loxoprofen), acetic acid derivatives (e.g., indomethacin, sulindac, etodolac, ketorolac, diclofenac, and nabumetone), enolic acid derivatives (e.g., piroxicam, meloxicam, tanoxicam, droxicam, lornoxicam, and isoxicam), fenamic acid derivatives (e.g., mefamic acid, meclofenamic acid, flufenamic acid, and tolfenamic acid), sulphonanilides (e.g., nimesulide), licofelone, and lysine clonixinate. In some embodiments, an NSAID is a COX-I inhibitor or a COX-II inhibitor. Non-limiting examples of COX-I inhibitors include aspirin, ibuprofen, and naproxen. Non-limiting examples of COX-II inhibitors include celecoxib, valdecoxib, and rofecoxib. Non-limiting examples of ImSAIDs include FEG (Phe-Glu-Gly), its D-isomer feG, and SGP-T peptide. Non-limiting examples of corticosteroids include hydrocortisone, cortisone acetate, tixocortol pivalate, prednisolone, methylprednisolone, prednisone, triamcinolone acetonide, triamcinolone alcohol, mometasone, amcinonide, budesonide, desonide, fluocinolone, halcinonide, betamethasone, dexamethasone, and fluocortolone. Non-limiting examples of biologics include tocilizumab, certolizumab, etanercept, adalimumab, anakinra, abatacept, efalizumab, infliximab, rituximab, and golimumab. Non-limiting examples of analgesics include opioid drugs (e.g., morphine, opium, codeine, oxycodone, hydrocodone, diamorphine, dihydromorphine, pethidine, buprenorphine, and tramadol), paracetamol, acetaminophen, venlafaxine, flupirtine, nefopam, gabapentin, orphenadrine, cyclobenzaprine, trazodone, gabapentin, clonidine, fentanyl, methadone, meperidine, pentazocine, dextromoramide, dipipanone, and amitriptyline.

Any of the compositions described herein can be formulated as a liquid for systemic administration. In some embodiments, the compositions are formulated for intraarterial, intravenous, interlymphatic, intraperitoneal, intrathecal, ocular, nasal, intramuscular, intraductal, or subcutaneous administration.

In some embodiments, the compositions are formulated as a solid. In some embodiments, the compositions are formulated for oral or topical (e.g., transdermal) administration. In some embodiments, the compositions are formulated as a suppository.

In some embodiments, the compositions are encapsulated in nanomaterials for targeted delivery (e.g., encapsulated in a nanomaterial having one or more tissue- or cell-targeting molecules on its surface). For example, the compositions can be encapsulated in nanomaterials with one or more molecules on its outer surface that target endothelial cells (e.g., molecules targeting ICAM-1, VCAM-1, E-selectin, P-selectin, or RGD tripeptide, or any of the target endothelial molecules described in Kowalski et al., *IUMBM Life* 63:648-658, 2011). In some embodiments, the compositions are formulated as an emulsion or as a liposome-containing composition. In some embodiments, the compositions are formulated for sustained release (e.g., formulated in a biodegradable polymers or in nanoparticles). In some embodiments, the compositions are formulated in an implantable device that allows for sustained release of the oligonucleotide that decreases the expression of Map4k4 mRNA in a mammalian endothelial cell and/or a cholesterol-improving therapeutic agent.

Pharmaceutical compositions are formulated to be compatible with their intended route of administration or the intended target tissue, e.g., systemic or local administration. In some embodiments, the composition is delivered to an inflamed tissue in the mammal (e.g., by intramuscular, subcutaneous, intraperitoneal, or intrathecal injection) or a blood or lymph vessel (e.g., intraarterial, intravenous, or intralymphatic administration). In some embodiments, the compositions are formulated for oral, intravenous, intradermal, subcutaneous, transmucosal (e.g., nasal sprays are formulated for inhalation), or transdermal (e.g., topical ointments, salves, gels, patches, or creams as generally known in the art) administration. The compositions can include a sterile diluent (e.g., sterile water or saline), a fixed oil, polyethylene glycol, glycerine, propylene glycol, or other synthetic solvents; antibacterial or antifungal agents, such as benzyl alcohol or methyl parabens, chlorobutanol, phenol, ascorbic acid, thimerosal, and the like; antioxidants, such as ascorbic acid or sodium bisulfite; chelating agents, such as ethylenediaminetetraacetic acid; buffers such as acetates, citrates, or phosphates; and isotonic agents, such as sugars (e.g., dextrose), polyalcohols (e.g., manitol or sorbitol), or salts (e.g., sodium chloride). Liposomal suspensions can also be used as pharmaceutically acceptable carriers (see, e.g., U.S. Pat. No. 4,522,811; herein incorporated by reference). Preparations of the compositions can be formulated and enclosed in ampules, disposable syringes, or multiple dose vials that prevent exposure of the caged tamoxifen or caged tamoxifen derivative molecules to light. Where required (as in, for example, injectable formulations), proper fluidity can be maintained by, for example, the use of a coating such as lecithin, or a surfactant. Absorption of an oligonucleotide that decreases the expression of Map4k4 mRNA in an endothelial cell and/or a cholesterol-improving therapeutic agent can be prolonged by including an agent that delays absorption (e.g., aluminum monostearate and gelatin). Alternatively, controlled release can be achieved by implants and microencapsulated delivery systems, which can include biodegradable, biocompatible polymers (e.g., ethylene vinyl acetate, polyanhydrides, polyglycolic acid, collagen, polyorthoesters, and polylactic acid; Alza Corporation and Nova Pharmaceutical, Inc.).

Where oral administration is intended, the agents can be included in pills, capsules, troches and the like, and can contain any of the following ingredients, or compounds of a similar nature: a binder, such as microcrystalline cellulose, gum tragacanth, or gelatin; an excipient, such as starch or lactose; a disintegrating agent, such as alginic acid, Primogel, or corn starch; a lubricant, such as magnesium stearate; a glidant, such as colloidal silicon dioxide; a sweetening agent, such as sucrose or saccharin; or a flavoring agent, such as peppermint, methyl salicylate, or orange flavoring.

The compositions described herein can be formulated for ocular or parenteral (e.g., oral) administration in dosage unit form (i.e., physically discrete units containing a predetermined quantity of active compound for ease of administration and uniformity of dosage). Toxicity and therapeutic efficacy of compositions can be determined by standard pharmaceutical procedures in cell cultures or experimental animals. One can, for example, determine the LD50 (the dose lethal to 50% of the population) and the ED50 (the dose therapeutically effective in 50% of the population), the therapeutic index being the ratio of LD50:ED50. Compositions that exhibit high therapeutic indices are preferred. Where a composition exhibits an undesirable side effect, care should be taken to target the composition to the site of the affected or targeted tissue (the aim being to minimize potential damage to unaffected cells and, thereby, reduce side effects). Toxicity and therapeutic efficacy can be determined by other standard pharmaceutical procedures.

In some embodiments, the compositions described herein are formulated in a single dosage form. In some embodiments, a single dosage of the composition contains between 1 mg to 500 mg, between 1 mg and 400 mg, between 1 mg and 300 mg, between 1 mg and 250 mg, between 1 mg and 200 mg, between 1 mg and 100 mg, and between 1 mg and 50 mg of an oligonucleotide that decreases the expression of Map4k4 mRNA in an endothelial cell.

In some embodiments, a single dosage of the composition contains between 1 mg to 500 mg, between 1 mg and 400 mg, between 1 mg and 300 mg, between 1 mg and 250 mg, between 1 mg and 200 mg, between 1 mg and 100 mg, and between 1 mg and 50 mg of an anti-inflammatory agent and/or between 1 mg to 500 mg, between 1 mg and 400 mg, between 1 mg and 300 mg, between 1 mg and 250 mg, between 1 mg and 200 mg, between 1 mg and 100 mg, and between 1 mg and 50 mg (each) of one or more of a cholesterol-improving therapeutic agent, a fibrate, a nicotinic acid, a bile acid sequestrant, an omega-3 oil supplement, and/or an anti-platelet drug or blood thinner.

Also provided herein are kits that contain at least one dose of any of the compositions described herein. In some embodiments, the kits can further include an item for use in administering a composition (e.g., any of the compositions described herein) to the mammal (e.g., a syringe, e.g., a pre-filled syringe). In some embodiments, the kits contain one or more doses (e.g., at least two, three, four, five, six, seven, eight, nine, ten, eleven, twelve, thirteen, fourteen, twenty, thirty, or forty doses) (e.g., oral or subcutaneous doses) of any of the compositions described herein. In some embodiments, the kit further contains instructions for administering the composition (or a dose of the composition) to a mammal (e.g., a mammal having inflammation or any of the inflammatory disorders or vessel fluid leakage disorders described herein). In some embodiments, the kits contain a composition containing at least one oligonucleotide that decreases the expression of Map4k4 mRNA in an endothelial cell (e.g., any of the oligonucleotides described herein), and a composition containing at least one of a cholesterol-improving therapeutic agent (e.g., any of the cholesterol-improving agents described herein), a fibrate, a nicotinic acid, a bile acid sequestrant, a omega-3 oil supplement, and/or an anti-platelet drug or blood thinner. In some embodiments, the kit further contains instructions for performing any of the methods described herein.

Screening Methods

Also provided herein are methods of identifying a candidate agent useful for decreasing leukocyte extravasation from a lymph or blood vessel into a tissue in a mammal or decreasing fluid leakage from a lymph or blood vessel in a mammal. These methods include providing a mammalian (e.g., human) endothelial cell, contacting the mammalian endothelial cell with a candidate agent, determining a test level of Map4k4 expression in the mammalian endothelial cell, comparing the test level of Map4k4 expression in the mammalian (e.g., human) endothelial cell to a reference level of Map4k4 expression in a control mammalian (e.g., human) endothelial cell untreated with the candidate agent, and identifying a candidate agent that results in a test level of Map4k4 expression that is lower than the reference level of Map4k4 expression as being useful for decreasing leukocyte extravasation or fluid leakage from a lymph or blood vessel into a tissue in a mammal.

In some embodiments, the mammalian (e.g., human) endothelial cell is in vitro. Some embodiments where the mammalian endothelial cell is in vitro further include administering the selected candidate agent to an animal model of inflammation (e.g., any of the animal models of inflammation described herein or known in the art), an animal model of an inflammatory disorder (e.g., any of the animal models of an inflammatory disorder described herein or known in the art), or an animal model of a vessel fluid leakage disorder (e.g., any of the animal models of a vessel fluid leakage disorder described herein or known in the art).

Non-limiting examples of animal models of inflammation are described in Stevenson et al., In Vivo Models of Inflammation, Birkhauser Verlag, Boston, Mass., 2006. Non-limiting examples of animal models of inflammatory disorders are described in Getz et al., *Arteriosclerosis, Thrombosis, and Vascular Biol.* 32:1104-1115, 2012; and Dixon, Springer Seminars in Immunnopathol. 14:103-104, 1992. Non-limiting examples of animal models of vessel fluid leakage disorders are described in Kanter et al., *Plast. Reconstr. Surg.* 85:573-580, 1990; and Henriques et al., *Braz. J. Med. Bio. Res.* 20:243-249, 1987.

In some embodiments, the mammalian endothelial cell is in a mammal, and the contacting is performed by administering the candidate agent to the mammal (e.g., by oral, subcutaneous, intravenous, intraarterial, intraperitoneal, intramuscular, interlymphatic, or intrathecal administration).

In some embodiments, the test level and the reference level of Map4k4 expression is a level of Map4k4 protein (e.g., SEQ ID NO: 1, 3, 5, 7, or 9). In some embodiments, the test level and the reference level of Map4k4 expression is a level of Map4k4 mRNA (mRNA encoding Map4k4 protein, e.g., SEQ ID NO: 2, 4, 6, 8, or 10).

In some embodiments, the reference level of Map4k4 expression is a level of Map4k4 expression of a control, in vitro, mammalian endothelial cell untreated with the candidate agent. In some embodiments, the reference level of Map4k4 expression is a level of Map4k4 expression of a control in vivo mammalian endothelial cell untreated with the candidate agent.

Methods for determining the level of Map4k4 protein expression are known in the art. For example, levels of Map4k4 protein expression can be determined using an antibody or an antigen-binding antibody fragment that binds to a Map4k4 protein (e.g., anti-MAP4K4 antibody from Abcam, Cambridge, Mass.; and MAP4K4 antibody from Epitomics, Burlingame, Calif.). In some embodiments, the amount of Map4k4 protein expression can be determined using an antibody or antigen-binding antibody fragment that binds to Map4k4 protein in an enzyme-linked immunosorbent assay (ELISA).

Methods for determining the level of Map4k4 mRNA expression are also known in the art. For example, levels of Map4k4 mRNA expression can be determined using polymerase chain reaction (PCR) techniques, including reverse transcriptase (RT)-PCR and real-time RT-PCR using primers that are complementary to a Map4k4 mRNA (see, e.g., the exemplary Map4k4 mRNAs described herein, e.g., SEQ ID NO: 2, 4, 6, 8, or 10). Additional sequences for mammalian Map4k4 mRNAs are known in the art.

Some embodiments of these methods further include generating a pharmaceutical composition for treating inflammation or treating an inflammatory disease or a vessel leakage disorder that includes the candidate agent.

The invention is further described in the following examples, which do not limit the scope of the invention described in the claims.

EXAMPLES

Example 1

Map4k4 Regulates the Expression of Leukocyte Adhesion Molecules in Endothelial Cells Experiments to study the effect of Map4k4 activity on the expression of leukocyte adhesion molecules in endothelial cells were performed using human umbilical vein endothelial cells (HUVECs). In a first set of experiments, HUVECs were treated with 10 ng/mL TNFα for up to 60 minutes, and the expression and activity of Map4k4 was determined in lysates from the treated cells. The data show that 10 ng/mL TNFα induces Map4k4 activity in endothelial cells within 60 minutes (FIG. 1).

Figure 2:
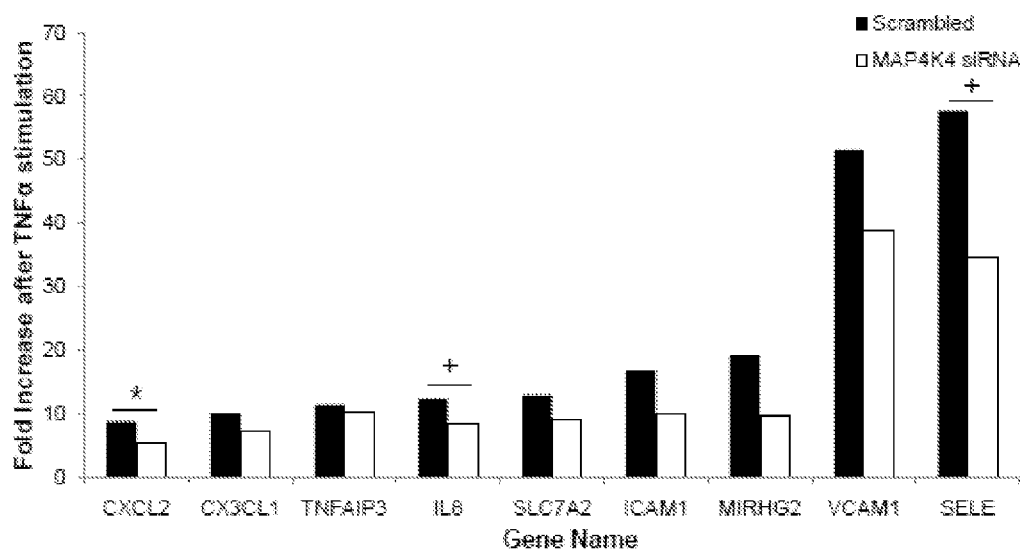
FIG. 2 is a graph showing the fold-increase in the mRNA levels of different genes in HUVECs transfected with 25 nM scrambled or Map4k4 siRNA, following treatment with 10 ng/mL TNFα as compared to the same cells untreated with TNFα.
Figure 3:
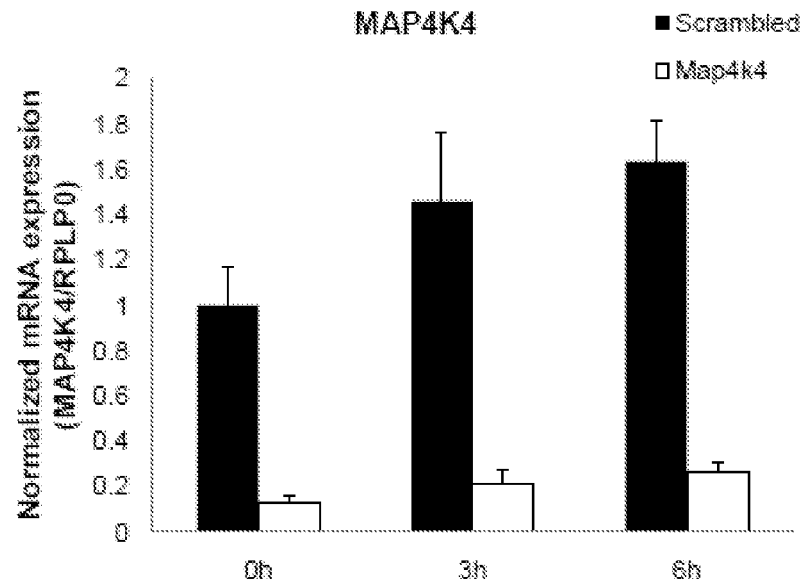
FIG. 3 is a graph showing the normalized level of Map4k4 mRNA expression in HUVECs transfected with 25 nM scrambled or Map4k4 siRNA, following no treatment with TNFα or treatment with 10 ng/mL TNFα for 3 or 6 hours.
Figure 4:
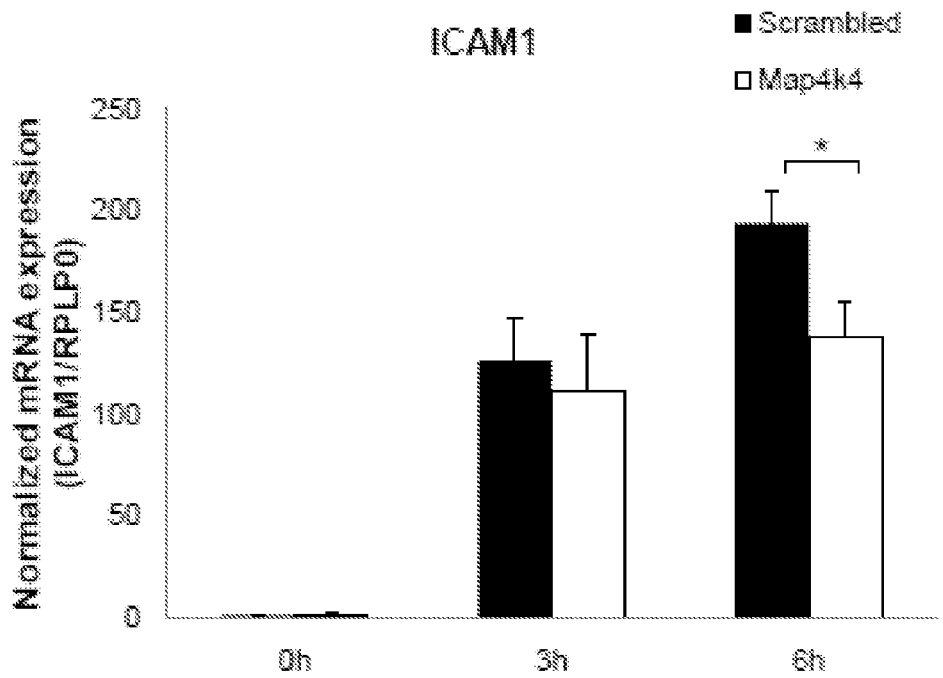
FIG. 4 is a graph showing the normalized level of ICAM-1 mRNA expression in HUVECs transfected with 25 nM scrambled or Map4k4 siRNA, following no treatment with TNFα or treatment with 10 ng/mL TNFα for 3 or 6 hours.
Figure 5:
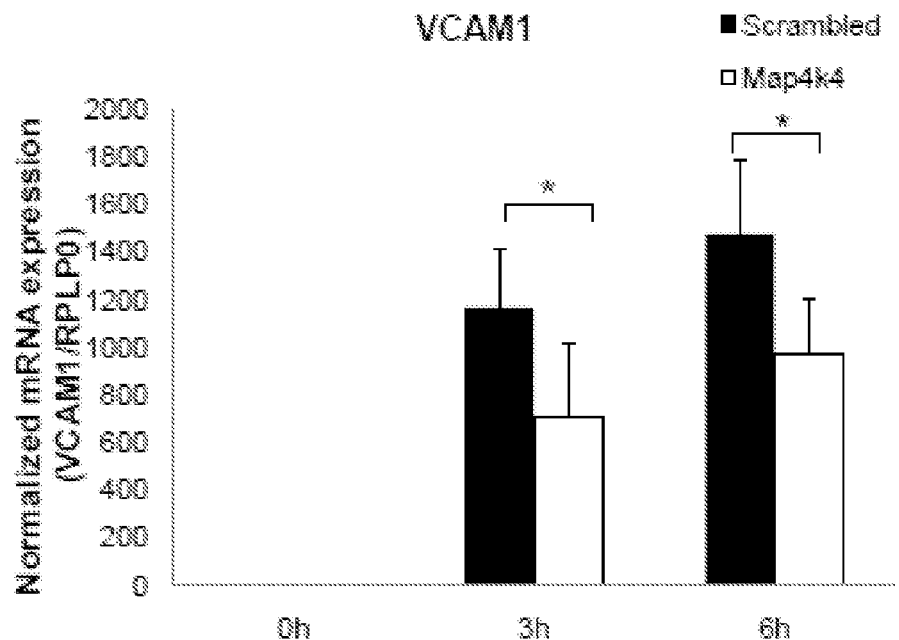
FIG. 5 is a graph showing the normalized level of VCAM-1 mRNA expression in HUVECs transfected with 25 nM scrambled or Map4k4 siRNA, following no treatment with TNFα or treatment with 10 ng/mL TNFα for 3 or 6 hours.
Figure 6:
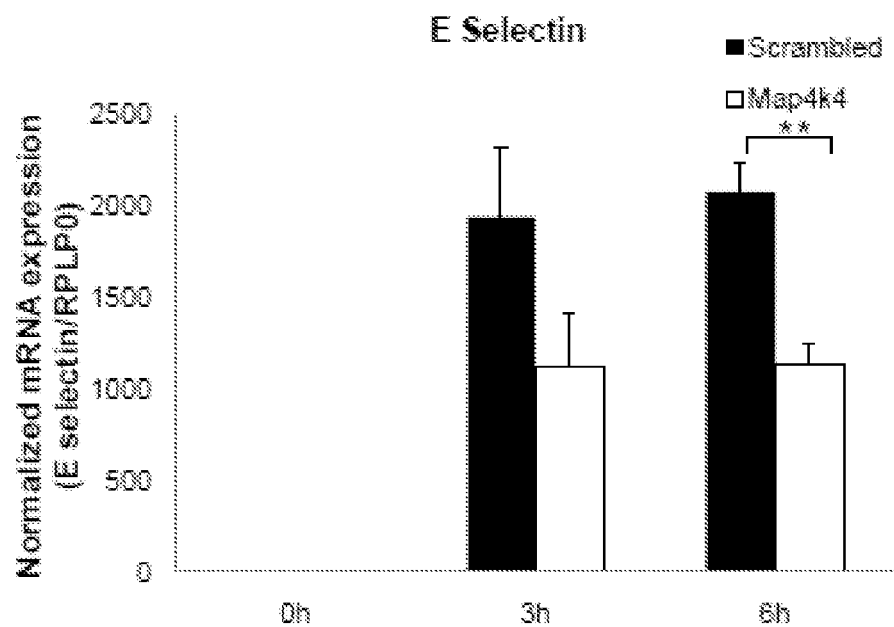
FIG. 6 is a graph showing the normalized level of E-selectin mRNA expression in HUVECs transfected with 25 nM scrambled or Map4k4 siRNA, following no treatment with TNFα or treatment with 10 ng/mL TNFα for 3 or 6 hours.
Figure 7:
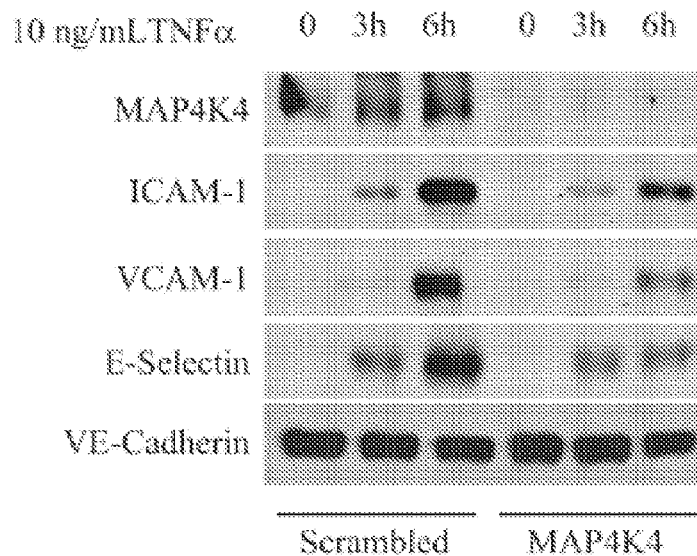
FIG. 7 is an immunoblot showing the level of Map4k4, ICAM-1, VCAM-1, E-selectin, and VE-cadherin protein expression in HUVECs transfected with 25 nM scrambled or Map4k4 siRNA, following no treatment with TNFα or treatment with 10 ng/mL TNFα for 3 or 6 hours.
Figure 8:
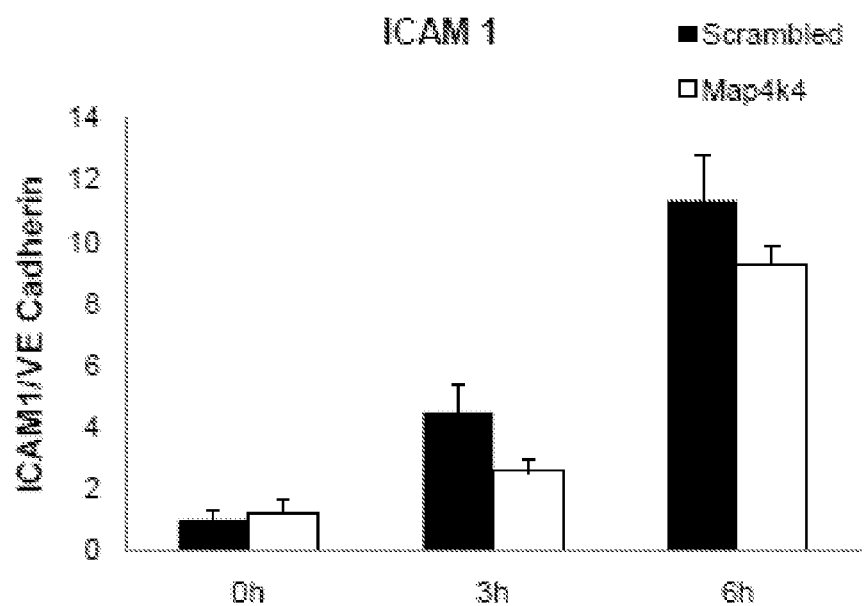
FIG. 8 is a graph showing the normalized level of ICAM-1 protein expression in HUVECs transfected with 25 nM scrambled or Map4k4 siRNA, following no treatment or treatment with 10 ng/mL TNFα for 3 or 6 hours.
Figure 9:
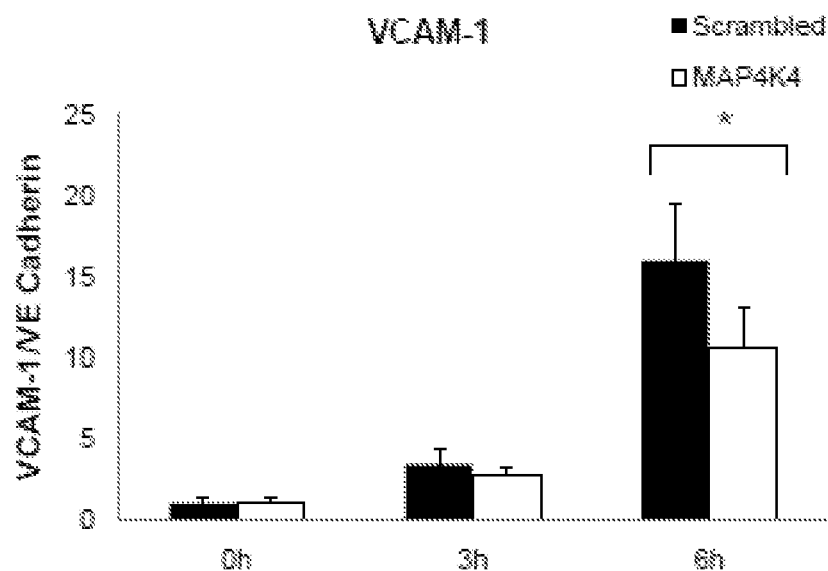
FIG. 9 is a graph showing the normalized level of VCAM-1 protein expression in HUVECs transfected with 25 nM scrambled or Map4k4 siRNA, following no treatment or treatment with 10 ng/mL TNFα for 3 or 6 hours.
Figure 10:
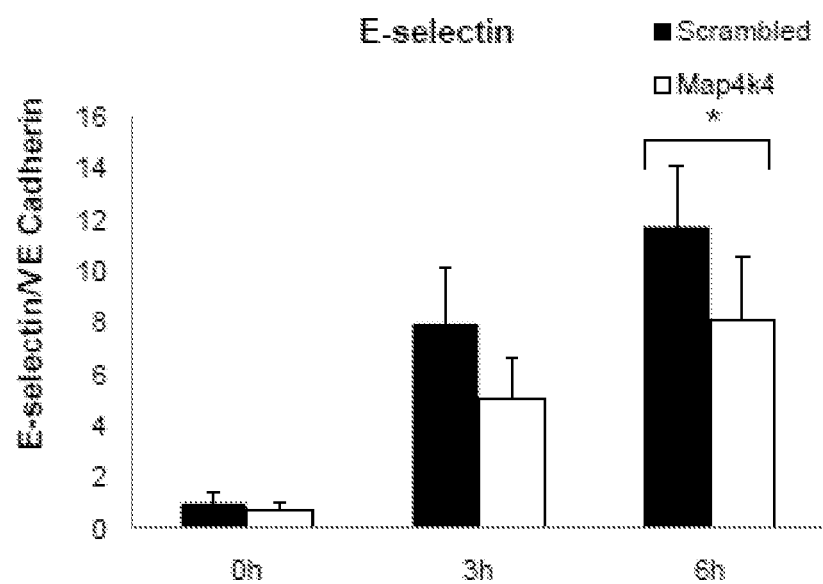
FIG. 10 is a graph showing the normalized level of E-selectin protein expression in HUVECs transfected with 25 nM scrambled or Map4k4 siRNA, following no treatment or treatment with 10 ng/mL TNFα for 3 or 6 hours.

A further set of experiments was performed to determine whether Map4k4 expression has an effect on TNFα-mediated gene expression in endothelial cells. In these experiments, HUVECs were transfected with 25 nM of a scrambled (CAGTCGCGTTTGCGACTGGTT; SEQ ID NO: 24) or Map4k4 (GACCAACTCTGGCTTGTTATT; SEQ ID NO: 19) siRNA (purchased from Dharmacon), and were either left untreated or treated with 10 ng/mL TNFα for 3 or 6 hours. The data show that Map4k4 mediates the TNFα-induced expression of CXCL2, CX3CL1, TNFAIP3, IL-8, SLC7A2, ICAM-1, MIRHG2, VCAM-1, and E-selectin in endothelial cells (FIG. 2). Additional experiments were performed to check the effect of Map4k4 siRNA on TNFα-induced Map4k4, ICAM-1, VCAM-1, and E-selectin mRNA expression. The data from these experiments show that Map4k4 siRNA effectively reduces Map4k4 mRNA expression in HUVECs (control data shown in FIG. 3), and that Map4k4 mediates the TNFα-induced increase in ICAM-1, VCAM-1, and E-selectin mRNA expression in endothelial cells (see, FIGS. 4-6).

The effect of Map4k4 on the TNFα-induced stimulation of ICAM-1, VCAM-1, and E-selectin protein expression in HUVECs was also studied. In these experiments, HUVECs were again transfected with either 25 nM of scrambled or Map4k4 siRNA, and were left untreated or treated with 10 ng/mL TNFα for 3 or 6 hours. The data from these experiments show that Map4k4 mediates the TNFα-induced increase in ICAM-1, VCAM-1, and E-selectin protein expression in endothelial cells (see, FIGS. 7-10).

Figure 11:
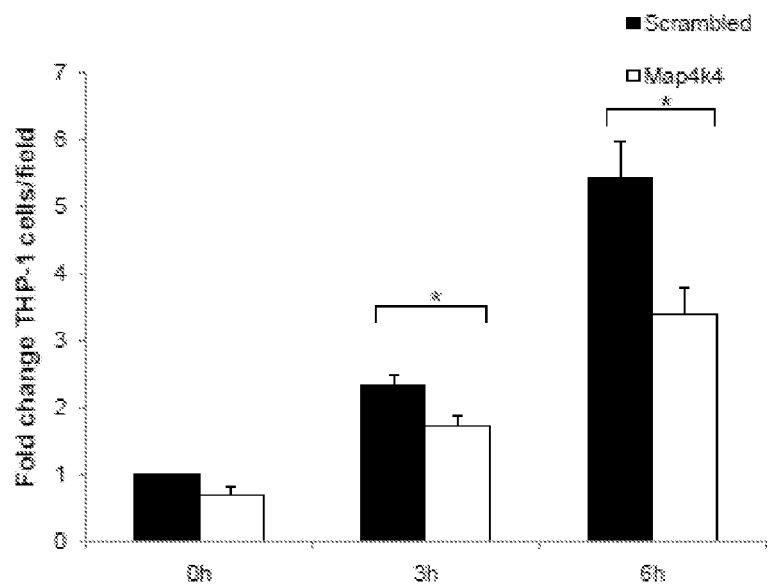
FIG. 11 is a graph showing the fold change in the adhesion of THP-1 monocytes, a monocyte cell line that can differentiate into macrophage-like cells, to HUVECs transfected with 25 nM scrambled or Map4k4 siRNA, following no treatment or treatment with 10 ng/mL TNFα for 3 or 6 hours (relative to the level of adhesion of THP-1 monocytes to HUVECs transfected with 25 nM scrambled siRNA, and not treated with TNFα).

The above data show that an agent that decreases the expression of Map4k4 mRNA in endothelial cells can prevent the expression of leukocyte adhesion molecules on the surface of endothelial cells, and that such an agent may decrease the binding of leukocytes (e.g., monocytes) to endothelial cells exposed to inflammatory stimuli. An additional set of experiments was performed to determine whether decreasing Map4k4 expression would decrease the amount of TNFα-induced monocyte binding to endothelial cells. In these experiments, HUVECs were transfected with 25 nM scrambled or Map4k4 siRNA, left untreated or treated with 10 ng/mL TNFα for 3 or 6 hours, and then contacted with calcein AM-labeled THP-1 monocytes for 30 minutes at 37° C. The endothelial cells were then washed and the number of adherent monocytes were imaged using fluorescent microscopy. The data show that endothelial cells with decreased Map4k4 expression demonstrated a significant decrease in the ability to bind monocytes (FIG. 11).

Example 2

Figure 12:
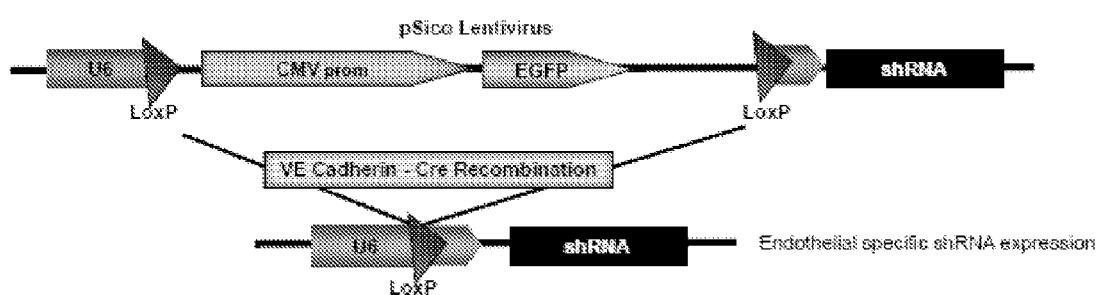
FIG. 12 is a schematic showing the construct used to generate mice with reduced endothelial cell Map4k4 expression (endothelial Map4k4 knock-down mice).

Endothelial Map4k4 Knock-Down Mice Demonstrate Decreased Leukocyte Adhesion Molecule Expression in Endothelial Cells Endothelial Map4k4 knock-down mice were generated to further study the effect of Map4k4 expression and activity on leukocyte adhesion molecule expression in endothelial cells. The endothelial Map4k4 knock-down mice were generated by crossing Cg-Tg (Cdh5-cre) 7Mlia/J (VE Cadherin-Cre) mice (The Jackson Laboratory, Bar Harbor, Me.) with shMap4k4 mice (genetic constructs shown in FIG. 12). In a first set of experiments, primary lung endothelial cells and primary lung fibroblasts were isolated from control (Map4k4 sh) and the endothelial Map4k4 knock-down (Map4k4 sh-cre) mice, and the levels of Map4k4 mRNA were assessed using quantitative RT-PCR.

Figure 13:
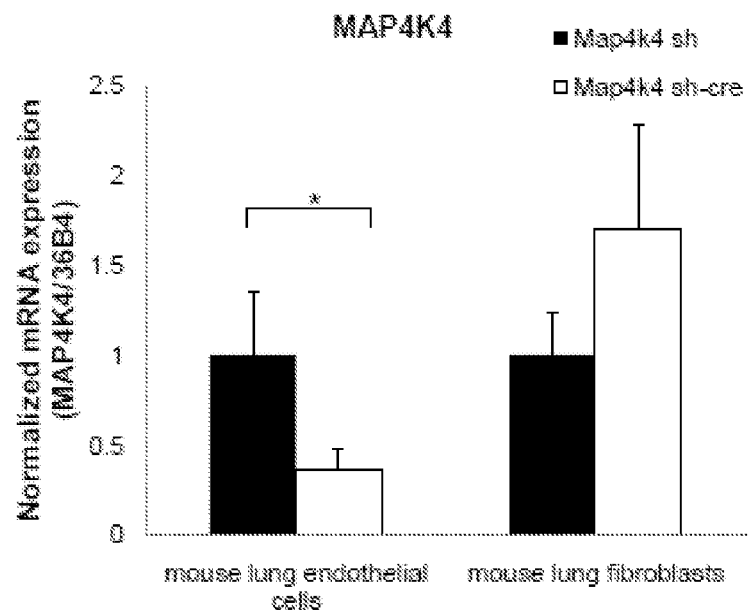
FIG. 13 shows the normalized level of Map4k4 mRNA expression in primary mouse lung endothelial cells and primary mouse lung fibroblasts isolated from control (a mouse containing a control transgene in which the shRNA that decreases Map4k4 expression is not expressed) and endothelial Map4k4 knock-down mice.
Figure 14:
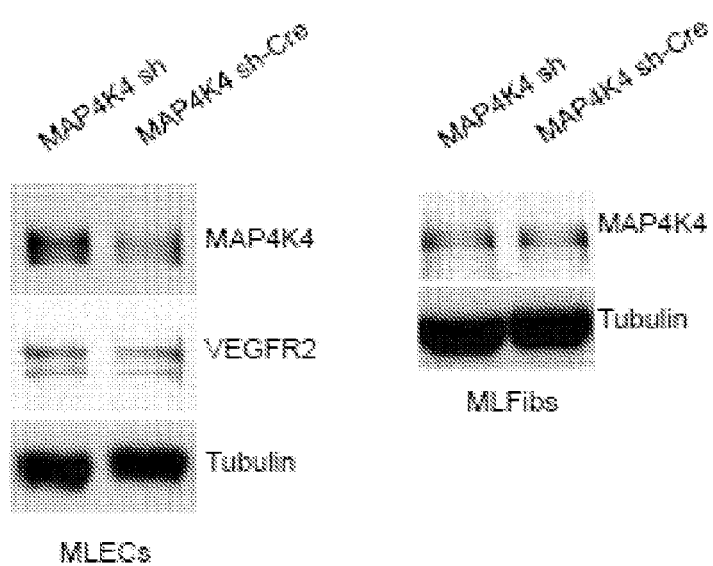
FIG. 14 is a Western blot showing the levels of Map4k4, VEGFR2, and tubulin protein expression in primary mouse lung endothelial cells and primary mouse lung fibroblasts isolated from control and endothelial Map4k4 knock-down mice.
Figure 15:
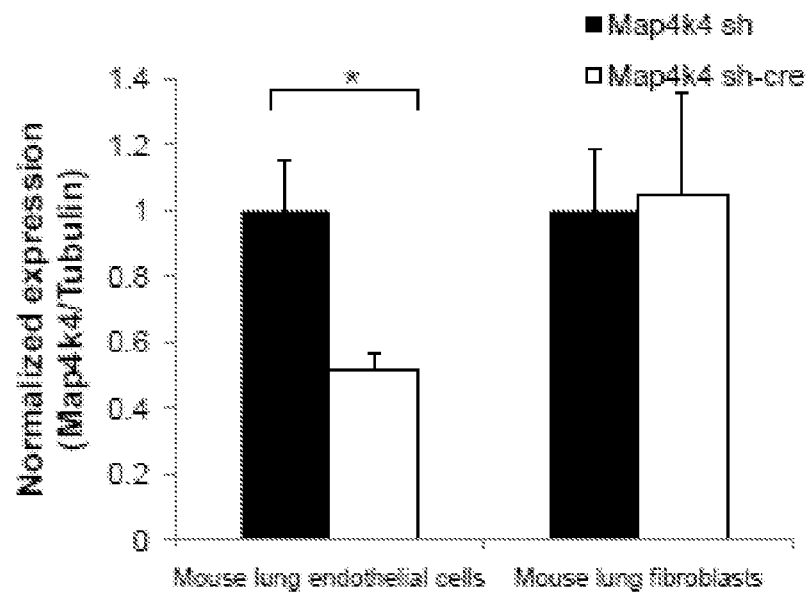
FIG. 15 is a graph showing the normalized levels of Map4k4 protein expression in primary mouse lung endothelial cells and primary mouse lung fibroblasts isolated from control and endothelial Map4k4 knock-down mice.
Figure 16:
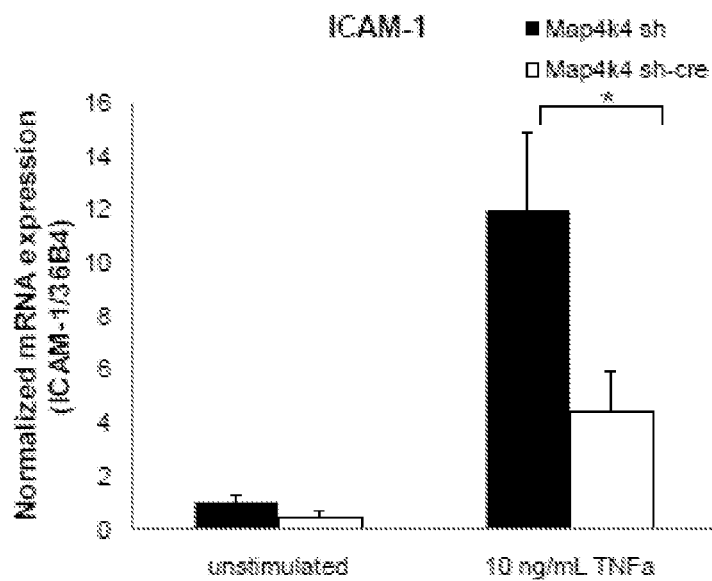
FIG. 16 is a graph showing the normalized level of ICAM-1 mRNA expression in primary mouse lung endothelial cells isolated from control and endothelial Map4k4 knock-down mice following no treatment or treatment with 10 ng/mL TNFα for 6 hours.
Figure 17:
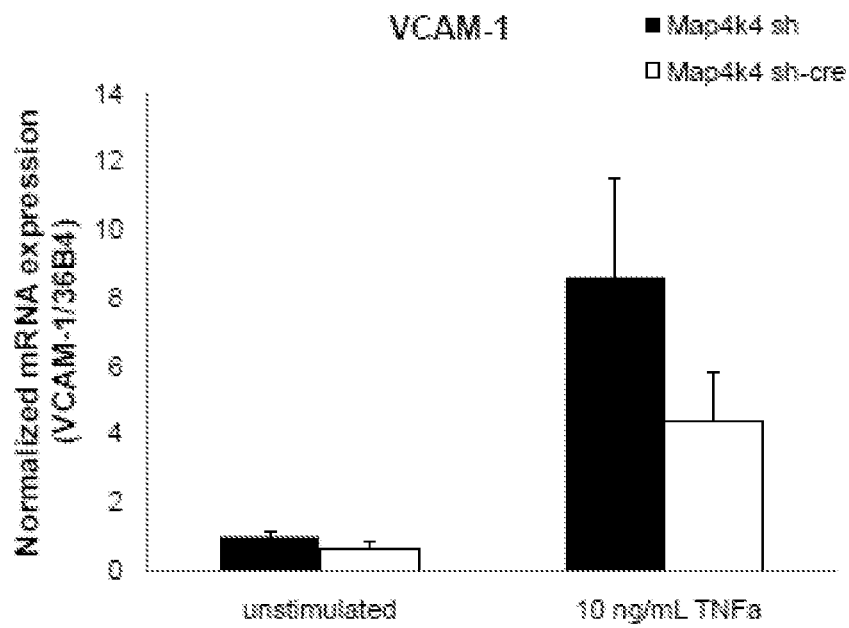
FIG. 17 is a graph showing the normalized level of VCAM-1 mRNA expression in primary mouse lung endothelial cells isolated from control and endothelial Map4k4 knock-down mice following no treatment or treatment with 10 ng/mL TNFα for 6 hours.
Figure 18:
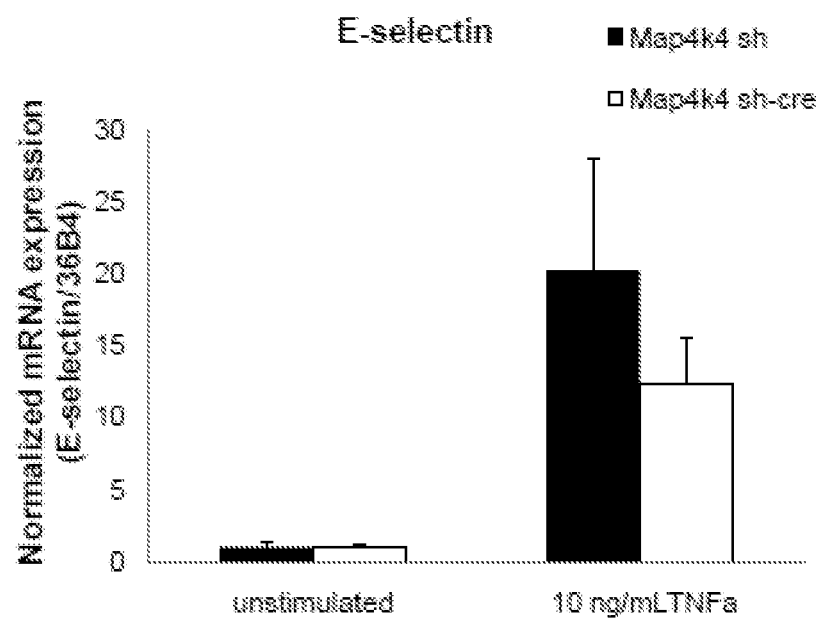
FIG. 18 is a graph showing the normalized level of E-selectin mRNA expression in primary mouse lung endothelial cells isolated from control and endothelial Map4k4 knock-down mice following no treatment or treatment with 10 ng/mL TNFα for 6 hours.
Figure 19:
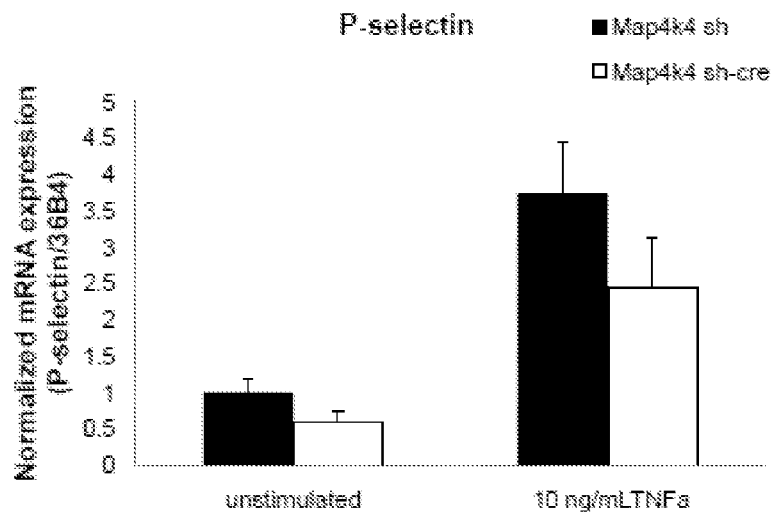
FIG. 19 is a graph showing the normalized level of P-selectin mRNA expression in primary mouse lung endothelial cells isolated from control and endothelial Map4k4 knock-down mice following no treatment or treatment with 10 ng/mL TNFα for 6 hours.

The data show that Map4k4 mRNA levels were significantly decreased in the lung endothelial cells of the endothelial Map4k4 knock-down mice (FIG. 13). The expression levels of Map4k4 protein in primary lung endothelial cells and primary lung fibroblasts in control (Map4k4 sh) and endothelial Map4k4 knock-down (Map4k4 sh-cre) mice were also assessed by performing Western blots. The data from these experiments show that Map4k4 protein is also decreased in primary lung endothelial cells from the endothelial Map4k4 knock-down mice (FIGS. 14 and 15).

A further set of experiments was performed to study the expression of leukocyte adhesion molecules in primary lung endothelial cells from the endothelial Map4k4 knock-down mice. In these experiments, primary lung endothelial cells from the control (Map4k4 sh) and the endothelial Map4k4 knock-down mice (Map4k4 sh-cre) were left untreated or were treated with 10 ng/mL TNFα for 6 hours, and the expression levels of ICAM-1, VCAM-1, E-selectin, and P-selectin mRNA was assessed using quantitative RT-PCR. The data from these experiments show that the TNFα-induction of ICAM-1, VCAM-1, E-selectin, and P-selectin was significantly decreased in lung primary endothelial cells from the endothelial Map4k4 knockout mice (see, FIGS. 16-19, respectively).

These data indicate that Map4k4 expression and activity play a role in mediating an increase in the expression of several leukocyte adhesion molecules in mammalian endothelial cells in response to inflammatory stimuli.

Example 3

The Role of Map4k4 in the Permeability of Endothelial Cell Monolayers

Figure 20:
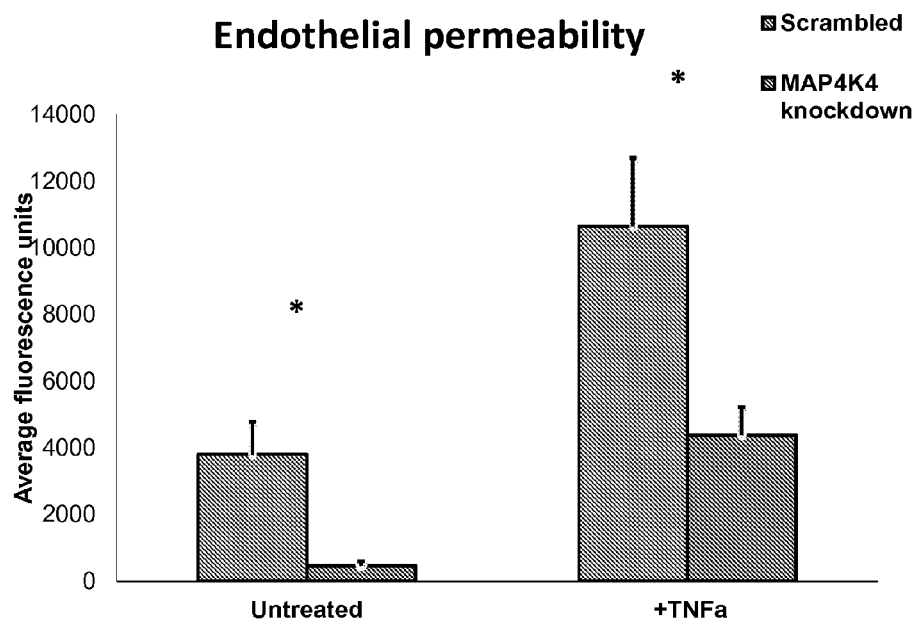
FIG. 20 is a graph showing the migration of FITC-labeled dextran (average fluorescence units) through a monolayer of HUVECs transfected with 25 nM scrambled or Map4k4 siRNA, following no treatment or overnight treatment with 10 ng/mL TNFα.

A set of experiments was performed to investigate the role of Map4k4 expression and activity in the permeability of endothelial cell monolayers. In these experiments, HUVECs were transfected with 25 nM scrambled or Map4k4 siRNA, seeded onto porous collagen-coated Transwell chambers, and allowed to grow into a confluent monolayer for 72 hours. Once the HUVEC cells had reached confluence, they were left untreated or were treated overnight with 10 ng/mL TNFα. After TNFα treatment, FITC-labeled dextran was added to the upper chamber of the Transwell apparatus, and the amount of labeled dextran present in the bottom chamber was measured after 20 minutes using a fluorescent plate reader. The data from these experiments show that a decrease in Map4k4 expression decreases the permeability of an epithelial cell monolayer (FIG. 20). These data indicate that an agent that decreases the expression of Map4k4 mRNA in an endothelial cell would decrease fluid leakage from a blood or lymph vessel lined with endothelial cells.

Example 4

The Role of Endothelial Map4k4 Expression in Glucose Tolerance

Figure 21:
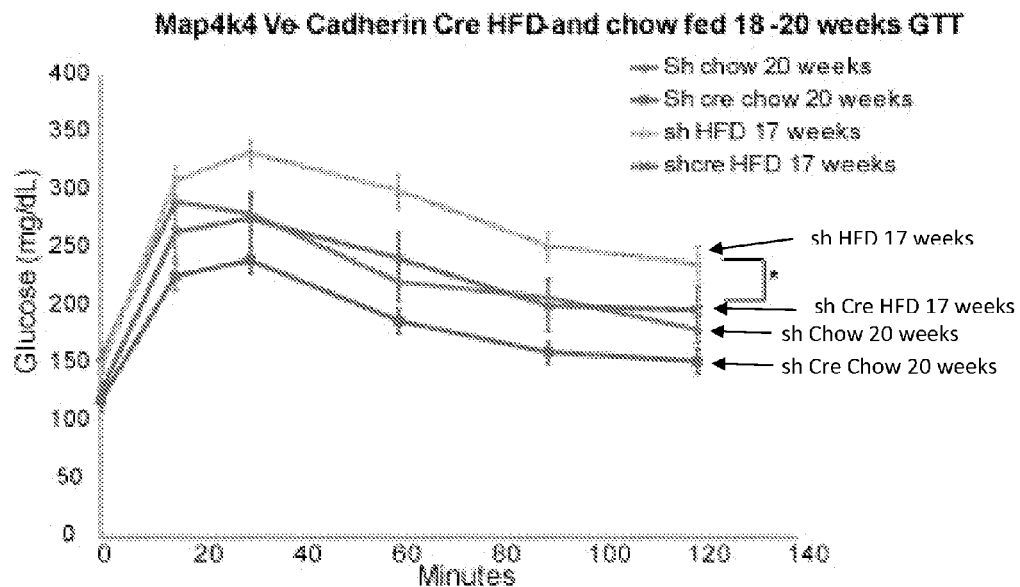
FIG. 21 is a graph showing the glucose levels in control (Sh) and endothelial Map4k4 knock-down (Sh cre) mice following a chow or a high fat diet (HFD) for 17 weeks (post-weaning), fasting overnight, and injection with 1 g/kg glucose. The data shown are the glucose levels in the control and endothelial knock-down mice at 0, 15, 30, 60, 90, and 120 minutes after injection with 1 g/kg glucose. The data represent the mean±standard error of the mean (n=6-11). The area under the curve was quantitated in Graph Pad Prism and subjected to student's t-test. The asterisk represents $p<0.05$.

A further set of experiments were performed to study the effect of endothelial cell Map4k4 expression on glucose tolerance in mice. In these experiments, control and the endothelial Map4k4 knock-down mice were fed a chow or high fat diet (HFD) for 17 days (post-weaning), fasted overnight, and then intraperitoneally injected with 1 g/kg D-glucose. Blood glucose levels were then determined in the mice at 0, 15, 30, 60, 90, and 120 minutes after injection. The data show that the endothelial Map4k4 knock-down mice demonstrated greater glucose tolerance than control mice placed on the same diet (chow or high fat diet) (FIG. 21). These data indicate that Map4k4 expression in endothelial cells plays a role in glucose metabolism and uptake pathways, and an oligonucleotide that decreases the expression of Map4k4 mRNA in an endothelial cell can be used to improve (increase) glucose tolerance in a mammal (e.g., a human, such as a human having type I or type II diabetes).

Example 5

The Role of Map4k4 in the Formation of Atherosclerotic Plaques

Figure 22:
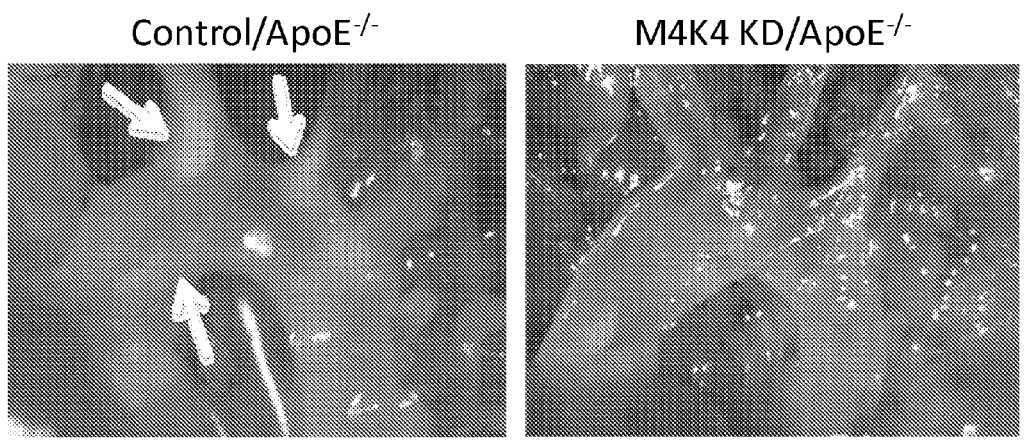
FIG. 22 is a light microscope image of an aorta from a ApoE$^{-/-}$ (control) mouse (left image) and a light microscope image of an aorta from a ApoE$^{-/-}$/Map4k4 knock-down mice (right image) that were fed a Western diet for 8 weeks. The arrows indicate atherosclerotic plaques.
Figure 23:
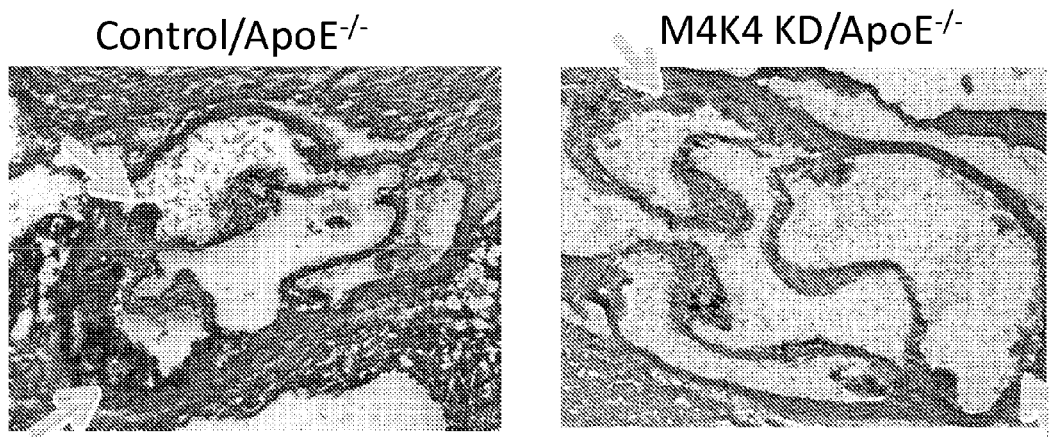
FIG. 23 is an Oil-Red O-stained aortic root section from a ApoE$^{-/-}$ (control) mouse (left panel) and an Oil-Red-O-stained aortic root section from a ApoE$^{-/-}$/Map4k4 knock-down mouse (right panel) that were fed a Western diet for 8 weeks. The arrows indicate atherosclerotic plaques.
Figure 24:
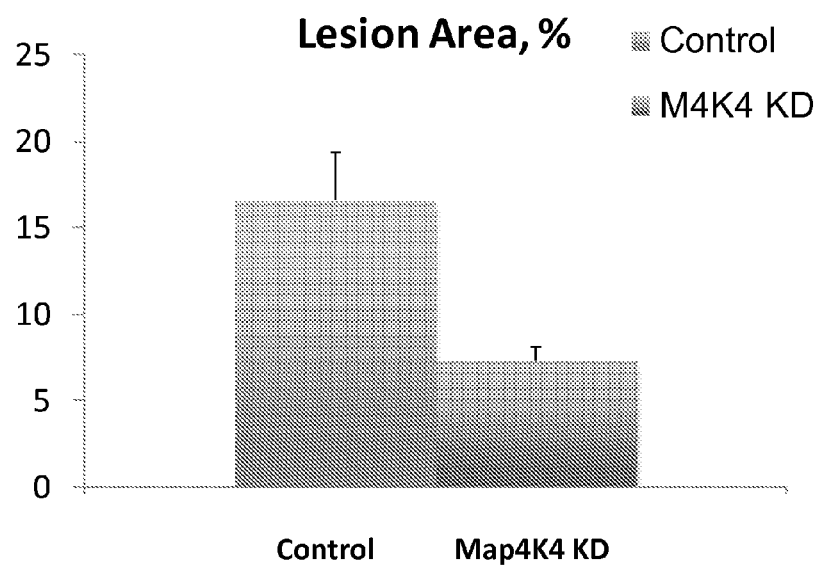
FIG. 24 is a graph showing the mean percentage aortic root area of atherosclerotic lesions (plaques) present in ApoE$^{-/-}$ (control) mice and ApoE$^{-/-}$/Map4k4 known-down mice that were fed a Western diet for 8 weeks, as determined using Oil-Red-O staining and ImageJ software. The mean data are shown (n=3), with a $p<0.05$ (*).
Figure 25:
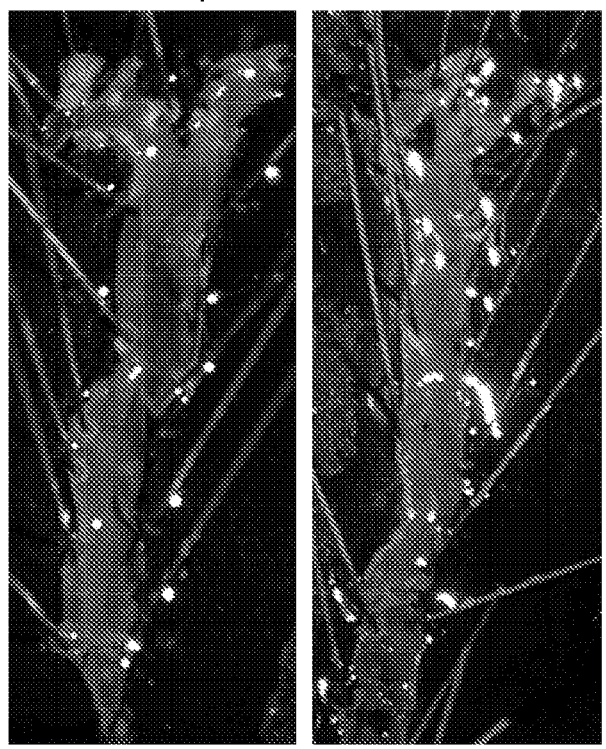
FIG. 25 is a light microscope en face image of an aorta stained with Oil-Red-O from an ApoE$^{-/-}$ (control) mouse (left image) and a light microscope en face image of an aorta stained with Oil-Red-O from an ApoE$^{-/-}$/Map4k4 known-down mouse (right image) that were fed a Western diet for 8 weeks.
Figure 26:
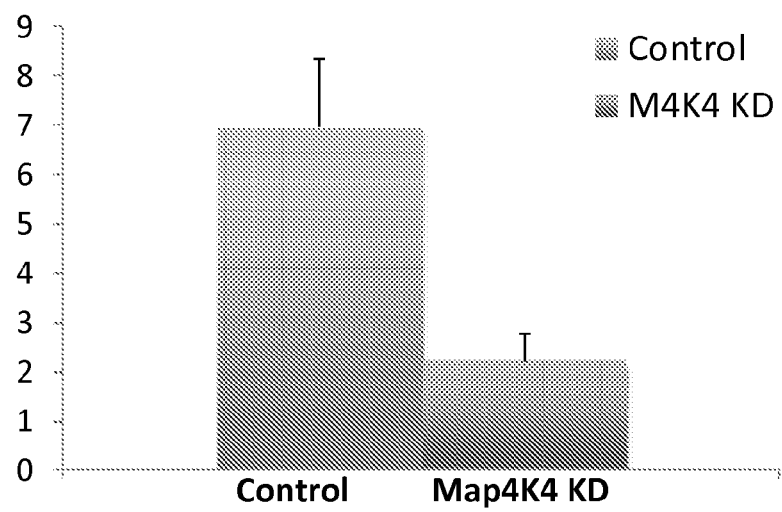
FIG. 26 is a graph showing the mean percentage aortic root area of atherosclerotic lesions (plaques) present in the en face light microscope images from ApoE$^{-/-}$ (control) mice or ApoE$^{-/-}$/Map4k4 known-down mice that were fed a Western diet for 8 weeks, as determined using Oil-Red-O staining and ImageJ software. The mean data are shown (n=5-6), with a $p<0.05$ (*).

Experiments were performed to study the effect of endothelial cell Map4k4 expression on the formation of atherosclerotic plaques in blood vessels in mice. In these experiments, control ApoE-/- mice or ApoE-/-/Map4k4 knock-down mice were fed a Western diet for 8 weeks. The mice were then euthanized, and their aortas examined using light microscopy. Light microscopic images indicate that the aorta of a control ApoE-/- mouse had more atherosclerotic plaques (lesions) compared to a ApoE-/-/Map4k4 knock-down mouse (FIG. 22). Light microscopic images of the aortic roots of a control ApoE-/- mouse or an ApoE-/-/Map4k4 knock-down mouse stained with Oil-Red-O also show that the aorta of the control ApoE-/- mouse had an increased number (and size) of atherosclerotic plaques compared to the ApoE-/-/Map4k4 knock-down mouse (FIGS. 23 and 25). The mean percentage of the total aortic root area covered by atherosclerotic plaques (lesions) was also increased in the control ApoE-/- mice as compared to the ApoE-/-/Map4k4 knock-down mice (FIGS. 24 and 26).

These data indicate that administration of an oligonucleotide that decreases the expression of Map4k4 mRNA in an endothelial cell would decrease the formation of atherosclerotic plaques in a mammal, and would also treat atherosclerosis in a mammal.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

The invention claimed is:

1. A method of reducing formation of atherosclerotic plaques in a blood vessel in a mammal, the method comprising:
   identifying a mammal having atherosclerosis; and
   administering to the identified subject an oligonucleotide selected from the group consisting of an inhibitory RNA, an antisense oligonucleotide, and a ribozyme that decreases Map4k4 mRNA expression in an endothelial cell, in an amount sufficient to decrease the expression of Map4k4 in an endothelial cell that lines a lumen of a blood vessel in the identified mammal, thereby reducing extravasation of leukocytes from the lumen of the blood vessel and reducing formation of atherosclerotic plaques in the blood vessel in the identified mammal.

2. The method of claim 1, wherein the mammal is a human.

3. A method of treating atherosclerosis in a mammal, the method comprising:
   identifying a mammal having atherosclerosis; and
   administering to the identified mammal an oligonucleotide selected from the group consisting of an inhibitory RNA, an antisense oligonucleotide, and a ribozyme that decreases Map4k4 mRNA expression in an endothelial cell, in an amount sufficient to decrease the expression of Map4k4 in an endothelial cell that lines a lumen of a blood vessel in the identified mammal, thereby reducing extravasation of leukocytes from the lumen of the blood vessel, and treating atherosclerosis in the identified mammal.

4. The method of claim 3, wherein the mammal is a human.

5. The method of claim 1, wherein the oligonucleotide is administered by intravenous or intraarterial administration.

6. The method of claim 1, wherein the oligonucleotide is an inhibitory RNA.

7. The method of claim 6, wherein the inhibitory RNA is a small inhibitory RNA.

8. The method of claim 1, wherein the oligonucleotide is an antisense oligonucleotide.

9. The method of claim 1, wherein the oligonucleotide is a ribozyme.

10. The method of claim 1, further comprising administering to the identified mammal one or more additional agents useful for treating atherosclerosis selected from the group consisting of: an anti-inflammatory agent, an analgesic, a cholesterol-improving therapeutic agent, a fibrate, nicotinic acid, a bile acid sequestrant, an omega-3 oil supplement, an anti-platelet drug, and a blood thinner.

11. The method of claim 3, wherein the oligonucleotide is administered by intravenous or intraarterial administration.

12. The method of claim 3, wherein the oligonucleotide is an inhibitory RNA.

13. The method of claim 12, wherein the inhibitory RNA is a small inhibitory RNA.

14. The method of claim 3, wherein the oligonucleotide is an antisense oligonucleotide.

15. The method of claim 3, wherein the oligonucleotide is a ribozyme.

16. The method of claim 3, further comprising administering to the identified mammal one or more additional agents useful for treating atherosclerosis selected from the group consisting of: an anti-inflammatory agent, an analgesic, a cholesterol-improving therapeutic agent, a fibrate, nicotinic acid, a bile acid sequestrant, an omega-3 oil supplement, an anti-platelet drug, and a blood thinner.

17. A method of treating atherosclerosis in a mammal, the method comprising:
   identifying a mammal having atherosclerosis; and
   administering to the identified mammal an oligonucleotide selected from the group of an oligonucleotide selected from the group consisting of an inhibitory RNA, an antisense oligonucleotide, and a ribozyme that decreases Map4k4 mRNA expression in an endothelial cell, in an amount sufficient to decrease the expression of Map4k4 in an endothelial cell that lines a lumen of a blood vessel in the identified mammal, thereby treating atherosclerosis in the subject.

* * * * *

SEQUENCE LISTING

```
<160> NUMBER OF SEQ ID NOS: 24

<210> SEQ ID NO 1
<211> LENGTH: 1165
<212> TYPE: PRT
<213> ORGANISM: Homo sapiens

<400> SEQUENCE: 1

Met Ala Asn Asp Ser Pro Ala Lys Ser Leu Val Asp Ile Asp Leu Ser
```

```
              1               5              10              15
            Ser Leu Arg Asp Pro Ala Gly Ile Phe Glu Leu Val Glu Val Gly
                         20              25              30
            Asn Gly Thr Tyr Gly Gln Val Tyr Lys Gly Arg His Val Lys Thr Gly
                     35              40              45
            Gln Leu Ala Ala Ile Lys Val Met Asp Val Thr Asp Glu Glu Glu
                 50              55              60
            Glu Ile Lys Leu Glu Ile Asn Met Leu Lys Lys Tyr Ser His His Arg
            65              70              75              80
            Asn Ile Ala Thr Tyr Tyr Gly Ala Phe Ile Lys Lys Ser Pro Pro Gly
                             85              90              95
            His Asp Asp Gln Leu Trp Leu Val Met Glu Phe Cys Gly Ala Gly Ser
                            100             105             110
            Ile Thr Asp Leu Val Lys Asn Thr Lys Gly Asn Thr Leu Lys Glu Asp
                            115             120             125
            Trp Ile Ala Tyr Ile Ser Arg Glu Ile Leu Arg Gly Leu Ala His Leu
                            130             135             140
            His Ile His His Val Ile His Arg Asp Ile Lys Gly Gln Asn Val Leu
            145             150             155             160
            Leu Thr Glu Asn Ala Glu Val Lys Leu Val Asp Phe Gly Val Ser Ala
                            165             170             175
            Gln Leu Asp Arg Thr Val Gly Arg Arg Asn Thr Phe Ile Gly Thr Pro
                            180             185             190
            Tyr Trp Met Ala Pro Glu Val Ile Ala Cys Asp Glu Asn Pro Asp Ala
                            195             200             205
            Thr Tyr Asp Tyr Arg Ser Asp Leu Trp Ser Cys Gly Ile Thr Ala Ile
                    210             215             220
            Glu Met Ala Glu Gly Ala Pro Pro Leu Cys Asp Met His Pro Met Arg
            225             230             235             240
            Ala Leu Phe Leu Ile Pro Arg Asn Pro Pro Arg Leu Lys Ser Lys
                            245             250             255
            Lys Trp Ser Lys Lys Phe Phe Ser Phe Ile Glu Gly Cys Leu Val Lys
                        260             265             270
            Asn Tyr Met Gln Arg Pro Ser Thr Glu Gln Leu Leu Lys His Pro Phe
                        275             280             285
            Ile Arg Asp Gln Pro Asn Glu Arg Gln Val Arg Ile Gln Leu Lys Asp
                        290             295             300
            His Ile Asp Arg Thr Arg Lys Arg Gly Glu Lys Asp Glu Thr Glu
            305             310             315             320
            Tyr Glu Tyr Ser Gly Ser Glu Glu Glu Glu Val Pro Glu Gln
                        325             330             335
            Glu Gly Glu Pro Ser Ser Ile Val Asn Val Pro Gly Glu Ser Thr Leu
                        340             345             350
            Arg Arg Asp Phe Leu Arg Leu Gln Gln Glu Asn Lys Glu Arg Ser Glu
                        355             360             365
            Ala Leu Arg Arg Gln Gln Leu Leu Gln Glu Gln Gln Leu Arg Glu Gln
                    370             375             380
            Glu Glu Tyr Lys Arg Gln Leu Leu Ala Glu Arg Gln Lys Arg Ile Glu
            385             390             395             400
            Gln Gln Lys Glu Gln Arg Arg Leu Glu Glu Gln Arg Arg Glu
                        405             410             415
            Arg Glu Ala Arg Arg Gln Gln Glu Arg Glu Gln Arg Arg Glu Gln
                        420             425             430
```

```
Glu Glu Lys Arg Arg Leu Glu Glu Leu Glu Arg Arg Lys Glu Glu
            435                 440                 445

Glu Glu Arg Arg Arg Ala Glu Glu Lys Arg Arg Val Glu Arg Glu
        450                 455                 460

Gln Glu Tyr Ile Arg Arg Gln Leu Glu Glu Gln Arg His Leu Glu
465                 470                 475                 480

Val Leu Gln Gln Gln Leu Leu Gln Glu Gln Ala Met Leu Leu His Asp
                    485                 490                 495

His Arg Arg Pro His Pro Gln His Ser Gln Gln Pro Pro Pro Gln
            500                 505                 510

Gln Glu Arg Ser Lys Pro Ser Phe His Ala Pro Glu Pro Lys Ala His
            515                 520                 525

Tyr Glu Pro Ala Asp Arg Ala Arg Glu Val Pro Val Arg Thr Thr Ser
    530                 535                 540

Arg Ser Pro Val Leu Ser Arg Arg Asp Ser Pro Leu Gln Gly Ser Gly
545                 550                 555                 560

Gln Gln Asn Ser Gln Ala Gly Gln Arg Asn Ser Thr Ser Ile Glu Pro
                565                 570                 575

Arg Leu Leu Trp Glu Arg Val Glu Lys Leu Val Pro Arg Pro Gly Ser
            580                 585                 590

Gly Ser Ser Ser Gly Ser Ser Asn Ser Gly Ser Gln Pro Gly Ser His
        595                 600                 605

Pro Gly Ser Gln Ser Gly Ser Gly Glu Arg Phe Arg Val Arg Ser Ser
        610                 615                 620

Ser Lys Ser Glu Gly Ser Pro Ser Gln Arg Leu Glu Asn Ala Val Lys
625                 630                 635                 640

Lys Pro Glu Asp Lys Lys Glu Val Phe Arg Pro Leu Lys Pro Ala Gly
                645                 650                 655

Glu Val Asp Leu Thr Ala Leu Ala Lys Glu Leu Arg Ala Val Glu Asp
            660                 665                 670

Val Arg Pro Pro His Lys Val Thr Asp Tyr Ser Ser Ser Ser Glu Glu
        675                 680                 685

Ser Gly Thr Thr Asp Glu Glu Asp Asp Val Glu Gln Glu Gly Ala
        690                 695                 700

Asp Glu Ser Thr Ser Gly Pro Glu Asp Thr Arg Ala Ala Ser Ser Leu
705                 710                 715                 720

Asn Leu Ser Asn Gly Glu Thr Glu Ser Val Lys Thr Met Ile Val His
                725                 730                 735

Asp Asp Val Glu Ser Glu Pro Ala Met Thr Pro Ser Lys Glu Gly Thr
            740                 745                 750

Leu Ile Val Arg Gln Thr Gln Ser Ala Ser Ser Thr Leu Gln Lys His
        755                 760                 765

Lys Ser Ser Ser Ser Phe Thr Pro Phe Ile Asp Pro Arg Leu Leu Gln
    770                 775                 780

Ile Ser Pro Ser Ser Gly Thr Thr Val Thr Ser Val Val Gly Phe Ser
785                 790                 795                 800

Cys Asp Gly Met Arg Pro Glu Ala Ile Arg Gln Asp Pro Thr Arg Lys
                805                 810                 815

Gly Ser Val Val Asn Val Asn Pro Thr Asn Thr Arg Pro Gln Ser Asp
            820                 825                 830

Thr Pro Glu Ile Arg Lys Tyr Lys Lys Arg Phe Asn Ser Glu Ile Leu
        835                 840                 845
```

Cys Ala Ala Leu Trp Gly Val Asn Leu Leu Val Gly Thr Glu Ser Gly
850                 855                 860

Leu Met Leu Leu Asp Arg Ser Gly Gln Gly Lys Val Tyr Pro Leu Ile
865                 870                 875                 880

Asn Arg Arg Arg Phe Gln Gln Met Asp Val Leu Glu Gly Leu Asn Val
            885                 890                 895

Leu Val Thr Ile Ser Gly Lys Lys Asp Lys Leu Arg Val Tyr Tyr Leu
            900                 905                 910

Ser Trp Leu Arg Asn Lys Ile Leu His Asn Asp Pro Glu Val Glu Lys
            915                 920                 925

Lys Gln Gly Trp Thr Thr Val Gly Asp Leu Glu Gly Cys Val His Tyr
930                 935                 940

Lys Val Val Lys Tyr Glu Arg Ile Lys Phe Leu Val Ile Ala Leu Lys
945                 950                 955                 960

Ser Ser Val Glu Val Tyr Ala Trp Ala Pro Lys Pro Tyr His Lys Phe
            965                 970                 975

Met Ala Phe Lys Ser Phe Gly Glu Leu Val His Lys Pro Leu Leu Val
            980                 985                 990

Asp Leu Thr Val Glu Glu Gly Gln Arg Leu Lys Val Ile Tyr Gly Ser
            995                 1000                1005

Cys Ala Gly Phe His Ala Val Asp Val Asp Ser Gly Ser Val Tyr Asp
    1010                1015                1020

Ile Tyr Leu Pro Thr His Val Arg Lys Asn Pro His Ser Met Ile Gln
1025                1030                1035                1040

Cys Ser Ile Lys Pro His Ala Ile Ile Ile Leu Pro Asn Thr Asp Gly
            1045                1050                1055

Met Glu Leu Leu Val Cys Tyr Glu Asp Glu Gly Val Tyr Val Asn Thr
            1060                1065                1070

Tyr Gly Arg Ile Thr Lys Asp Val Val Leu Gln Trp Gly Glu Met Pro
            1075                1080                1085

Thr Ser Val Ala Tyr Ile Arg Ser Asn Gln Thr Met Gly Trp Gly Glu
            1090                1095                1100

Lys Ala Ile Glu Ile Arg Ser Val Glu Thr Gly His Leu Asp Gly Val
1105                1110                1115                1120

Phe Met His Lys Arg Ala Gln Arg Leu Lys Phe Leu Cys Glu Arg Asn
            1125                1130                1135

Asp Lys Val Phe Phe Ala Ser Val Arg Ser Gly Gly Ser Ser Gln Val
            1140                1145                1150

Tyr Phe Met Thr Leu Gly Arg Thr Ser Leu Leu Ser Trp
            1155                1160                1165

<210> SEQ ID NO 2
<211> LENGTH: 7334
<212> TYPE: DNA
<213> ORGANISM: Homo sapiens

<400> SEQUENCE: 2
gctcactcgc tcaactcggc gccgccgcgg ccccacgctc cgggcccgtc ctcgaggcgc      60
gcggcgcggg gcgcgggcgc cggggcctga ggcggcgggc gacgcccggg ggcctgacgg     120
ccggccccgc gccatggtgt gagcgccgcc gcccgtgcac gctccgtccg ccctccgcgc     180
ggcccggccg cagagagcc cgagcggcc cgagagcgca gccgagcccg ccgccgccgc       240
ccgcggcccc gcgaggagag taccgggccg gctcggctgc cgcgcgagga gcgcggtcgg     300
cggcctggtc tgcggctgag atacacagag cgacagagac atttattgtt atttgttttt    360

```
tggtggcaaa aagggaaaat ggcgaacgac tccccctgcaa aaagtctggt ggacatcgac      420
ctctcctccc tgcgggatcc tgctgggatt tttgagctgg tggaagtggt tggaaatggc      480
acctatggac aagtctataa gggtcgacat gttaaaacgg gtcagttggc agccatcaaa      540
gttatggatg tcactgagga tgaagaggaa gaaatcaaac tggagataaa tatgctaaag      600
aaatactctc atcacagaaa cattgcaaca tattatggtg ctttcatcaa aaagagccct      660
ccaggacatg atgaccaact ctggcttgtt atggagttct gtggggctgg gtccattaca      720
gaccttgtga agaacaccaa agggaacaca ctcaagaaag actggatcgc ttacatctcc      780
agagaaatcc tgaggggact ggcacatctt cacattcatc atgtgattca ccgggatatc      840
aagggccaga atgtgttgct gactgagaat gcagaggtga aacttgttga ctttggtgtg      900
agtgctcagc tggacaggac tgtggggcgg agaaatacgt tcataggcac tccctactgg      960
atggctcctg aggtcatcgc ctgtgatgag aacccagatg ccacctatga ttacagaagt     1020
gatctttggt cttgtggcat tacagccatt gagatggcag aagtgctccc cctctctgt      1080 gacatgcatc aatgagagc actgtttctc attcccagaa accctcctcc ccggctgaag     1140
tcaaaaaaat ggtcgaagaa gtttttttagt tttatagaag ggtgcctggt gaagaattac     1200
atgcagcggc cctctacaga gcagcttttg aaacatcctt ttataaggga tcagccaaat     1260
gaaaggcaag ttagaatcca gcttaaggat catatagatc gtaccaggaa gaagagaggc     1320
gagaaagatg aaactgagta tgagtacagt ggggagtgagg aagaagagga ggaagtgcct     1380
gaacaggaag gagagccaag ttccattgtg aacgtgcctg gtgagtctac tcttcgccga     1440
gatttcctga gactgcagca ggagaacaag gaacgttccg aggctcttcg gagacaacag     1500
ttactacagg agcaacagct ccgggagcag gaagaatata aaaggcaact gctggcagag     1560
agacagaagc ggattgagca gcagaaagaa cagaggcgac ggctagaaga gcaacaaagg     1620
agagagcggg aagctagaag gcagcaggaa cgtgaacagc gaaggagaga acaagaagaa     1680
aagaggcgtc tagaggagtt ggagagaagg cgcaaagaag aagaggagag gagacgggca     1740
gaagaagaaa agaggagagt tgaaagagaa caggagtata tcaggcgaca gctagaagag     1800
gagcagcggc acttggaagt ccttcagcag cagctgctcc aggagcaggc catgttactg     1860
catgaccata ggaggccgca cccgcagcac tcgcagcagc cgccaccacc gcagcaggaa     1920
aggagcaagc caagcttcca tgctcccgag cccaaagccc actacgagcc tgctgaccga     1980
gcgcgagagg ttcctgtgag aacaacatct cgctcccctg ttctgtcccg tcgagattcc     2040
ccactgcagg gcagtgggca gcagaatagc caggcaggac agagaaactc caccagtatt     2100
gagcccaggc ttctgtggga gagagtggag aagctggtgc ccagacctgg cagtggcagc     2160
tcctcagggt ccagcaactc aggatcccag cccgggtctc accctgggtc tcagagtggc     2220
tccggggaac gcttcagagt gagatcatca tccaagtctg aaggctctcc atctcagcgc     2280
ctggaaaatg cagtgaaaaa acctgaagat aaaaaggaag ttttcagacc cctcaagcct     2340
gctggcgaag tggatctgac cgcactggcc aaagagcttc gagcagtgga agatgtacgg     2400
ccacctcaca aagtaacgga ctactcctca tccagtgagg agtcggggac gacggatgag     2460
gaggacgacg atgtggagca ggaagggcgct gacgagtcca cctcaggacc agaggacacc     2520
agagcagcgt catctctgaa tttgagcaat ggtgaaacgg aatctgtgaa accatgatt     2580 gtccatgatg atgtagaaag tgagccggcc atgaccccat ccaaggaggg cactctaatc     2640
gtccgccaga ctcagtccgc tagtagcaca ctccagaaac acaaatcttc ctcctccttt     2700
```

```
acaccttttta tagacccccag attactacag atttctccat ctagcggaac aacagtgaca    2760
tctgtggtgg gattttcctg tgatgggatg agaccagaag ccataaggca agatcctacc    2820
cggaaaggct cagtggtcaa tgtgaatcct accaacacta ggccacagag tgacaccccg    2880
gagattcgta atacaagaa gaggtttaac tctgagattc tgtgtgctgc cttatgggga    2940
gtgaatttgc tagtgggtac agagagtggc ctgatgctgc tggacagaag tggccaaggg    3000
aaggtctatc ctcttatcaa ccgaagacga tttcaacaaa tggacgtact tgagggcttg    3060
aatgtcttgg tgacaatatc tggcaaaaag gataagttac gtgtctacta tttgtcctgg    3120
ttaagaaata aaatacttca caatgatcca gaagttgaga agaagcaggg atggacaacc    3180
gtaggggatt tggaaggatg tgtacattat aaagttgtaa aatatgaaag aatcaaattt    3240
ctggtgattg ctttgaagag ttctgtggaa gtctatgcgt gggcaccaaa gccatatcac    3300
aaatttatgg cctttaagtc atttggagaa ttggtacata agccattact ggtggatctc    3360
actgttgagg aaggccagag gttgaaagtg atctatggat cctgtgctgg attccatgct    3420
gttgatgtgg attcaggatc agtctatgac atttatctac caacacatgt aagaaagaac    3480
ccacactcta tgatccagtg tagcatcaaa ccccatgcaa tcatcatcct ccccaataca    3540 gatgaatgg agcttctggt gtgctatgaa gatgaggggg tttatgtaaa cacatatgga    3600
aggatcacca aggatgtagt tctacagtgg ggagagatgc ctacatcagt agcatatatt    3660
cgatccaatc agacaatggg ctggggagag aaggcccatag agatccgatc tgtggaaact    3720
ggtcacttgg atggtgtgtt catgcacaaa agggctcaaa gactaaaatt cttgtgtgaa    3780
cgcaatgaca aggtgttctt tgcctctgtt cggtctggtg gcagcagtca ggtttatttc    3840
atgaccttag gcaggacttc tcttctgagc tggtagaagc agtgtgatcc agggattact    3900
ggcctccaga gtcttcaaga tcctgagaac ttggaattcc ttgtaactgg agctcggagc    3960
tgcaccgagg gcaaccagga cagctgtgtg tgcagacctc atgtgttggg ttctctcccc    4020
tccttcctgt tcctcttata taccagttta tccccattct ttttttttt cttactccaa    4080 aataaatcaa ggctgcaatg cagctggtgc tgttcagatt ctaccatcag gtgctataag    4140
tgtttgggat tgagcatcat actggaaagc aaacacctttt cctccagctc cagaattcct    4200
tgtctctgaa tgactctgtc ttgtgggtgt ctgacagtgg cgacgatgaa catgccgttg    4260
gttttattgg cagtgggcac aaggaggtga gaagtggtgg taaaaggagc ggagtgctga    4320
agcagagagc agatttaata tagtaacatt aacagtgtat ttaattgaca tttcttttt    4380 gtaatgtgac gatatgtgga caaagaagaa gatgcaggtt taagaagtta atattataa    4440 aatgtgaaag acacagttac taggataact ttttttgtggg tggggcttgg gagatggggt    4500 ggggtggggtt aaggggtccc attttgtttc tttggatttg gggtggggt cctggccaag    4560 aactcagtca ttttctgtg taccaggttg cctaaatcat gtgcagatgg ttctaaaaaa    4620
aaaaaaaaaa aaaaaaaaaa aaggaaaaaa aaaagaaaaaa gaaaacgtg tgcattttgt    4680 ataatggcca gaactttgtc gtgtgacagt attagcactg cctcagttaa aggtttaatt    4740
tttgtttaaa cctagacgtg caacaaaagt tttaccacag tctgcacttg cagaagaaag    4800
aaaaaaattc aaaccacatg tttattttt ttttgcctac ctcattgttc ttaatgcatt    4860
gagaggtgat ttagttttata tgtttttgga agaaaccatt aatgtttaat ttaatcttaa    4920
taccaaaacg accagattga agtttgactt ttattgtcac aaatcagcag gcacaagaac    4980
tgtccatgaa gatgggaaat agccttaagg ctgatgcagt ttacttacaa gtttagaaac    5040
cagaatgctt tgttttttacc agattcacca ttagaggttg atggggcaac tgcagcccat    5100
```

```
gacacaagat ctcattgttc tcgatgtaga ggggttggta gcagacaggt ggttacatta      5160
gaatagtcac acaaactgtt cagtgttgca ggaacctttt cttggggtg ggggagtttc       5220 ccttttctaa aaatgcaatg cactaaaact attttaagaa tgtagttaat tctgcttatt      5280
cataaagtgg gcatcttctg tgttttaggt gtaatatcga agtcctggct tttctcgttt      5340
tctcacttgc tctcttgttc tctgtttttt taaaccaatt ttactttatg aatatattca      5400
tgacatttgt aataaatgtc ttgagaaaga atttgtttca tggcttcatg gtcatcactc      5460
aagctcccgt aaggatatta ccgtctcagg aaaggatcag gactccatgt cacagtcctg      5520
ccatcttact ttcctcttgt cgagttctga gtggaaataa ctgcattatg ctgctttaa       5580 cctcagtcat caaagaaac ttgctgtttt ttaggcttga tcttttcct ttgtggttaa        5640 ttttcctgta tattgtgaaa atgggggatt ttccctctgc tcccacccac ctaaacacag      5700
cagccatttg tacctgtttg cttcccatcc cacttggcac ccactctgac ctcttgtcag      5760
tttcctgttc ctggttccat cttttgaaa aaggccctcc tttgagctac aaacatctgg       5820
taagacaagt acatccactc atgaatgcag acacagcagc tggtggtttt gtgtatacct      5880
gtaaagacaa gctgagaagc ttacttttg gggaagtaaa agaagatgga aatggatgtt       5940
tcatttgtat gagtttggag cagtgctgaa ggccaaagcc gcctactggt ttgtagttaa      6000
cctagagaag gttgaaaaat taatcctacc tttaaggga tttgaggtag gctggattcc       6060
atcgccacag gactttagtt agaattaaat tcctgcttgt aatttatatc catgtttagg      6120
cttttcataa gatgaaacat gccacagtga acacactcgt gtacatatca agagaagaag     6180
gaaaggcaca ggtggagaac agtaaaaggt gggcagatgt ctttgaagaa atgctcaatg     6240
tctgatgcta gtgggagaa ggcagagaac aaaggatgtg gcataatggt cttaacatta      6300
tccaaagact tgaagctcca tgtctgtaag tcaaatgtta cacaaaaaaa aatgcaaatg     6360
gtgtttcatt ggaattacca agtgcttaga acttgctggc tttcccatag gtggtaaagg     6420
ggtctgagct cacaccgagt tgtgcttggc ttgcttgtgc agctccaggc acccggtggg     6480
cactctggtg gtgtttgtgg tgaactgaat tgaatccatt gttgggctta agttactgaa     6540
attggaacac cctttgtcct tctcggcggg ggcttcctgg tctgtgcttt acttggcttt     6600
tttccttccc gtcttagcct cacccccttg tcaaccagat tgagttgcta tagcttgatg     6660
cagggaccca gtgaagtttc tccgttaaag attgggagtc gtcgaaatgt ttagattctt     6720
ttaggaaagg aattattttc cccccttta cagggtagta acttctccac agaagtgcca     6780
atatggcaaa attacacaag aaaacagtat tgcaatgaca ccattacata aggaacattg     6840
aactgttaga ggagtgctct tccaaacaaa acaaaaatgt ctctaggttt agtcagagct     6900
ttcacaagta ataacctttc tgtattaaaa tcagagtaac cctttctgta ttgagtgcag     6960
tgttttttac tcttttctca tgcacatgtt acgttggaga aaatgtttac aaaaatggtt     7020
ttgttacact aatgcgcacc acatatttat ggtttatttt aagtgacttt ttatgggtta     7080
tttaggtttt cgtcttagtt gtagcacact taccctaatt ttgccaatta ttaatttgct     7140
aaatagtaat acaaatgaca aactgcatta aatttactaa ttataaaagc tgcaaagcag     7200
actggtggca agtacacagc ccttttttt gcagtgctaa cttgtctact gtgtattatg     7260
aaaattactg ttgtcccccc cccttttttt ccttaaataa agtaaaaatg acacctaaaa     7320
aaaaaaaaaa aaaa                                                        7334

<210> SEQ ID NO 3
```

<211> LENGTH: 1273
<212> TYPE: PRT
<213> ORGANISM: Homo sapiens

<400> SEQUENCE: 3

```
Met Ala Asn Asp Ser Pro Ala Lys Ser Leu Val Asp Ile Asp Leu Ser
 1               5                   10                  15

Ser Leu Arg Asp Pro Ala Gly Ile Phe Glu Leu Val Glu Val Val Gly
            20                  25                  30

Asn Gly Thr Tyr Gly Gln Val Tyr Lys Gly Arg His Val Lys Thr Gly
        35                  40                  45

Gln Leu Ala Ala Ile Lys Val Met Asp Val Thr Glu Asp Glu Glu Glu
    50                  55                  60

Glu Ile Lys Leu Glu Ile Asn Met Leu Lys Lys Tyr Ser His His Arg
65                  70                  75                  80

Asn Ile Ala Thr Tyr Tyr Gly Ala Phe Ile Lys Lys Ser Pro Pro Gly
                85                  90                  95

His Asp Asp Gln Leu Trp Leu Val Met Glu Phe Cys Gly Ala Gly Ser
            100                 105                 110

Ile Thr Asp Leu Val Lys Asn Thr Lys Gly Asn Thr Leu Lys Glu Asp
        115                 120                 125

Trp Ile Ala Tyr Ile Ser Arg Glu Ile Leu Arg Gly Leu Ala His Leu
    130                 135                 140

His Ile His His Val Ile His Arg Asp Ile Lys Gly Gln Asn Val Leu
145                 150                 155                 160

Leu Thr Glu Asn Ala Glu Val Lys Leu Val Asp Phe Gly Val Ser Ala
                165                 170                 175

Gln Leu Asp Arg Thr Val Gly Arg Arg Asn Thr Phe Ile Gly Thr Pro
            180                 185                 190

Tyr Trp Met Ala Pro Glu Val Ile Ala Cys Asp Glu Asn Pro Asp Ala
        195                 200                 205

Thr Tyr Asp Tyr Arg Ser Asp Leu Trp Ser Cys Gly Ile Thr Ala Ile
    210                 215                 220

Glu Met Ala Glu Gly Ala Pro Pro Leu Cys Asp Met His Pro Met Arg
225                 230                 235                 240

Ala Leu Phe Leu Ile Pro Arg Asn Pro Pro Arg Leu Lys Ser Lys
                245                 250                 255

Lys Trp Ser Lys Lys Phe Phe Ser Phe Ile Glu Gly Cys Leu Val Lys
            260                 265                 270

Asn Tyr Met Gln Arg Pro Ser Thr Glu Gln Leu Leu Lys His Pro Phe
        275                 280                 285

Ile Arg Asp Gln Pro Asn Glu Arg Gln Val Arg Ile Gln Leu Lys Asp
    290                 295                 300

His Ile Asp Arg Thr Arg Lys Lys Arg Gly Glu Lys Asp Glu Thr Glu
305                 310                 315                 320

Tyr Glu Tyr Ser Gly Ser Glu Glu Glu Glu Glu Val Pro Glu Gln
                325                 330                 335

Glu Gly Glu Pro Ser Ser Ile Val Asn Val Pro Gly Glu Ser Thr Leu
            340                 345                 350

Arg Arg Asp Phe Leu Arg Leu Gln Gln Glu Asn Lys Glu Arg Ser Glu
        355                 360                 365

Ala Leu Arg Arg Gln Gln Leu Leu Gln Glu Gln Gln Leu Arg Glu Gln
    370                 375                 380

Glu Glu Tyr Lys Arg Gln Leu Leu Ala Glu Arg Gln Lys Arg Ile Glu
```

```
                385                 390                 395                 400
Gln Gln Lys Glu Gln Arg Arg Leu Glu Glu Gln Arg Arg Glu
                    405                 410                 415
Arg Glu Ala Arg Arg Gln Glu Arg Glu Gln Arg Arg Glu Gln
                    420                 425                 430
Glu Glu Lys Arg Arg Leu Glu Leu Glu Arg Arg Lys Glu Glu
                    435                 440                 445
Glu Glu Arg Arg Arg Ala Glu Glu Lys Arg Arg Val Glu Arg Glu
                    450                 455                 460
Gln Glu Tyr Ile Arg Arg Gln Leu Glu Glu Gln Arg His Leu Glu
465                 470                 475                 480
Val Leu Gln Gln Gln Leu Leu Gln Glu Gln Ala Met Leu Leu His Asp
                    485                 490                 495
His Arg Arg Pro His Pro Gln His Ser Gln Gln Pro Pro Pro Gln
                    500                 505                 510
Gln Glu Arg Ser Lys Pro Ser Phe His Ala Pro Glu Pro Lys Ala His
                    515                 520                 525
Tyr Glu Pro Ala Asp Arg Ala Arg Glu Val Glu Asp Arg Phe Arg Lys
                    530                 535                 540
Thr Asn His Ser Ser Pro Glu Ala Gln Ser Lys Gln Thr Gly Arg Val
545                 550                 555                 560
Leu Glu Pro Pro Val Pro Ser Arg Ser Glu Ser Phe Ser Asn Gly Asn
                    565                 570                 575
Ser Glu Ser Val His Pro Ala Leu Gln Arg Pro Ala Glu Pro Gln Val
                    580                 585                 590
Pro Val Arg Thr Thr Ser Arg Ser Pro Val Leu Ser Arg Arg Asp Ser
                    595                 600                 605
Pro Leu Gln Gly Ser Gly Gln Gln Asn Ser Gln Ala Gly Gln Arg Asn
                    610                 615                 620
Ser Thr Ser Ser Ile Glu Pro Arg Leu Leu Trp Glu Arg Val Glu Lys
625                 630                 635                 640
Leu Val Pro Arg Pro Gly Ser Gly Ser Ser Ser Gly Ser Ser Asn Ser
                    645                 650                 655
Gly Ser Gln Pro Gly Ser His Pro Gly Ser Gln Ser Gly Ser Gly Glu
                    660                 665                 670
Arg Phe Arg Val Arg Ser Ser Lys Ser Glu Gly Ser Pro Ser Gln
                    675                 680                 685
Arg Leu Glu Asn Ala Val Lys Lys Pro Glu Asp Lys Lys Glu Val Phe
                    690                 695                 700
Arg Pro Leu Lys Pro Ala Asp Leu Thr Ala Leu Ala Lys Glu Leu Arg
705                 710                 715                 720
Ala Val Glu Asp Val Arg Pro Pro His Lys Val Thr Asp Tyr Ser Ser
                    725                 730                 735
Ser Ser Glu Glu Ser Gly Thr Thr Asp Glu Glu Asp Asp Val Glu
                    740                 745                 750
Gln Glu Gly Ala Asp Glu Ser Thr Ser Gly Pro Glu Asp Thr Arg Ala
                    755                 760                 765
Ala Ser Ser Leu Asn Leu Ser Asn Gly Glu Thr Glu Ser Val Lys Thr
                    770                 775                 780
Met Ile Val His Asp Asp Val Glu Ser Glu Pro Ala Met Thr Pro Ser
785                 790                 795                 800
Lys Glu Gly Thr Leu Ile Val Arg Gln Ser Thr Val Asp Gln Lys Arg
                    805                 810                 815
```

-continued

```
Ala Ser His His Glu Ser Asn Gly Phe Ala Gly Arg Ile His Leu Leu
        820                 825                 830

Pro Asp Leu Leu Gln Gln Ser His Ser Ser Thr Ser Ser Thr Ser
        835                 840                 845

Ser Ser Pro Ser Ser Ser Gln Pro Thr Pro Thr Met Ser Pro Gln Thr
850                 855                 860

Pro Gln Asp Lys Leu Thr Ala Asn Glu Thr Gln Ser Ala Ser Ser Thr
865                 870                 875                 880

Leu Gln Lys His Lys Ser Ser Ser Phe Thr Pro Phe Ile Asp Pro
                885                 890                 895

Arg Leu Leu Gln Ile Ser Pro Ser Ser Gly Thr Thr Val Thr Ser Val
                900                 905                 910

Val Gly Phe Ser Cys Asp Gly Met Arg Pro Glu Ala Ile Arg Gln Asp
        915                 920                 925

Pro Thr Arg Lys Gly Ser Val Val Asn Val Asn Pro Thr Asn Thr Arg
930                 935                 940

Pro Gln Ser Asp Thr Pro Glu Ile Arg Lys Tyr Lys Lys Arg Phe Asn
945                 950                 955                 960

Ser Glu Ile Leu Cys Ala Ala Leu Trp Gly Val Asn Leu Leu Val Gly
                965                 970                 975

Thr Glu Ser Gly Leu Met Leu Leu Asp Arg Ser Gly Gln Gly Lys Val
                980                 985                 990

Tyr Pro Leu Ile Asn Arg Arg Arg Phe Gln Gln Met Asp Val Leu Glu
                995                 1000                1005

Gly Leu Asn Val Leu Val Thr Ile Ser Gly Lys Lys Asp Lys Leu Arg
        1010                1015                1020

Val Tyr Tyr Leu Ser Trp Leu Arg Asn Lys Ile Leu His Asn Asp Pro
1025                1030                1035                1040

Glu Val Glu Lys Lys Gln Gly Trp Thr Thr Val Gly Asp Leu Glu Gly
                1045                1050                1055

Cys Val His Tyr Lys Val Val Lys Tyr Glu Arg Ile Lys Phe Leu Val
                1060                1065                1070

Ile Ala Leu Lys Ser Ser Val Glu Val Tyr Ala Trp Ala Pro Lys Pro
        1075                1080                1085

Tyr His Lys Phe Met Ala Phe Lys Ser Phe Gly Glu Leu Val His Lys
        1090                1095                1100

Pro Leu Leu Val Asp Leu Thr Val Glu Glu Gly Gln Arg Leu Lys Val
1105                1110                1115                1120

Ile Tyr Gly Ser Cys Ala Gly Phe His Ala Val Asp Val Asp Ser Gly
                1125                1130                1135

Ser Val Tyr Asp Ile Tyr Leu Pro Thr His Ile Gln Cys Ser Ile Lys
                1140                1145                1150

Pro His Ala Ile Ile Ile Leu Pro Asn Thr Asp Gly Met Glu Leu Leu
        1155                1160                1165

Val Cys Tyr Glu Asp Glu Gly Val Tyr Val Asn Thr Tyr Gly Arg Ile
        1170                1175                1180

Thr Lys Asp Val Val Leu Gln Trp Gly Glu Met Pro Thr Ser Val Ala
1185                1190                1195                1200

Tyr Ile Arg Ser Asn Gln Thr Met Gly Trp Gly Glu Lys Ala Ile Glu
                1205                1210                1215

Ile Arg Ser Val Glu Thr Gly His Leu Asp Gly Val Phe Met His Lys
        1220                1225                1230
```

Arg Ala Gln Arg Leu Lys Phe Leu Cys Glu Arg Asn Asp Lys Val Phe
        1235                1240                1245

Phe Ala Ser Val Arg Ser Gly Gly Ser Ser Gln Val Tyr Phe Met Thr
    1250                1255                1260

Leu Gly Arg Thr Ser Leu Leu Ser Trp
1265                1270

<210> SEQ ID NO 4
<211> LENGTH: 7658
<212> TYPE: DNA
<213> ORGANISM: Homo sapiens

<400> SEQUENCE: 4

| | | |
|---|---|---|
| gctcactcgc tcaactcggc gccgccgcgg ccccacgctc cgggcccgtc ctcgaggcgc | 60 |
| gcggcgcggg gcgcgggcgc cggggcctga ggcggcgggc gacgcccggg ggcctgacgg | 120 |
| ccggccccgc gccatggtgt gagcgccgcc gcccgtgcac gctccgtccg ccctccgcgc | 180 |
| ggcccggccg gcagagagcc ccgagcgccc cgagagcgca gccgagcccg ccgccgccgc | 240 |
| ccgcggcccc gcgaggagag taccgggccg gctcggctgc cgcgcgagga gcgcggtcgg | 300 |
| cggcctggtc tgcggctgag atacacagag cgacagagac atttattgtt atttgttttt | 360 |
| tggtggcaaa aagggaaaat ggcgaacgac tcccctgcaa aaagtctggt ggacatcgac | 420 |
| ctctcctccc tgcgggatcc tgctgggatt tttgagctgg tggaagtggt tggaaatggc | 480 |
| acctatggac aagtctataa gggtcgacat gttaaaacgg gtcagttggc agccatcaaa | 540 |
| gttatggatg tcactgagga tgaagaggaa gaaatcaaac tggagataaa tatgctaaag | 600 |
| aaatactctc atcacagaaa cattgcaaca tattatggtg ctttcatcaa aaagagccct | 660 |
| ccaggacatg atgaccaact ctggcttgtt atggagttct gtggggctgg gtccattaca | 720 |
| gaccttgtga agaacaccaa agggaacaca ctcaaagaag actggatcgc ttacatctcc | 780 |
| agagaaatcc tgaggggact ggcacatctt cacattcatc atgtgattca ccgggatatc | 840 |
| aagggccaga atgtgttgct gactgagaat gcagaggtga acttgttga ctttggtgtg | 900 |
| agtgctcagc tggacaggac tgtggggcgg agaaatacgt tcataggcac tccctactgg | 960 |
| atggctcctg aggtcatcgc ctgtgatgag aacccagatg ccacctatga ttacagaagt | 1020 |
| gatctttggt cttgtggcat tacagccatt gagatggcag aaggtgctcc ccctctctgt | 1080 |
| gacatgcatc caatgagagc actgtttctc attcccagaa accctcctcc ccggctgaag | 1140 |
| tcaaaaaaat ggtcgaagaa gttttttagt tttatagaag ggtgcctggt gaagaattac | 1200 |
| atgcagcggc cctctacaga gcagcttttg aaacatcctt ttataaggga tcagccaaat | 1260 |
| gaaaggcaag ttagaatcca gcttaaggat catatagatc gtaccaggaa gagagaggc | 1320 |
| gagaaagatg aaactgagta tgagtacagt gggagtgagg aagaagagga ggaagtgcct | 1380 |
| gaacaggaag gagagccaag ttccattgtg aacgtgcctg gtgagtctac tcttcgccga | 1440 |
| gatttcctga gactgcagca ggagaacaag gaacgttccg aggctcttcg gagacaacag | 1500 |
| ttactacagg agcaacagct ccgggagcag gaagaatata aaaggcaact gctggcagag | 1560 |
| agacagaagc ggattgagca gcagaaagaa cagaggcgac ggctagaaga gcaacaaagg | 1620 |
| agagagcggg aagctagaag gcagcaggaa cgtgaacagc gaaggagaga acaagaagaa | 1680 |
| aagaggcgtc tagaggagtt ggagagaagg cgcaaagaag aagaggagag gagacgggca | 1740 |
| gaagaagaaa agaggagagt tgaaagagaa caggagtata tcaggcgaca gctagaagag | 1800 |
| gagcagcggc acttggaagt ccttcagcag cagctgctcc aggagcaggc catgttactg | 1860 |

```
catgaccata ggaggccgca cccgcagcac tcgcagcagc cgccaccacc gcagcaggaa    1920
aggagcaagc caagcttcca tgctcccgag cccaaagccc actacgagcc tgctgaccga    1980
gcgcgagagg tggaagatag atttaggaaa actaaccaca gctcccctga agcccagtct    2040
aagcagacag gcagagtatt ggagccacca gtgccttccc gatcagagtc ttttccaat     2100 ggcaactccg agtctgtgca tcccgccctg cagagaccag cggagccaca ggttcctgtg    2160
agaacaacat ctcgctcccc tgttctgtcc cgtcgagatt ccccactgca gggcagtggg    2220
cagcagaata gccaggcagg acagagaaac tccaccagca gtattgagcc caggcttctg    2280
tgggagagag tggagaagct ggtgcccaga cctggcagtg gcagctcctc agggtccagc    2340
aactcaggat cccagcccgg gtctcaccct gggtctcaga gtggctccgg ggaacgcttc    2400
agagtgagat catcatccaa gtctgaaggc tctccatctc agcgcctgga aaatgcagtg    2460
aaaaaacctg aagataaaaa ggaagttttc agacccctca agcctgctga tctgaccgca    2520
ctggccaaag agcttcgagc agtggaagat gtacggccac ctcacaaagt aacggactac    2580
tcctcatcca gtgaggagtc ggggacgacg gatgaggagg acgacgatgt ggagcaggaa    2640
ggggctgacg agtccacctc aggaccagag gacaccagag cagcgtcatc tctgaatttg    2700
agcaatggtg aaacggaatc tgtgaaaacc atgattgtcc atgatgatgt agaaagtgag    2760
ccggccatga ccccatccaa ggagggcact ctaatcgtcc gccagagtac agttgaccaa    2820
aagcgtgcca gccatcatga gagcaatggc tttgccggtc gcattcacct cttgccagat    2880
ctcttacagc aaagccattc ctcctccact tcctccacct cctcctcccc atcctccagc    2940
cagccgacac ccaccatgtc cccacagaca ccccaggaca agctcactgc taatgagact    3000
cagtccgcta gtagcacact ccagaaacac aaatcttcct cctcctttac accttttata    3060
gaccccagat tactacagat ttctccatct agcggaacaa cagtgacatc tgtggtggga    3120
ttttcctgtg atgggatgag accagaagcc ataaggcaag atcctacccg gaaaggctca    3180
gtggtcaatg tgaatcctac caacactagg ccacagagtg acaccccgga gattcgtaaa    3240
tacaagaaga ggtttaactc tgagattctg tgtgctgcct tatggggagt gaatttgcta    3300
gtgggtacag agagtggcct gatgctgctg acagaagtg gccaagggaa ggtctatcct    3360
cttatcaacc gaagacgatt tcaacaaatg gacgtacttg agggcttgaa tgtcttggtg    3420
acaatatctg gcaaaaagga taagttacgt gtctactatt tgtcctggtt aagaaataaa    3480
atacttcaca atgatccaga agttgagaag aagcagggat ggacaaccgt agggatttg    3540 gaaggatgtg tacattataa agttgtaaaa tatgaaagaa tcaaatttct ggtgattgct    3600
ttgaagagtt ctgtggaagt ctatgcgtgg gcaccaaagc catatcacaa atttatggcc    3660
tttaagtcat ttgagaatt ggtacataag ccattactgg tggatctcac tgttgaggaa    3720
ggccagaggt tgaaagtgat ctatggatcc tgtgctggat ccatgctgt tgatgtggat    3780 tcaggatcag tctatgacat ttatctacca acacatatcc agtgtagcat caaaccccat    3840
gcaatcatca tcctccccaa tacagatgga atggagcttc tggtgtgcta tgaagatgag    3900
ggggtttatg taaacacata tggaaggatc accaaggatg tagttctaca gtggggagag    3960
atgcctacat cagtagcata tattcgatcc aatcagacaa tgggctgggg agagaaggcc    4020
atagagatcc gatctgtgga aactggtcac ttggatggtg tgttcatgca caaagggct    4080 caaagactaa aattcttgtg tgaacgcaat gacaaggtgt ctttgcctc tgttcggtct    4140 ggtggcagca gtcaggttta tttcatgacc ttaggcagga cttctcttct gagctggtag    4200
aagcagtgtg atccagggat tactggcctc cagagtcttc aagatcctga gaacttggaa    4260
```

```
ttccttgtaa ctggagctcg gagctgcacc gagggcaacc aggacagctg tgtgtgcaga    4320
cctcatgtgt tgggttctct cccctccttc ctgttcctct tatataccag tttatcccca    4380
ttcttttttt ttttcttact ccaaaataaa tcaaggctgc aatgcagctg gtgctgttca    4440
gattctacca tcaggtgcta taagtgtttg ggattgagca tcatactgga aagcaaacac    4500
ctttcctcca gctccagaat tccttgtctc tgaatgactc tgtcttgtgg gtgtctgaca    4560
gtggcgacga tgaacatgcc gttggtttta ttggcagtgg gcacaaggag gtgagaagtg    4620
gtggtaaaag gagcggagtg ctgaagcaga gagcagattt aatatagtaa cattaacagt    4680
gtatttaatt gacatttctt ttttgtaatg tgacgatatg tggacaaaga agaagatgca    4740
ggtttaagaa gttaatattt ataaaatgtg aaagacacag ttactaggat aactttttg     4800 tgggtggggc ttgggagatg gggtggggtg ggttaagggg tcccattttg tttctttgga    4860
tttggggtgg gggtcctggc caagaactca gtcattttc tgtgtaccag gttgcctaaa     4920
tcatgtgcag atggttctaa aaaaaaaaa aaaaaaaaa aaaaaaggaa aaaaaaaag       4980 aaaaagaaaa cgtgtgcatt tgtataatg gccagaactt tgtcgtgtga cagtattagc     5040
actgcctcag ttaaaggttt aatttttgtt taaacctaga cgtgcaacaa aagttttacc    5100
acagtctgca cttgcagaag aaagaaaaaa attcaaacca catgtttatt tttttttgc     5160 ctacctcatt gttcttaatg cattgagagg tgatttagtt tatatgtttt tggaagaaac    5220
cattaatgtt taatttaatc ttaataccaa aacgaccaga ttgaagtttg acttttattg    5280
tcacaaatca gcaggcacaa gaactgtcca tgaagatggg aaatagcctt aaggctgatg    5340
cagtttactt acaagtttag aaaccagaat gctttgtttt taccagattc accattagag    5400
gttgatgggg caactgcagc ccatgacaca agatctcatt gttctcgatg tagaggggtt    5460
ggtagcagac aggtggttac attagaatag tcacacaaac tgttcagtgt tgcaggaacc    5520
ttttcttggg ggtgggggag tttccctttt ctaaaaatgc aatgcactaa aactatttta    5580
agaatgtagt taattctgct tattcataaa gtgggcatct tctgtgtttt aggtgtaata    5640
tcgaagtcct ggcttttctc gttttctcac ttgctctctt gttctctgtt ttttaaacc    5700 aattttactt tatgaatata ttcatgacat ttgtaataaa tgtcttgaga aagaatttgt    5760
ttcatggctt catggtcatc actcaagctc ccgtaaggat attaccgtct caggaaagga    5820
tcaggactcc atgtcacagt cctgccatct tactttcctc ttgtcgagtt ctgagtggaa    5880
ataactgcat tatggctgct ttaacctcag tcatcaaaag aaacttgctg ttttttaggc    5940
ttgatctttt tcctttgtgg ttaattttcc tgtatattgt gaaatgggg gattttccct     6000 ctgctcccac ccacctaaac acagcagcca tttgtacctg tttgcttccc atcccacttg    6060
gcacccactc tgacctcttg tcagtttcct gttcctggtt ccatcttttt gaaaaaggcc    6120
ctcctttgag ctacaaacat ctggtaagac aagtacatcc actcatgaat gcagacacag    6180
cagctggtgg ttttgtgtat acctgtaaag acaagctgag aagcttactt tttggggaag    6240
taaaagaaga tggaaatgga tgtttcattt gtatgagttt ggagcagtgc tgaaggccaa    6300
agccgcctac tggtttgtag ttaacctaga gaaggttgaa aaattaatcc tacctttaaa    6360
gggatttgag gtaggctgga ttccatcgcc acaggacttg agttagaatt aaattcctgc    6420
ttgtaattta tatccatgtt taggcttttc ataagatgaa acatgccaca gtgaacacac    6480
tcgtgtacat atcaagagaa gaaggaaagg cacaggtgga gaacagtaaa aggtgggcag    6540
atgtctttga agaaatgctc aatgtctgat gctaagtggg agaaggcaga gaacaaagga    6600
```

-continued

```
tgtggcataa tggtcttaac attatccaaa gacttgaagc tccatgtctg taagtcaaat    6660
gttacacaaa aaaaaatgca aatggtgttt cattggaatt accaagtgct tagaacttgc    6720
tggctttccc ataggtggta aagggggtctg agctcacacc gagttgtgct tggcttgctt   6780
gtgcagctcc aggcacccgg tgggcactct ggtggtgttt gtggtgaact gaattgaatc    6840
cattgttggg cttaagttac tgaaattgga acacccttgg tccttctcgg cgggggcttc    6900
ctggtctgtg ctttacttgg ctttttttcct tcccgtctta gcctcacccc cttgtcaacc   6960
agattgagtt gctatagctt gatgcaggga cccagtgaag tttctccgtt aaagattggg    7020
agtcgtcgaa atgtttagat tcttttagga aaggaattat tttcccccct tttacagggt    7080
agtaacttct ccacagaagt gccaatatgg caaaattaca caagaaaaca gtattgcaat    7140
gacaccatta cataaggaac attgaactgt tagaggagtg ctcttccaaa caaaacaaaa    7200
atgtctctag gtttagtcag agctttcaca agtaataacc tttctgtatt aaaatcagag    7260 taacccttttc tgtattgagt gcagtgtttt ttactctttt ctcatgcaca tgttacgttg    7320
gagaaaatgt ttacaaaaat ggttttgtta cactaatgcg caccacatat ttatggttta    7380
ttttaagtga cttttatgg gttatttagg ttttcgtctt agttgtagca cacttacccct   7440 aattttgcca attattaatt tgctaaatag taatacaaat gacaaactgc attaaattta    7500
ctaattataa aagctgcaaa gcagactggt ggcaagtaca cagcccttttt ttttgcagtg    7560 ctaacttgtc tactgtgtat tatgaaaatt actgttgtcc ccccacccctt ttttccttaa    7620 ataaagtaaa aatgacacct aaaaaaaaaa aaaaaaaa                             7658
```

<210> SEQ ID NO 5
<211> LENGTH: 1212
<212> TYPE: PRT
<213> ORGANISM: Homo sapiens

<400> SEQUENCE: 5

```
Met Ala Asn Asp Ser Pro Ala Lys Ser Leu Val Asp Ile Asp Leu Ser
 1               5                  10                  15

Ser Leu Arg Asp Pro Ala Gly Ile Phe Glu Leu Val Glu Val Val Gly
            20                  25                  30

Asn Gly Thr Tyr Gly Gln Val Tyr Lys Gly Arg His Val Lys Thr Gly
        35                  40                  45

Gln Leu Ala Ala Ile Lys Val Met Asp Val Thr Glu Asp Glu Glu Glu
    50                  55                  60

Glu Ile Lys Leu Glu Ile Asn Met Leu Lys Lys Tyr Ser His His Arg
65                  70                  75                  80

Asn Ile Ala Thr Tyr Tyr Gly Ala Phe Ile Lys Lys Ser Pro Pro Gly
                85                  90                  95

His Asp Asp Gln Leu Trp Leu Val Met Glu Phe Cys Gly Ala Gly Ser
            100                 105                 110

Ile Thr Asp Leu Val Lys Asn Thr Lys Gly Asn Thr Leu Lys Glu Asp
        115                 120                 125

Trp Ile Ala Tyr Ile Ser Arg Glu Ile Leu Arg Gly Leu Ala His Leu
    130                 135                 140

His Ile His His Val Ile His Arg Asp Ile Lys Gly Gln Asn Val Leu
145                 150                 155                 160

Leu Thr Glu Asn Ala Glu Val Lys Leu Val Asp Phe Gly Val Ser Ala
                165                 170                 175

Gln Leu Asp Arg Thr Val Gly Arg Arg Asn Thr Phe Ile Gly Thr Pro
            180                 185                 190
```

```
Tyr Trp Met Ala Pro Glu Val Ile Ala Cys Asp Glu Asn Pro Asp Ala
            195                 200                 205
Thr Tyr Asp Tyr Arg Ser Asp Leu Trp Ser Cys Gly Ile Thr Ala Ile
    210                 215                 220
Glu Met Ala Glu Gly Ala Pro Pro Leu Cys Asp Met His Pro Met Arg
225                 230                 235                 240
Ala Leu Phe Leu Ile Pro Arg Asn Pro Pro Arg Leu Lys Ser Lys
                245                 250                 255
Lys Trp Ser Lys Lys Phe Phe Ser Phe Ile Glu Gly Cys Leu Val Lys
                260                 265                 270
Asn Tyr Met Gln Arg Pro Ser Thr Glu Gln Leu Leu Lys His Pro Phe
            275                 280                 285
Ile Arg Asp Gln Pro Asn Glu Arg Gln Val Arg Ile Gln Leu Lys Asp
        290                 295                 300
His Ile Asp Arg Thr Arg Lys Lys Arg Gly Glu Lys Asp Glu Thr Glu
305                 310                 315                 320
Tyr Glu Tyr Ser Gly Ser Glu Glu Glu Glu Glu Val Pro Glu Gln
                325                 330                 335
Glu Gly Glu Pro Ser Ser Ile Val Asn Val Pro Gly Glu Ser Thr Leu
            340                 345                 350
Arg Arg Asp Phe Leu Arg Leu Gln Gln Glu Asn Lys Glu Arg Ser Glu
                355                 360                 365
Ala Leu Arg Arg Gln Gln Leu Leu Gln Glu Gln Gln Leu Arg Glu Gln
            370                 375                 380
Glu Glu Tyr Lys Arg Gln Leu Leu Ala Glu Arg Gln Lys Arg Ile Glu
385                 390                 395                 400
Gln Gln Lys Glu Gln Arg Arg Arg Leu Glu Glu Gln Arg Arg Glu
                405                 410                 415
Arg Glu Ala Arg Arg Gln Gln Glu Arg Glu Gln Arg Arg Glu Gln
                420                 425                 430
Glu Glu Lys Arg Arg Leu Glu Glu Leu Glu Arg Arg Arg Lys Glu Glu
            435                 440                 445
Glu Glu Arg Arg Arg Ala Glu Glu Lys Arg Arg Val Glu Arg Glu
            450                 455                 460
Gln Glu Tyr Ile Arg Arg Gln Leu Glu Glu Glu Gln Arg His Leu Glu
465                 470                 475                 480
Val Leu Gln Gln Gln Leu Leu Gln Glu Gln Ala Met Leu Leu His Asp
                485                 490                 495
His Arg Arg Pro His Pro Gln His Ser Gln Gln Pro Pro Pro Pro Gln
                500                 505                 510
Gln Glu Arg Ser Lys Pro Ser Phe His Ala Pro Glu Pro Lys Ala His
            515                 520                 525
Tyr Glu Pro Ala Asp Arg Ala Arg Glu Val Glu Asp Arg Phe Arg Lys
530                 535                 540
Thr Asn His Ser Ser Pro Glu Ala Gln Ser Lys Gln Thr Gly Arg Val
545                 550                 555                 560
Leu Glu Pro Pro Val Pro Ser Arg Ser Glu Ser Phe Ser Asn Gly Asn
                565                 570                 575
Ser Glu Ser Val His Pro Ala Leu Gln Arg Pro Ala Glu Pro Gln Val
            580                 585                 590
Pro Val Arg Thr Thr Ser Arg Ser Pro Val Leu Ser Arg Arg Asp Ser
            595                 600                 605
```

-continued

```
Pro Leu Gln Gly Ser Gly Gln Gln Asn Ser Gln Ala Gly Gln Arg Asn
    610                 615                 620
Ser Thr Ser Ser Ile Glu Pro Arg Leu Leu Trp Glu Arg Val Glu Lys
625                 630                 635                 640
Leu Val Pro Arg Pro Gly Ser Gly Ser Ser Gly Ser Ser Asn Ser
            645                 650                 655
Gly Ser Gln Pro Gly Ser His Pro Gly Ser Gln Ser Gly Ser Gly Glu
                660                 665                 670
Arg Phe Arg Val Arg Ser Ser Lys Ser Glu Gly Ser Pro Ser Gln
                675                 680                 685
Arg Leu Glu Asn Ala Val Lys Lys Pro Glu Asp Lys Lys Glu Val Phe
    690                 695                 700
Arg Pro Leu Lys Pro Ala Gly Glu Val Asp Leu Thr Ala Leu Ala Lys
705                 710                 715                 720
Glu Leu Arg Ala Val Glu Asp Val Arg Pro Pro His Lys Val Thr Asp
                725                 730                 735
Tyr Ser Ser Ser Glu Ser Gly Thr Thr Asp Glu Glu Asp
                740                 745                 750
Asp Val Glu Gln Glu Gly Ala Asp Glu Ser Thr Ser Gly Pro Glu Asp
            755                 760                 765
Thr Arg Ala Ala Ser Ser Leu Asn Leu Ser Asn Gly Glu Thr Glu Ser
    770                 775                 780
Val Lys Thr Met Ile Val His Asp Asp Val Glu Ser Glu Pro Ala Met
785                 790                 795                 800
Thr Pro Ser Lys Glu Gly Thr Leu Ile Val Arg Gln Thr Gln Ser Ala
                805                 810                 815
Ser Ser Thr Leu Gln Lys His Lys Ser Ser Ser Phe Thr Pro Phe
    820                 825                 830
Ile Asp Pro Arg Leu Leu Gln Ile Ser Pro Ser Ser Gly Thr Thr Val
            835                 840                 845
Thr Ser Val Val Gly Phe Ser Cys Asp Gly Met Arg Pro Glu Ala Ile
    850                 855                 860
Arg Gln Asp Pro Thr Arg Lys Gly Ser Val Val Asn Val Asn Pro Thr
865                 870                 875                 880
Asn Thr Arg Pro Gln Ser Asp Thr Pro Glu Ile Arg Lys Tyr Lys Lys
                885                 890                 895
Arg Phe Asn Ser Glu Ile Leu Cys Ala Ala Leu Trp Gly Val Asn Leu
            900                 905                 910
Leu Val Gly Thr Glu Ser Gly Leu Met Leu Leu Asp Arg Ser Gly Gln
            915                 920                 925
Gly Lys Val Tyr Pro Leu Ile Asn Arg Arg Phe Gln Gln Met Asp
    930                 935                 940
Val Leu Glu Gly Leu Asn Val Leu Val Thr Ile Ser Gly Lys Lys Asp
945                 950                 955                 960
Lys Leu Arg Val Tyr Tyr Leu Ser Trp Leu Arg Asn Lys Ile Leu His
                965                 970                 975
Asn Asp Pro Glu Val Glu Lys Lys Gln Gly Trp Thr Thr Val Gly Asp
            980                 985                 990
Leu Glu Gly Cys Val His Tyr Lys Val Lys Tyr Glu Arg Ile Lys
        995                 1000                1005
Phe Leu Val Ile Ala Leu Lys Ser Ser Val Glu Val Tyr Ala Trp Ala
    1010                1015                1020
Pro Lys Pro Tyr His Lys Phe Met Ala Phe Lys Ser Phe Gly Glu Leu
```

Val His Lys Pro Leu Leu Val Asp Leu Thr Val Glu Glu Gly Gln Arg
1045                      1050                      1055

Leu Lys Val Ile Tyr Gly Ser Cys Ala Gly Phe His Ala Val Asp Val
             1060                      1065                      1070

Asp Ser Gly Ser Val Tyr Asp Ile Tyr Leu Pro Thr His Ile Gln Cys
        1075                      1080                      1085

Ser Ile Lys Pro His Ala Ile Ile Ile Leu Pro Asn Thr Asp Gly Met
    1090                      1095                      1100

Glu Leu Leu Val Cys Tyr Glu Asp Glu Gly Val Tyr Val Asn Thr Tyr
1105                      1110                      1115                      1120

Gly Arg Ile Thr Lys Asp Val Val Leu Gln Trp Gly Glu Met Pro Thr
             1125                      1130                      1135

Ser Val Ala Tyr Ile Arg Ser Asn Gln Thr Met Gly Trp Gly Glu Lys
        1140                      1145                      1150

Ala Ile Glu Ile Arg Ser Val Glu Thr Gly His Leu Asp Gly Val Phe
    1155                      1160                      1165

Met His Lys Arg Ala Gln Arg Leu Lys Phe Leu Cys Glu Arg Asn Asp
1170                      1175                      1180

Lys Val Phe Phe Ala Ser Val Arg Ser Gly Gly Ser Ser Gln Val Tyr
1185                      1190                      1195                      1200

Phe Met Thr Leu Gly Arg Thr Ser Leu Leu Ser Trp
             1205                      1210

<210> SEQ ID NO 6
<211> LENGTH: 7102
<212> TYPE: DNA
<213> ORGANISM: Homo sapiens

<400> SEQUENCE: 6

```
ggaaaatggc gaacgactcc cctgcaaaaa gtctggtgga catcgacctc tcctccctgc    60
gggatcctgc tgggattttt gagctggtgg aagtggttgg aaatggcacc tatggacaag   120
tctataaggg tcgacatgtt aaaacgggtc agttggcagc catcaaagtt atggatgtca   180
ctgaggatga agaggaagaa atcaaactgg agataaatat gctaaagaaa tactctcatc   240
acagaaacat tgcaacatat tatggtgctt tcatcaaaaa gagccctcca ggacatgatg   300
accaactctg gcttgttatg gagttctgtg ggctgggtc cattacagac ttgtgaaga    360 acaccaaagg gaacacactc aaagaagact ggatcgctta catctccaga gaaatcctga   420
ggggactggc acatcttcac attcatcatg tgattcaccg ggatatcaag gccagaatg    480 tgttgctgac tgagaatgca gaggtgaaac ttgttgactt tggtgtgagt gctcagctgg   540
acaggactgt ggggcggaga aatacgttca taggcactcc ctactggatg gctcctgagg   600
tcatcgcctg tgatgagaac ccagatgcca cctatgatta cagaagtgat ctttggtctt   660
gtggcattac agccattgag atggcagaag gtgctccccc tctctgtgac atgcatccaa   720
tgagagcact gtttctcatt cccagaaacc ctcctccccg gctgaagtca aaaaaatggt   780
cgaagaagtt ttttagtttt atagaagggt gcctggtgaa gaattacatg cagcggccct   840
ctacagagca gcttttgaaa catccttta agggatca gccaaatgaa aggcaagtta    900
gaatccagct taaggatcat atagatcgta ccaggaagaa gagaggcgag aaagatgaaa   960
ctgagtatga gtacagtggg agtgaggaag aagaggagga gtgcctgaa caggaaggag  1020 agccaagttc cattgtgaac gtgcctggtg agtctactct tcgccgagat ttcctgagac  1080
```

```
tgcagcagga gaacaaggaa cgttccgagg ctcttcggag acaacagtta ctacaggagc    1140
aacagctccg ggagcaggaa gaatataaaa ggcaactgct ggcagagaga cagaagcgga    1200
ttgagcagca gaaagaacag aggcgacggc tagaagagca acaaaggaga gagcgggaag    1260
ctagaaggca gcaggaacgt gaacagcgaa ggagagaaca agaagaaaag aggcgtctag    1320
aggagttgga gagaaggcgc aaagaagaag aggagaggag acgggcagaa gaagaaaaga    1380
ggagagttga aagagaacag gagtatatca ggcgacagct agaagaggag cagcggcact    1440
tggaagtcct tcagcagcag ctgctccagg agcaggccat gttactgcat gaccatagga    1500
ggccgcaccc gcagcactcg cagcagccgc caccaccgca gcaggaaagg agcaagccaa    1560
gcttccatgc tcccgagccc aaagcccact acgagcctgc tgaccgagcg cgagaggtgg    1620
aagatagatt taggaaaact aaccacagct cccctgaagc ccagtctaag cagacaggca    1680
gagtattgga gccaccagtg ccttcccgat cagagtcttt ttccaatggc aactccgagt    1740
ctgtgcatcc cgccctgcag agaccagcgg agccacaggt tcctgtgaga acaacatctc    1800
gctcccctgt tctgtcccgt cgagattccc cactgcaggg cagtgggcag cagaatagcc    1860
aggcaggaca gagaaactcc accagcagta ttgagcccag gcttctgtgg gagagagtgg    1920
agaagctggt gcccagacct ggcagtgca gctcctcagg gtccagcaac tcaggatccc    1980
agcccgggtc tcaccctggg tctcagagtg gctccgggga acgcttcaga gtgagatcat    2040
catccaagtc tgaaggctct ccatctcagc gcctggaaaa tgcagtgaaa aaacctgaag    2100
ataaaaagga agttttcaga ccccctcaagc ctgctggcga agtggatctg accgcactgg    2160
ccaaagagct tcgagcagtg gaagatgtac ggccacctca caaagtaacg gactactcct    2220
catccagtga ggagtcgggg acgacggatg aggaggacga cgatgtggag caggaagggg    2280
ctgacgagtc cacctcagga ccagaggaca ccagagcagc gtcatctctg aatttgagca    2340
atggtgaaac ggaatctgtg aaaaccatga ttgtccatga tgatgtagaa agtgagccgg    2400
ccatgacccc atccaaggag ggcactctaa tcgtccgcca gactcagtcc gctagtagca    2460
cactccagaa acacaaatct tcctcctcct ttacaccttt tatagacccc agattactac    2520
agatttctcc atctagcgga acaacagtga catctgtggt gggattttcc tgtgatggga    2580
tgagaccaga agccataagg caagatccta cccggaaagg ctcagtggtc aatgtgaatc    2640
ctaccaacac taggccacag agtgacaccc cggagattcg taaatacaag aagaggttta    2700
actctgagat tctgtgtgct gccttatggg gagtgaattt gctagtgggt acagagagtg    2760
gcctgatgct gctggacaga agtggccaag ggaaggtcta tcctcttatc aaccgaagac    2820
gatttcaaca aatggacgta cttgagggct tgaatgtctt ggtgacaata tctggcaaaa    2880
aggataagtt acgtgtctac tatttgtcct ggttaagaaa taaatactt cacaatgatc    2940 cagaagttga gaagaagcag ggatggacaa ccgtagggga tttggaagga tgtgtacatt    3000
ataaagttgt aaaatatgaa agaatcaaat ttctggtgat tgctttgaag agttctgtgg    3060
aagtctatgc gtgggcacca aagccatatc acaaatttat ggcctttaag tcatttggag    3120
aattggtaca taagccatta ctggtggatc tcactgttga ggaaggccag aggttgaaag    3180
tgatctatgg atcctgtgct ggattccatg ctgttgatgt ggattcagga tcagtctatg    3240
acatttatct accaacacat atccagtgta gcatcaaacc ccatgcaatc atcatcctcc    3300
ccaatacaga tggaatggag cttctggtgt gctatgaaga tgaggggtt tatgtaaaca    3360 catatggaag gatcaccaag gatgtagttc tacagtgggg agagatgcct acatcagtag    3420
catatattcg atccaatcag acaatgggct ggggagagaa ggccatagag atccgatctg    3480
```

```
tggaaactgg tcacttggat ggtgtgttca tgcacaaaag ggctcaaaga ctaaaattct    3540
tgtgtgaacg caatgacaag gtgttctttg cctctgttcg gtctggtggc agcagtcagg    3600
tttatttcat gaccttaggc aggacttctc ttctgagctg gtagaagcag tgtgatccag    3660
ggattactgg cctccagagt cttcaagatc ctgagaactt ggaattcctt gtaactggag    3720
ctcggagctg caccgagggc aaccaggaca gctgtgtgtg cagacctcat gtgttgggtt    3780
ctctcccctc cttcctgttc ctcttatata ccagtttatc cccattcttt tttttttct    3840
tactccaaaa taaatcaagg ctgcaatgca gctggtgctg ttcagattct accatcaggt    3900
gctataagtg tttgggattg agcatcatac tggaaagcaa acacctttcc tccagctcca    3960
gaattccttg tctctgaatg actctgtctt gtgggtgtct gacagtggcg acgatgaaca    4020
tgccgttggt tttattggca gtgggcacaa ggaggtgaga agtggtggta aaaggagcgg    4080
agtgctgaag cagagagcag atttaatata gtaacattaa cagtgtattt aattgacatt    4140
tcttttttgt aatgtgacga tatgtggaca agaagaagaa tgcaggttta agaagttaat    4200
atttataaaa tgtgaaagac acagttacta ggataacttt tttgtgggtg ggcttggga     4260
gatggggtgg ggtgggttaa ggggtcccat tttgtttctt tggatttggg gtgggggtcc    4320
tggccaagaa ctcagtcatt tttctgtgta ccaggttgcc taaatcatgt gcagatggtt    4380
ctaaaaaaaa aaaaaaaaa aaaaaaaaaa ggaaaaaaaa aaagaaaaag aaaacgtgtg    4440
cattttgtat aatggccaga actttgtcgt gtgacagtat tagcactgcc tcagttaaag    4500
gtttaatttt tgtttaaacc tagacgtgca acaaaagttt taccacagtc tgcacttgca    4560
gaagaaagaa aaaaattcaa accacatgtt tattttttt ttgcctacct cattgttctt     4620
aatgcattga gaggtgattt agtttatatg ttttggaag aaaccattaa tgtttaattt     4680
aatcttaata ccaaaacgac cagattgaag tttgactttt attgtcacaa atcagcaggc    4740
acaagaactg tccatgaaga tgggaaatag ccttaaggct gatgcagttt acttacaagt    4800
ttagaaacca gaatgctttg ttttaccag attcaccatt agaggttgat ggggcaactg     4860
cagcccatga cacaagatct cattgttctc gatgtagagg ggttggtagc agacaggtgg    4920
ttacattaga atagtcacac aaactgttca gtgttgcagg aaccttttct tgggggtggg    4980
ggagtttccc ttttctaaaa atgcaatgca ctaaaactat tttaagaatg tagttaattc    5040
tgcttattca taaagtgggc atcttctgtg ttttaggtgt aatatcgaag tcctggcttt    5100
tctcgttttc tcacttgctc tcttgttctc tgttttttta aaccaatttt actttatgaa    5160
tatattcatg acatttgtaa taaatgtctt gagaaagaat ttgtttcatg gcttcatggt    5220
catcactcaa gctcccgtaa ggatattacc gtctcaggaa aggatcagga ctccatgtca    5280
cagtcctgcc atcttacttt cctcttgtcg agttctgagt ggaaataact gcattatggc    5340
tgctttaacc tcagtcatca aaagaaactt gctgttttt aggcttgatc tttttccttt     5400
gtggttaatt ttcctgtata ttgtgaaaat ggggattt ccctctgctc ccacccacct      5460
aaacacagca gccatttgta cctgtttgct tcccatccca cttggcaccc actctgacct    5520
cttgtcagtt tcctgttcct ggttccatct ttttgaaaaa ggccctcctt tgagctacaa    5580
acatctggta agacaagtac atccactcat gaatgcagac acagcagctg gtggttttgt    5640
gtatacctgt aaagacaagc tgagaagctt acttttggg gaagtaaaag aagatggaaa     5700
tggatgtttc atttgtatga gtttggagca gtgctgaagg ccaaagccgc ctactggttt    5760
gtagttaacc tagagaaggt tgaaaaatta atcctacctt taaagggatt tgaggtaggc    5820
```

```
tggattccat cgccacagga ctttagttag aattaaattc ctgcttgtaa tttatatcca    5880
tgtttaggct tttcataaga tgaaacatgc cacagtgaac acactcgtgt acatatcaag    5940
agaagaagga aaggcacagg tggagaacag taaaaggtgg gcagatgtct ttgaagaaat    6000
gctcaatgtc tgatgctaag tgggagaagg cagagaacaa aggatgtggc ataatggtct    6060
taacattatc caaagacttg aagctccatg tctgtaagtc aaatgttaca caaaaaaaa    6120 tgcaaatggt gtttcattgg aattaccaag tgcttagaac ttgctggctt tcccataggt    6180
ggtaaagggg tctgagctca caccgagttg tgcttggctt gcttgtgcag ctccaggcac    6240
ccggtgggca ctctggtggt gtttgtggtg aactgaattg aatccattgt tgggcttaag    6300
ttactgaaat tggaacaccc tttgtccttc tcggcggggg cttcctggtc tgtgctttac    6360
ttggcttttt tccttcccgt cttagcctca ccccttgtc aaccagattg agttgctata    6420
gcttgatgca gggacccagt gaagtttctc cgttaaagat tgggagtcgt cgaaatgttt    6480
agattctttt aggaaaggaa ttattttccc ccctttaca gggtagtaac ttctccacag    6540
aagtgccaat atggcaaaat tacacaagaa aacagtattg caatgacacc attacataag    6600
gaacattgaa ctgttagagg agtgctcttc caaacaaaac aaaaatgtct ctaggtttag    6660
tcagagcttt cacaagtaat aacctttctg tattaaaatc agagtaaccc tttctgtatt    6720
gagtgcagtg tttttactc ttttctcatg cacatgttac gttggagaaa atgtttacaa    6780
aaatggtttt gttacactaa tgcgcaccac atatttatgg tttattttaa gtgacttttt    6840
atgggttatt taggttttcg tcttagttgt agcacactta ccctaatttt gccaattatt    6900
aatttgctaa atagtaatac aaatgacaaa ctgcattaaa tttactaatt ataaaagctg    6960
caaagcagac tggtggcaag tacacagccc ttttttttgc agtgctaact tgtctactgt    7020
gtattatgaa aattactgtt gtccccccac cctttttttcc ttaaataaag taaaatgac    7080 acctaaaaaa aaaaaaaaa aa                                              7102
```

<210> SEQ ID NO 7
<211> LENGTH: 1239
<212> TYPE: PRT
<213> ORGANISM: Homo sapiens

<400> SEQUENCE: 7

Met Ala Asn Asp Ser Pro Ala Lys Ser Leu Val Asp Ile Asp Leu Ser
 1               5                  10                  15

Ser Leu Arg Asp Pro Ala Gly Ile Phe Glu Leu Val Glu Val Val Gly
            20                  25                  30

Asn Gly Thr Tyr Gly Gln Val Tyr Lys Gly Arg His Val Lys Thr Gly
        35                  40                  45

Gln Leu Ala Ala Ile Lys Val Met Asp Val Thr Glu Asp Glu Glu Glu
    50                  55                  60

Glu Ile Lys Leu Glu Ile Asn Met Leu Lys Lys Tyr Ser His His Arg
65                  70                  75                  80

Asn Ile Ala Thr Tyr Tyr Gly Ala Phe Ile Lys Ser Pro Pro Gly
            85                  90                  95

His Asp Asp Gln Leu Trp Leu Val Met Glu Phe Cys Gly Ala Gly Ser
           100                 105                 110

Ile Thr Asp Leu Val Lys Asn Thr Lys Gly Asn Thr Leu Lys Glu Asp
       115                 120                 125

Trp Ile Ala Tyr Ile Ser Arg Glu Ile Leu Arg Gly Leu Ala His Leu
   130                 135                 140

```
His Ile His His Val Ile His Arg Asp Ile Lys Gly Gln Asn Val Leu
145                 150                 155                 160

Leu Thr Glu Asn Ala Glu Val Lys Leu Val Asp Phe Gly Val Ser Ala
        165                 170                 175

Gln Leu Asp Arg Thr Val Gly Arg Arg Asn Thr Phe Ile Gly Thr Pro
            180                 185                 190

Tyr Trp Met Ala Pro Glu Val Ile Ala Cys Asp Glu Asn Pro Asp Ala
        195                 200                 205

Thr Tyr Asp Tyr Arg Ser Asp Leu Trp Ser Cys Gly Ile Thr Ala Ile
            210                 215                 220

Glu Met Ala Glu Gly Ala Pro Pro Leu Cys Asp Met His Pro Met Arg
225                 230                 235                 240

Ala Leu Phe Leu Ile Pro Arg Asn Pro Pro Arg Leu Lys Ser Lys
        245                 250                 255

Lys Trp Ser Lys Lys Phe Phe Ser Phe Ile Glu Gly Cys Leu Val Lys
            260                 265                 270

Asn Tyr Met Gln Arg Pro Ser Thr Glu Gln Leu Leu Lys His Pro Phe
        275                 280                 285

Ile Arg Asp Gln Pro Asn Glu Arg Gln Val Arg Ile Gln Leu Lys Asp
    290                 295                 300

His Ile Asp Arg Thr Arg Lys Lys Arg Gly Glu Lys Asp Glu Thr Glu
305                 310                 315                 320

Tyr Glu Tyr Ser Gly Ser Glu Glu Glu Glu Val Pro Glu Gln
            325                 330                 335

Glu Gly Glu Pro Ser Ser Ile Val Asn Val Pro Gly Glu Ser Thr Leu
        340                 345                 350

Arg Arg Asp Phe Leu Arg Leu Gln Gln Glu Asn Lys Glu Arg Ser Glu
            355                 360                 365

Ala Leu Arg Arg Gln Gln Leu Leu Gln Glu Gln Leu Arg Glu Gln
        370                 375                 380

Glu Glu Tyr Lys Arg Gln Leu Leu Ala Glu Arg Gln Lys Arg Ile Glu
385                 390                 395                 400

Gln Gln Lys Glu Gln Arg Arg Leu Glu Glu Gln Gln Arg Arg Glu
            405                 410                 415

Arg Glu Ala Arg Arg Gln Gln Glu Arg Glu Gln Arg Arg Glu Gln
        420                 425                 430

Glu Glu Lys Arg Arg Leu Glu Glu Leu Glu Arg Arg Lys Glu Glu
            435                 440                 445

Glu Glu Arg Arg Arg Ala Glu Glu Lys Arg Arg Val Glu Arg Glu
        450                 455                 460

Gln Glu Tyr Ile Arg Arg Gln Leu Glu Glu Gln Arg His Leu Glu
465                 470                 475                 480

Val Leu Gln Gln Gln Leu Leu Gln Gln Ala Met Leu Leu Glu Cys
            485                 490                 495

Arg Trp Arg Glu Met Glu Glu His Arg Gln Ala Glu Arg Leu Gln Arg
        500                 505                 510

Gln Leu Gln Gln Glu Gln Ala Tyr Leu Leu Ser Leu Gln His Asp His
            515                 520                 525

Arg Arg Pro His Pro Gln His Ser Gln Gln Pro Pro Pro Gln Gln
        530                 535                 540

Glu Arg Ser Lys Pro Ser Phe His Ala Pro Glu Pro Lys Ala His Tyr
545                 550                 555                 560

Glu Pro Ala Asp Arg Ala Arg Glu Val Glu Asp Arg Phe Arg Lys Thr
```

-continued

```
                565                 570                 575
Asn His Ser Ser Pro Glu Ala Gln Ser Lys Gln Thr Gly Arg Val Leu
                580                 585                 590

Glu Pro Pro Val Pro Ser Arg Ser Glu Ser Phe Ser Asn Gly Asn Ser
                595                 600                 605

Glu Ser Val His Pro Ala Leu Gln Arg Pro Ala Glu Pro Gln Val Pro
                610                 615                 620

Val Arg Thr Thr Ser Arg Ser Pro Val Leu Ser Arg Arg Asp Ser Pro
625                 630                 635                 640

Leu Gln Gly Ser Gly Gln Gln Asn Ser Gln Ala Gly Gln Arg Asn Ser
                645                 650                 655

Thr Ser Ile Glu Pro Arg Leu Leu Trp Glu Arg Val Glu Lys Leu Val
                660                 665                 670

Pro Arg Pro Gly Ser Gly Ser Ser Ser Gly Ser Ser Asn Ser Gly Ser
                675                 680                 685

Gln Pro Gly Ser His Pro Gly Ser Gln Ser Gly Ser Gly Glu Arg Phe
                690                 695                 700

Arg Val Arg Ser Ser Ser Lys Ser Glu Gly Ser Pro Ser Gln Arg Leu
705                 710                 715                 720

Glu Asn Ala Val Lys Lys Pro Glu Asp Lys Glu Val Phe Arg Pro
                725                 730                 735

Leu Lys Pro Ala Asp Leu Thr Ala Leu Ala Lys Glu Leu Arg Ala Val
                740                 745                 750

Glu Asp Val Arg Pro Pro His Lys Val Thr Asp Tyr Ser Ser Ser Ser
                755                 760                 765

Glu Glu Ser Gly Thr Thr Asp Glu Glu Asp Asp Val Glu Gln Glu
                770                 775                 780

Gly Ala Asp Glu Ser Thr Ser Gly Pro Glu Asp Thr Arg Ala Ala Ser
785                 790                 795                 800

Ser Leu Asn Leu Ser Asn Gly Glu Thr Glu Ser Val Lys Thr Met Ile
                805                 810                 815

Val His Asp Asp Val Glu Ser Glu Pro Ala Met Thr Pro Ser Lys Glu
                820                 825                 830

Gly Thr Leu Ile Val Arg Gln Thr Gln Ser Ala Ser Ser Thr Leu Gln
                835                 840                 845

Lys His Lys Ser Ser Ser Phe Thr Pro Phe Ile Asp Pro Arg Leu
                850                 855                 860

Leu Gln Ile Ser Pro Ser Ser Gly Thr Thr Val Thr Ser Val Val Gly
865                 870                 875                 880

Phe Ser Cys Asp Gly Met Arg Pro Glu Ala Ile Arg Gln Asp Pro Thr
                885                 890                 895

Arg Lys Gly Ser Val Val Asn Val Asn Pro Thr Asn Thr Arg Pro Gln
                900                 905                 910

Ser Asp Thr Pro Glu Ile Arg Lys Tyr Lys Lys Arg Phe Asn Ser Glu
                915                 920                 925

Ile Leu Cys Ala Ala Leu Trp Gly Val Asn Leu Leu Val Gly Thr Glu
                930                 935                 940

Ser Gly Leu Met Leu Leu Asp Arg Ser Gly Gln Gly Lys Val Tyr Pro
945                 950                 955                 960

Leu Ile Asn Arg Arg Arg Phe Gln Gln Met Asp Val Leu Glu Gly Leu
                965                 970                 975

Asn Val Leu Val Thr Ile Ser Gly Lys Lys Asp Lys Leu Arg Val Tyr
                980                 985                 990
```

```
Tyr Leu Ser Trp Leu Arg Asn Lys Ile Leu His Asn Asp Pro Glu Val
        995                 1000                1005

Glu Lys Lys Gln Gly Trp Thr Thr Val Gly Asp Leu Glu Gly Cys Val
    1010                1015                1020

His Tyr Lys Val Val Lys Tyr Glu Arg Ile Lys Phe Leu Val Ile Ala
1025                1030                1035                1040

Leu Lys Ser Ser Val Glu Val Tyr Ala Trp Ala Pro Lys Pro Tyr His
        1045                1050                1055

Lys Phe Met Ala Phe Lys Ser Phe Gly Glu Leu Val His Lys Pro Leu
        1060                1065                1070

Leu Val Asp Leu Thr Val Glu Gly Gln Arg Leu Lys Val Ile Tyr
        1075                1080                1085

Gly Ser Cys Ala Gly Phe His Ala Val Asp Val Asp Ser Gly Ser Val
        1090                1095                1100

Tyr Asp Ile Tyr Leu Pro Thr His Ile Gln Cys Ser Ile Lys Pro His
1105                1110                1115                1120

Ala Ile Ile Ile Leu Pro Asn Thr Asp Gly Met Glu Leu Leu Val Cys
        1125                1130                1135

Tyr Glu Asp Glu Gly Val Tyr Val Asn Thr Tyr Gly Arg Ile Thr Lys
        1140                1145                1150

Asp Val Val Leu Gln Trp Gly Glu Met Pro Thr Ser Val Ala Tyr Ile
        1155                1160                1165

Arg Ser Asn Gln Thr Met Gly Trp Gly Glu Lys Ala Ile Glu Ile Arg
        1170                1175                1180

Ser Val Glu Thr Gly His Leu Asp Gly Val Phe Met His Lys Arg Ala
1185                1190                1195                1200

Gln Arg Leu Lys Phe Leu Cys Glu Arg Asn Asp Lys Val Phe Phe Ala
        1205                1210                1215

Ser Val Arg Ser Gly Gly Ser Ser Gln Val Tyr Phe Met Thr Leu Gly
        1220                1225                1230

Arg Thr Ser Leu Leu Ser Trp
        1235

<210> SEQ ID NO 8
<211> LENGTH: 7183
<212> TYPE: DNA
<213> ORGANISM: Homo sapiens

<400> SEQUENCE: 8 ggaaatggc gaacgactcc cctgcaaaaa gtctggtgga catcgacctc tcctccctgc        60
gggatcctgc tgggattttt gagctggtgg aagtggttgg aaatggcacc tatggacaag     120
tctataaggg tcgacatgtt aaaacgggtc agttggcagc catcaaagtt atggatgtca     180
ctgaggatga agaggaagaa atcaaactgg agataaatat gctaaagaaa tactctcatc     240
acagaaacat tgcaacatat tatggtgctt tcatcaaaaa gagccctcca ggacatgatg     300
accaactctg gcttgttatg gagttctgtg gggctgggtc cattacagac cttgtgaaga     360
acaccaaagg gaacacactc aaagaagact ggatcgctta catctccaga gaaatcctga     420
ggggactggc acatcttcac attcatcatg tgattcaccg ggatatcaag gccagaatg     480 tgttgctgac tgagaatgca gaggtgaaac ttgttgactt tggtgtgagt gctcagctgg     540
acaggactgt ggggcggaga aatacgttca taggcactcc ctactggatg gctcctgagg     600
tcatcgcctg tgatgagaac ccagatgcca cctatgatta cagaagtgat ctttggtctt     660
```

```
gtggcattac agccattgag atggcagaag gtgctccccc tctctgtgac atgcatccaa    720
tgagagcact gtttctcatt cccagaaacc ctcctccccg gctgaagtca aaaaaatggt    780
cgaagaagtt ttttagtttt atagaagggt gcctggtgaa gaattacatg cagcggccct    840
ctacagagca gcttttgaaa catccttttta tagggatca gccaaatgaa aggcaagtta    900
gaatccagct taaggatcat atagatcgta ccaggaagaa gagaggcgag aaagatgaaa    960
ctgagtatga gtacagtggg agtgaggaag aagaggagga agtgcctgaa caggaaggag   1020
agccaagttc cattgtgaac gtgcctggtg agtctactct tcgccgagat ttcctgagac   1080
tgcagcagga gaacaaggaa cgttccgagg ctcttcggag acaacagtta ctacaggagc   1140
aacagctccg ggagcaggaa gaatataaaa ggcaactgct ggcagagaga cagaagcgga   1200
ttgagcagca gaaagaacag aggcgacggc tagaagagca acaaggagag agcgggaag    1260
ctagaaggca gcaggaacgt gaacagcgaa ggagagaaca agaagaaaag aggcgtctag   1320
aggagttgga gagaaggcgc aaagaagaag aggagaggag acgggcagaa gaagaaaaga   1380
ggagagttga aagagaacag gagtatatca ggcgacagct agaagaggag cagcggcact   1440
tggaagtcct tcagcagcag ctgctccagg agcaggccat gttactggag tgccgatggc   1500
gggagatgga ggagcaccgg caggcagaga ggctccagag gcagttgcaa caagaacaag   1560
catatctcct gtctctacag catgaccata ggaggccgca cccgcagcac tcgcagcagc   1620
cgccaccacc gcagcaggaa aggagcaagc caagcttcca tgctcccgag cccaaagccc   1680
actacgagcc tgctgaccga gcgcgagagg tggaagatag atttaggaaa actaaccaca   1740
gctcccctga agcccagtct aagcagacag gcagagtatt ggagccacca gtgccttccc   1800
gatcagagtc ttttttccaat ggcaactccg agtctgtgca tcccgccctg cagagaccag   1860
cggagccaca ggttcctgtg agaacaacat ctcgctcccc tgttctgtcc cgtcgagatt   1920
ccccactgca gggcagtggg cagcagaata gccaggcagg acagagaaac tccaccagta   1980
ttgagcccag gcttctgtgg gagagagtgg agaagctggt gcccgacctt ggcagtggca   2040
gctcctcagg gtccagcaac tcaggatccc agcccgggtc tcaccctggg tctcagagtg   2100
gctccgggga acgcttcaga gtgagatcat catccaagtc tgaaggctct ccatctcagc   2160
gcctggaaaa tgcagtgaaa aaacctgaag ataaaaagga agttttcaga cccctcaagc   2220
ctgctgatct gaccgcactg gccaaagagc ttcgagcagt ggaagatgta cggccacctc   2280
acaaagtaac ggactactcc tcatccagtg aggagtcggg gacgacggat gaggaggacg   2340
acgatgtgga gcaggaaggg gctgacgagt ccacctcagg accagaggac accagagcag   2400
cgtcatctct gaatttgagc aatggtgaaa cggaatctgt gaaaaccatg attgtccatg   2460
atgatgtaga aagtgagccg gccatgaccc catccaagga gggcactcta atcgtccgcc   2520
agactcagtc cgctagtagc acactccaga aacacaaatc ttcctcctcc tttacacctt   2580
ttatagaccc cagattacta cagatttctc catctagcgg aacaacagtg acatctgtgg   2640
tgggattttc ctgtgatggg atgagaccag aagccataag gcaagatcct acccggaaag   2700
gctcagtggt caatgtgaat cctaccaaca ctaggccaca gagtgacacc ccggagattc   2760
gtaaatacaa gaagagggtttt aactctgaga ttctgtgtgc tgccttatgg ggagtgaatt   2820
tgctagtggg tacagagagt ggcctgatgc tgctggacag aagtggccaa gggaaggtct   2880
atccctctta tcaaccgaaga cgatttcaac aaatggacgt acttgagggc ttgaatgtct   2940
tggtgacaat atctggcaaa aaggataagt tacgtgtcta ctatttgtcc tggttaagaa   3000
ataaaatact tcacaatgat ccagaagttg agaagaagca gggatggaca accgtagggg   3060
```

```
atttggaagg atgtgtacat tataaagttg taaaatatga aagaatcaaa tttctggtga    3120 ttgcttttgaa gagttctgtg gaagtctatg cgtgggcacc aaagccatat cacaaattta   3180
tggcctttaa gtcatttgga gaattggtac ataagccatt actggtggat ctcactgttg    3240
aggaaggcca gaggttgaaa gtgatctatg gatcctgtgc tggattccat gctgttgatg    3300
tggattcagg atcagtctat gacatttatc taccaacaca tatccagtgt agcatcaaac    3360
cccatgcaat catcatcctc cccaatacag atggaatgga gcttctggtg tgctatgaag    3420
atgagggggt ttatgtaaac acatatggaa ggatcaccaa ggatgtagtt ctacagtggg    3480
gagagatgcc tacatcagta gcatatattc gatccaatca gacaatgggc tggggagaga    3540
aggccataga gatccgatct gtggaaactg gtcacttgga tggtgtgttc atgcacaaaa    3600
gggctcaaag actaaaattc ttgtgtgaac gcaatgacaa ggtgttcttt gcctctgttc    3660
ggtctggtgg cagcagtcag gtttatttca tgaccttagg caggacttct cttctgagct    3720
ggtagaagca gtgtgatcca ggattactg gcctccagag tcttcaagat cctgagaact     3780
tggaattcct tgtaactgga gctcggagct gcaccgaggg caaccaggac agctgtgtgt    3840
gcagacctca tgtgttgggt tctctcccct ccttcctgtt cctcttatat accagtttat    3900
ccccattctt ttttttttc ttactccaaa ataaatcaag gctgcaatgc agctggtgct      3960
gttcagattc taccatcagg tgctataagt gtttgggatt gagcatcata ctggaaagca    4020
aacacctttc ctccagctcc agaattcctt gtctctgaat gactctgtct tgtgggtgtc    4080
tgacagtggc gacgatgaac atgccgttgg ttttattggc agtgggcaca aggaggtgag    4140
aagtggtggt aaaaggagcg gagtgctgaa gcagagagca gatttaatat agtaacatta    4200
acagtgtatt taattgacat ttcttttttg taatgtgacg atatgtggac aaagaagaag    4260
atgcaggttt aagaagttaa tatttataaa atgtgaaaga cacagttact aggataactt    4320
ttttgtgggt ggggcttggg agatgggggtg gggtgggtta aggggtccca ttttgttttct   4380 ttggatttgg ggtgggggtc ctggccaaga actcagtcat ttttctgtgt accaggttgc    4440
ctaaatcatg tgcagatggt tctaaaaaaa aaaaaaaaa aaaaaaaaaa aggaaaaaaa     4500 aaagaaaaa gaaaacgtgt gcattttgta taatggccag aactttgtcg tgtgacagta    4560
ttagcactgc ctcagttaaa ggtttaattt ttgtttaaac ctagacgtgc aacaaaagtt    4620
ttaccacagt ctgcacttgc agaagaaaga aaaaaattca aaccacatgt ttattttttt    4680
tttgcctacc tcattgttct taatgcattg agaggtgatt tagtttatat gttttttggaa   4740 gaaaccatta atgtttaatt taatcttaat accaaaacga ccagattgaa gtttgacttt    4800
tattgtcaca aatcagcagg cacaagaact gtccatgaag atgggaaata gccttaaggc    4860
tgatgcagtt tacttacaag tttagaaacc agaatgcttt gttttttacca gattcaccat    4920 tagaggttga tggggcaact gcagcccatg acacaagatc tcattgttct cgatgtagag    4980
gggttggtag cagacaggtg gttacattag aatagtcaca caaactgttc agtgttgcag    5040
gaaccttttc ttgggggtgg gggagtttcc cttttctaaa aatgcaatgc actaaaacta    5100
ttttaagaat gtagttaatt ctgcttattc ataaagtggg catcttctgt gttttaggtg    5160
taatatcgaa gtcctggctt ttctcgtttt ctcacttgct ctcttgttct ctgttttttt    5220
aaaccaattt tactttatga atatattcat gacatttgta ataaatgtct tgagaaagaa    5280
tttgtttcat ggcttcatgg tcatcactca agctcccgta aggatattac cgtctcagga    5340
aaggatcagg actccatgtc acagtcctgc catcttactt tcctcttgtc gagttctgag    5400
```

| | | |
|---|---|---|
| tggaaataac tgcattatgg ctgctttaac ctcagtcatc aaaagaaact tgctgttttt | 5460 | |
| taggcttgat cttttccctt tgtggttaat tttcctgtat attgtgaaaa tgggggattt | 5520 | |
| tccctctgct cccacccacc taaacacagc agccatttgt acctgtttgc ttcccatccc | 5580 | |
| acttggcacc cactctgacc tcttgtcagt ttcctgttcc tggttccatc ttttgaaaa | 5640 | |
| aggccctcct ttgagctaca aacatctggt aagacaagta catccactca tgaatgcaga | 5700 | |
| cacagcagct ggtggttttg tgtatacctg taaagacaag ctgagaagct tactttttgg | 5760 | |
| ggaagtaaaa gaagatggaa atggatgttt catttgtatg agtttggagc agtgctgaag | 5820 | |
| gccaaagccg cctactggtt tgtagttaac ctagagaagg ttgaaaaatt aatcctacct | 5880 | |
| ttaaagggat tgaggtagg ctggattcca tcgccacagg actttagtta gaattaaatt | 5940 | |
| cctgcttgta atttatatcc atgtttaggc ttttcataag atgaaacatg ccacagtgaa | 6000 | |
| cacactcgtg tacatatcaa gagaagaagg aaaggcacag gtggagaaca gtaaaaggtg | 6060 | |
| ggcagatgtc tttgaagaaa tgctcaatgt ctgatgctaa gtgggagaag cagagaaca | 6120 | |
| aaggatgtgg cataatggtc ttaacattat ccaaagactt gaagctccat gtctgtaagt | 6180 | |
| caaatgttac acaaaaaaaa atgcaaatgg tgtttcattg gaattaccaa gtgcttagaa | 6240 | |
| cttgctggct ttcccatagg tggtaaaggg gtctgagctc acaccgagtt gtgcttggct | 6300 | |
| tgcttgtgca gctccaggca cccggtgggc actctggtgg tgtttgtggt gaactgaatt | 6360 | |
| gaatccattg ttgggcttaa gttactgaaa ttggaacacc ctttgtcctt ctcggcgggg | 6420 | |
| gcttcctggt ctgtgctta cttggctttt ttccttcccg tcttagcctc accccttgt | 6480 | |
| caaccagatt gagttgctat agcttgatgc agggacccag tgaagtttct ccgttaaaga | 6540 | |
| ttgggagtcg tcgaaatgtt tagattcttt taggaaagga attattttcc cccttttac | 6600 | |
| agggtagtaa cttctccaca gaagtgccaa tatggcaaaa ttacacaaga aaacagtatt | 6660 | |
| gcaatgacac cattacataa ggaacattga actgttagag gagtgctctt ccaaacaaaa | 6720 | |
| caaaaatgtc tctaggttta gtcagagctt tcacaagtaa taacctttct gtattaaaat | 6780 | |
| cagagtaacc ctttctgtat tgagtgcagt gtttttact cttttctcat gcacatgtta | 6840 | |
| cgttggagaa aatgtttaca aaaatggttt tgttacacta atgcgcacca catatttatg | 6900 | |
| gtttatttta agtgactttt tatgggttat ttaggttttc gtcttagttg tagcacactt | 6960 | |
| accctaattt tgccaattat taatttgcta aatagtaata caaatgacaa actgcattaa | 7020 | |
| atttactaat tataaaagct gcaaagcaga ctggtggcaa gtacacagcc cttttttttg | 7080 | |
| cagtgctaac ttgtctactg tgtattatga aaattactgt tgtccccca ccctttttc | 7140 | |
| cttaaataaa gtaaaaatga cacctaaaaa aaaaaaaaa aaa | 7183 | |

<210> SEQ ID NO 9
<211> LENGTH: 1235
<212> TYPE: PRT
<213> ORGANISM: Homo sapiens

<400> SEQUENCE: 9

```
Met Ala Asn Asp Ser Pro Ala Lys Ser Leu Val Asp Ile Asp Leu Ser
 1               5                  10                  15

Ser Leu Arg Asp Pro Ala Gly Ile Phe Glu Leu Val Glu Val Val Gly
            20                  25                  30

Asn Gly Thr Tyr Gly Gln Val Tyr Lys Gly Arg His Val Lys Thr Gly
        35                  40                  45

Gln Leu Ala Ala Ile Lys Val Met Asp Val Thr Glu Asp Glu Glu Glu
    50                  55                  60
```

```
Glu Ile Lys Leu Glu Ile Asn Met Leu Lys Lys Tyr Ser His His Arg
65                  70                  75                  80

Asn Ile Ala Thr Tyr Tyr Gly Ala Phe Ile Lys Lys Ser Pro Pro Gly
                85                  90                  95

His Asp Asp Gln Leu Trp Leu Val Met Glu Phe Cys Gly Ala Gly Ser
            100                 105                 110

Ile Thr Asp Leu Val Lys Asn Thr Lys Gly Asn Thr Leu Lys Glu Asp
        115                 120                 125

Trp Ile Ala Tyr Ile Ser Arg Glu Ile Leu Arg Gly Leu Ala His Leu
    130                 135                 140

His Ile His His Val Ile His Arg Asp Ile Lys Gly Gln Asn Val Leu
145                 150                 155                 160

Leu Thr Glu Asn Ala Glu Val Lys Leu Val Asp Phe Gly Val Ser Ala
                165                 170                 175

Gln Leu Asp Arg Thr Val Gly Arg Arg Asn Thr Phe Ile Gly Thr Pro
            180                 185                 190

Tyr Trp Met Ala Pro Glu Val Ile Ala Cys Asp Glu Asn Pro Asp Ala
        195                 200                 205

Thr Tyr Asp Tyr Arg Ser Asp Leu Trp Ser Cys Gly Ile Thr Ala Ile
    210                 215                 220

Glu Met Ala Glu Gly Ala Pro Pro Leu Cys Asp Met His Pro Met Arg
225                 230                 235                 240

Ala Leu Phe Leu Ile Pro Arg Asn Pro Pro Arg Leu Lys Ser Lys
                245                 250                 255

Lys Trp Ser Lys Lys Phe Phe Ser Phe Ile Glu Gly Cys Leu Val Lys
            260                 265                 270

Asn Tyr Met Gln Arg Pro Ser Thr Glu Gln Leu Leu Lys His Pro Phe
        275                 280                 285

Ile Arg Asp Gln Pro Asn Glu Arg Gln Val Arg Ile Gln Leu Lys Asp
    290                 295                 300

His Ile Asp Arg Thr Arg Lys Lys Arg Gly Glu Lys Asp Glu Thr Glu
305                 310                 315                 320

Tyr Glu Tyr Ser Gly Ser Glu Glu Glu Glu Glu Val Pro Glu Gln
                325                 330                 335

Glu Gly Glu Pro Ser Ser Ile Val Asn Val Pro Gly Glu Ser Thr Leu
            340                 345                 350

Arg Arg Asp Phe Leu Arg Leu Gln Gln Glu Asn Lys Glu Arg Ser Glu
        355                 360                 365

Ala Leu Arg Arg Gln Gln Leu Leu Gln Glu Gln Leu Arg Glu Gln
        370                 375                 380

Glu Glu Tyr Lys Arg Gln Leu Leu Ala Glu Arg Gln Lys Arg Ile Glu
385                 390                 395                 400

Gln Gln Lys Glu Gln Arg Arg Leu Glu Glu Gln Arg Arg Glu
            405                 410                 415

Arg Glu Ala Arg Arg Gln Gln Glu Glu Gln Arg Arg Glu Gln
        420                 425                 430

Glu Glu Lys Arg Arg Leu Glu Glu Leu Glu Arg Arg Lys Glu Glu
            435                 440                 445

Glu Glu Arg Arg Arg Ala Glu Glu Lys Arg Arg Val Glu Arg Glu
        450                 455                 460

Gln Glu Tyr Ile Arg Arg Gln Leu Glu Glu Gln Arg His Leu Glu
465                 470                 475                 480
```

-continued

```
Val Leu Gln Gln Gln Leu Leu Gln Glu Gln Ala Met Leu Leu His Asp
            485                 490                 495

His Arg Arg Pro His Pro Gln His Ser Gln Gln Pro Pro Pro Pro Gln
        500                 505                 510

Gln Glu Arg Ser Lys Pro Ser Phe His Ala Pro Glu Pro Lys Ala His
        515                 520                 525

Tyr Glu Pro Ala Asp Arg Ala Arg Glu Val Gln Trp Ser His Leu Ala
        530                 535                 540

Ser Leu Lys Asn Asn Val Ser Pro Val Ser Arg Ser His Ser Phe Ser
545                 550                 555                 560

Asp Pro Ser Pro Lys Phe Ala His His His Leu Arg Ser Gln Asp Pro
                565                 570                 575

Cys Pro Pro Ser Arg Ser Glu Val Leu Ser Gln Ser Ser Asp Ser Lys
            580                 585                 590

Ser Glu Ala Pro Asp Pro Thr Gln Lys Ala Trp Ser Arg Ser Asp Ser
        595                 600                 605

Asp Glu Val Pro Pro Arg Val Pro Val Arg Thr Thr Ser Arg Ser Pro
    610                 615                 620

Val Leu Ser Arg Arg Asp Ser Pro Leu Gln Gly Ser Gly Gln Gln Asn
625                 630                 635                 640

Ser Gln Ala Gly Gln Arg Asn Ser Thr Ser Ser Ile Glu Pro Arg Leu
                645                 650                 655

Leu Trp Glu Arg Val Glu Lys Leu Val Pro Arg Pro Gly Ser Gly Ser
            660                 665                 670

Ser Ser Gly Ser Ser Asn Ser Gly Ser Gln Pro Gly Ser His Pro Gly
        675                 680                 685

Ser Gln Ser Gly Ser Gly Glu Arg Phe Arg Val Arg Ser Ser Ser Lys
        690                 695                 700

Ser Glu Gly Ser Pro Ser Gln Arg Leu Glu Asn Ala Val Lys Lys Pro
705                 710                 715                 720

Glu Asp Lys Lys Glu Val Phe Arg Pro Leu Lys Pro Ala Gly Glu Val
                725                 730                 735

Asp Leu Thr Ala Leu Ala Lys Glu Leu Arg Ala Val Glu Asp Val Arg
            740                 745                 750

Pro Pro His Lys Val Thr Asp Tyr Ser Ser Ser Ser Glu Glu Ser Gly
        755                 760                 765

Thr Thr Asp Glu Glu Asp Asp Val Glu Gln Glu Gly Ala Asp Glu
        770                 775                 780

Ser Thr Ser Gly Pro Glu Asp Thr Arg Ala Ala Ser Ser Leu Asn Leu
785                 790                 795                 800

Ser Asn Gly Glu Thr Glu Ser Val Lys Thr Met Ile Val His Asp Asp
                805                 810                 815

Val Glu Ser Glu Pro Ala Met Thr Pro Ser Lys Glu Gly Thr Leu Ile
            820                 825                 830

Val Arg Gln Thr Gln Ser Ala Ser Ser Thr Leu Gln Lys His Lys Ser
        835                 840                 845

Ser Ser Ser Phe Thr Pro Phe Ile Asp Pro Arg Leu Leu Gln Ile Ser
        850                 855                 860

Pro Ser Ser Gly Thr Thr Val Thr Ser Val Val Gly Phe Ser Cys Asp
865                 870                 875                 880

Gly Met Arg Pro Glu Ala Ile Arg Gln Asp Pro Thr Arg Lys Gly Ser
                885                 890                 895

Val Val Asn Val Asn Pro Thr Asn Thr Arg Pro Gln Ser Asp Thr Pro
```

```
                    900             905                 910
        Glu Ile Arg Lys Tyr Lys Lys Arg Phe Asn Ser Glu Ile Leu Cys Ala
                915                 920                 925
        Ala Leu Trp Gly Val Asn Leu Val Gly Thr Glu Ser Gly Leu Met
                930                 935                 940
        Leu Leu Asp Arg Ser Gly Gln Gly Lys Val Tyr Pro Leu Ile Asn Arg
        945                 950                 955                 960
        Arg Arg Phe Gln Gln Met Asp Val Leu Glu Gly Leu Asn Val Leu Val
                            965                 970                 975
        Thr Ile Ser Gly Lys Lys Asp Lys Leu Arg Val Tyr Tyr Leu Ser Trp
                        980                 985                 990
        Leu Arg Asn Lys Ile Leu His Asn Asp Pro Glu Val Glu Lys Lys Gln
                    995                 1000                1005
        Gly Trp Thr Thr Val Gly Asp Leu Glu Gly Cys Val His Tyr Lys Val
                    1010                1015                1020
        Val Lys Tyr Glu Arg Ile Lys Phe Leu Val Ile Ala Leu Lys Ser Ser
        1025                1030                1035                1040
        Val Glu Val Tyr Ala Trp Ala Pro Lys Pro Tyr His Lys Phe Met Ala
                        1045                1050                1055
        Phe Lys Ser Phe Gly Glu Leu Val His Lys Pro Leu Leu Val Asp Leu
                    1060                1065                1070
        Thr Val Glu Glu Gly Gln Arg Leu Lys Val Ile Tyr Gly Ser Cys Ala
                    1075                1080                1085
        Gly Phe His Ala Val Asp Val Asp Ser Gly Ser Val Tyr Asp Ile Tyr
                    1090                1095                1100
        Leu Pro Thr His Ile Gln Cys Ser Ile Lys Pro His Ala Ile Ile Ile
        1105                1110                1115                1120
        Leu Pro Asn Thr Asp Gly Met Glu Leu Leu Val Cys Tyr Glu Asp Glu
                        1125                1130                1135
        Gly Val Tyr Val Asn Thr Tyr Gly Arg Ile Thr Lys Asp Val Val Leu
                        1140                1145                1150
        Gln Trp Gly Glu Met Pro Thr Ser Val Ala Tyr Ile Arg Ser Asn Gln
                    1155                1160                1165
        Thr Met Gly Trp Gly Glu Lys Ala Ile Glu Ile Arg Ser Val Glu Thr
            1170                1175                1180
        Gly His Leu Asp Gly Val Phe Met His Lys Arg Ala Gln Arg Leu Lys
        1185                1190                1195                1200
        Phe Leu Cys Glu Arg Asn Asp Lys Val Phe Phe Ala Ser Val Arg Ser
                        1205                1210                1215
        Gly Gly Ser Ser Gln Val Tyr Phe Met Thr Leu Gly Arg Thr Ser Leu
                    1220                1225                1230
        Leu Ser Trp
                1235

<210> SEQ ID NO 10
<211> LENGTH: 7544
<212> TYPE: DNA
<213> ORGANISM: Homo sapiens

<400> SEQUENCE: 10
gctcactcgc tcaactcggc gccgccgcgg ccccacgctc cgggcccgtc ctcgaggcgc      60
gcggcgcggg gcgcgggcgc cggggcctga ggcggcgggc gacgcccggg ggcctgacgg     120
ccggccccgc gccatggtgt gagcgccgcc gcccgtgcac gctccgtccg ccctccgcgc     180
```

```
ggcccggccg gcagagagcc ccgagcggcc cgagagcgca gccgagcccg ccgccgccgc    240
ccgcggcccc gcgaggagag taccgggccg gctcggctgc cgcgcgagga gcgcggtcgg    300
cggcctggtc tgcggctgag atacacagag cgacagagac atttattgtt atttgttttt    360
tggtggcaaa aagggaaaat ggcgaacgac tccctgcaa aaagtctggt ggacatcgac     420
ctctcctccc tgcgggatcc tgctgggatt tttgagctgg tggaagtggt tggaaatggc    480
acctatggac aagtctataa gggtcgacat gttaaaacgg gtcagttggc agccatcaaa    540
gttatggatg tcactgagga tgaagaggaa gaaatcaaac tggagataaa tatgctaaag    600
aaatactctc atcacagaaa cattgcaaca tattatggtg ctttcatcaa aaagagccct    660
ccaggacatg atgaccaact ctggcttgtt atggagttct gtgggctgg gtccattaca     720 gaccttgtga agaacaccaa agggaacaca ctcaaagaag actggatcgc ttacatctcc    780
agagaaatcc tgagggggact ggcacatctt cacattcatc atgtgattca ccgggatatc    840
aagggccaga atgtgttgct gactgagaat gcagaggtga acttgttga ctttggtgtg     900 agtgctcagc tggacaggac tgtggggcgg agaaatacgt tcataggcac tccctactgg    960
atggctcctg aggtcatcgc ctgtgatgag aacccagatg ccacctatga ttacagaagt   1020
gatctttggt cttgtggcat tacagccatt gagatggcag aaggtgctcc ccctctctgt   1080
gacatgcatc aaatgagagc actgtttctc attcccagaa accctcctcc ccggctgaag   1140
tcaaaaaaat ggtcgaagaa gttttttagt tttataagaa ggtgcctggt gaagaattac   1200
atgcagcggc cctctacaga gcagcttttg aaacatcctt ttataaggga tcagccaaat   1260
gaaaggcaag ttagaatcca gcttaaggat catatagatc gtaccaggaa gaagagaggc   1320
gagaaagatg aaactgagta tgagtacagt gggagtgagg aagaagagga ggaagtgcct   1380
gaacaggaag gagagccaag ttccattgtg aacgtgcctg gtgagtctac tcttcgccga   1440
gatttcctga gactgcagca ggagaacaag gaacgttccg aggctcttcg gagacaacag   1500
ttactacagg agcaacagct ccgggagcag gaagaatata aaaggcaact gctggcagag   1560
agacagaagc ggattgagca gcagaaagaa cagaggcgac ggctagaaga gcaacaaagg   1620
agagagcggg aagctagaag gcagcaggaa cgtgaacagc gaaggagaga acaagaagaa   1680
aagaggcgtc tagaggagtt ggagagaagg cgcaaagaag aagaggagag gagacgggca   1740
gaagaagaaa agaggagagt tgaaagagaa caggagtata tcaggcgaca gctagaagag   1800
gagcagcggc acttggaagt ccttcagcag cagctgctcc aggagcaggc catgttactg   1860
catgaccata ggaggccgca cccgcagcac tcgcagcagc cgccaccacc gcagcaggaa   1920
aggagcaagc caagcttcca tgctcccgag cccaaagccc actacgagcc tgctgaccga   1980
gcgcgagagg tacagtggtc ccacctggca tctctcaaga caatgtttc ccctgtctcg    2040 cgatcccatt ccttcagtga cccttctccc aaatttgcac accaccatct tcgttctcag   2100
gacccatgtc caccttcccg cagtgaggtg ctcagtcaga gctctgactc taagtcagag   2160
gcgcctgacc ctacccaaaa ggcttggtct agatcagaca gtgacgaggt gcctccaagg   2220
gttcctgtga gaacaacatc tcgctccct gttctgtccc gtcgagattc cccactgcag    2280
ggcagtgggc agcagaatag ccaggcagga cagagaaact ccaccagcag tattgagccc   2340
aggcttctgt gggagagagt ggagaagctg gtgcccagac ctggcagtgg cagctcctca   2400
gggtccagca actcaggatc ccagcccggg tctcaccctg ggtctcagag tggctccggg   2460
gaacgcttca gagtgagatc atcatccaag tctgaaggct ctccatctca gcgcctggaa   2520
aatgcagtga aaaaacctga agataaaaag gaagttttca gaccccctcaa gcctgctggc   2580
```

```
gaagtggatc tgaccgcact ggccaaagag cttcgagcag tggaagatgt acggccacct    2640
cacaaagtaa cggactactc ctcatccagt gaggagtcgg ggacgacgga tgaggaggac    2700
gacgatgtgg agcaggaagg ggctgacgag tccacctcag gaccagagga caccagagca    2760
gcgtcatctc tgaatttgag caatggtgaa acggaatctg tgaaaaccat gattgtccat    2820
gatgatgtag aaagtgagcc ggccatgacc ccatccaagg agggcactct aatcgtccgc    2880
cagactcagt ccgctagtag cacactccag aaacacaaat cttcctcctc ctttacacct    2940
tttatagacc ccagattact acagatttct ccatctagcg gaacaacagt gacatctgtg    3000
gtgggatttt cctgtgatgg gatgagacca gaagccataa ggcaagatcc tacccggaaa    3060
ggctcagtgg tcaatgtgaa tcctaccaac actaggccac agagtgacac cccggagatt    3120
cgtaaataca agaagaggtt taactctgag attctgtgtg ctgccttatg gggagtgaat    3180
ttgctagtgg gtacagagag tggcctgatg ctgctggaca gaagtggcca agggaaggtc    3240
tatcctctta tcaaccgaag acgatttcaa caaatggacg tacttgaggg cttgaatgtc    3300
ttggtgacaa tatctggcaa aaaggataag ttacgtgtct actatttgtc ctggttaaga    3360
aataaaatac ttcacaatga tccagaagtt gagaagaagc agggatggac aaccgtaggg    3420
gatttggaag gatgtgtaca ttataaagtt gtaaaatatg aaagaatcaa atttctggtg    3480
attgctttga agagttctgt ggaagtctat gcgtgggcac caaagccata tcacaaattt    3540
atggccttta agtcatttgg agaattggta cataagccat tactggtgga tctcactgtt    3600
gaggaaggcc agaggttgaa agtgatctat ggatcctgtg ctggattcca tgctgttgat    3660
gtggattcag gatcagtcta tgacatttat ctaccaacac atatccagtg tagcatcaaa    3720
ccccatgcaa tcatcatcct ccccaataca gatggaatgg agcttctggt gtgctatgaa    3780
gatgaggggg tttatgtaaa cacatatgga aggatcacca aggatgtagt tctacagtgg    3840
ggagagatgc ctacatcagt agcatatatt cgatccaatc agacaatggg ctggggagag    3900
aaggccatag agatccgatc tgtggaaact ggtcacttgg atggtgtgtt catgcacaaa    3960
agggctcaaa gactaaaatt cttgtgtgaa cgcaatgaca aggtgttctt tgcctctgtt    4020
cggtctggtg gcagcagtca ggtttatttc atgaccttag gcaggacttc tcttctgagc    4080
tggtagaagc agtgtgatcc agggattact ggcctccaga gtcttcaaga tcctgagaac    4140
ttggaattcc ttgtaactgg agctcggagc tgcaccgagg caaccaggga cagctgtgtg    4200
tgcagacctc atgtgttggg ttctctcccc tccttcctgt tcctcttata taccagttta    4260
tccccattct tttttttttt cttactccaa aataaatcaa ggctgcaatg cagctggtgc    4320
tgttcagatt ctaccatcag gtgctataag tgtttgggat tgagcatcat actggaaagc    4380 aaacacccttt cctccagctc cagaattcct tgtctctgaa tgactctgtc ttgtgggtgt    4440
ctgacagtgg cgacgatgaa catgccgttg gttttattgg cagtgggcac aaggaggtga    4500
gaagtggtgg taaaaggagc ggagtgctga agcagagagc agatttaata tagtaacatt    4560
aacagtgtat ttaattgaca tttctttttt gtaatgtgac gatatgtgga caaagaagaa    4620
gatgcaggtt taagaagtta atatttataa aatgtgaaag acacagttac taggataact    4680
tttttgtggg tggggcttgg gagatggggt ggggtgggtt aagggtgtccc attttgtttc    4740 tttggatttg gggtgggggt cctggccaag aactcagtca tttttctgtg taccaggttg    4800
cctaaatcat gtgcagatgg ttctaaaaaa aaaaaaaaa aaaaaaaaa aaggaaaaaa    4860 aaaaagaaaa agaaaacgtg tgcattttgt ataatggcca gaactttgtc gtgtgacagt    4920
```

```
attagcactg cctcagttaa aggtttaatt tttgtttaaa cctagacgtg caacaaaagt    4980
tttaccacag tctgcacttg cagaagaaag aaaaaaattc aaaccacatg tttattttt     5040
ttttgcctac ctcattgttc ttaatgcatt gagaggtgat ttagtttata tgttttgga     5100
agaaaccatt aatgtttaat ttaatcttaa taccaaaacg accagattga agtttgactt    5160
ttattgtcac aaatcagcag gcacaagaac tgtccatgaa gatgggaaat agccttaagg    5220
ctgatgcagt ttacttacaa gtttagaaac cagaatgctt tgttttttacc agattcacca   5280
ttagaggttg atggggcaac tgcagcccat gacacaagat ctcattgttc tcgatgtaga    5340
ggggttggta gcagacaggt ggttacatta gaatagtcac acaaactgtt cagtgttgca    5400
ggaaccttt cttggggtg ggggagtttc ccttttctaa aaatgcaatg cactaaaact      5460
atttaagaa tgtagttaat tctgcttatt cataaagtgg gcatcttctg tgttttaggt     5520
gtaatatcga agtcctggct tttctcgttt tctcacttgc tctcttgttc tctgtttttt    5580
taaaccaatt ttactttatg aatatattca tgacatttgt aataaatgtc ttgagaaaga    5640
atttgtttca tggcttcatg gtcatcactc aagctcccgt aaggatatta ccgtctcagg    5700
aaaggatcag gactccatgt cacagtcctg ccatcttact ttcctcttgt cgagttctga    5760
gtggaaataa ctgcattatg gctgctttaa cctcagtcat caaaagaaac ttgctgtttt    5820
ttaggcttga tcttttttcct ttgtggttaa ttttcctgta tattgtgaaa atgggggatt   5880
ttccctctgc tcccacccac ctaaacacag cagccatttg tacctgtttg cttcccatcc    5940
cacttggcac ccactctgac ctcttgtcag tttcctgttc ctggttccat ctttttgaaa    6000
aaggccctcc tttgagctac aaacatctgg taagacaagt acatccactc atgaatgcag    6060
acacagcagc tggtggtttt gtgtataccct gtaaagacaa gctgagaagc ttactttttg   6120
gggaagtaaa agaagatgga aatggatgtt tcatttgtat gagtttggag cagtgctgaa    6180
ggccaaagcc gcctactggt ttgtagttaa cctagagaag gttgaaaaat taatcctacc    6240
tttaaaggga tttgaggtag gctggattcc atcgccacag gactttagtt agaattaaat    6300
tcctgcttgt aatttatatc catgtttagg cttttcataa gatgaaacat gccacagtga    6360
acacactcgt gtacatatca agagaagaag gaaaggcaca ggtggagaac agtaaaaggt    6420
gggcagatgt cttttgaagaa atgctcaatg tctgatgcta agtgggagaa ggcagagaac    6480
aaaggatgtg gcataatggt cttaacatta tccaaagact tgaagctcca tgtctgtaag   6540
tcaaatgtta cacaaaaaaa aatgcaaatg gtgtttcatt ggaattacca agtgcttaga    6600
acttgctggc tttcccatag gtggtaaagg ggtctgagct cacaccgagt tgtgcttggc    6660
ttgcttgtgc agctccaggc acccggtggg cactctggtg gtgtttgtgg tgaactgaat    6720
tgaatccatt gttgggctta agttactgaa attggaacac cctttgtcct tctcggcggg    6780
ggcttcctgg tctgtgcttt acttggcttt tttccttccc gtcttagcct cacccccttg    6840
tcaaccagat tgagttgcta tagcttgatg cagggaccca gtgaagtttc tccgttaaag    6900
attgggagtc gtcgaaatgt ttagattctt ttaggaaagg aattattttc ccccctttta    6960
cagggtagta acttctccac agaagtgcca atatggcaaa attacacaag aaaacagtat    7020
tgcaatgaca ccattacata aggaacattg aactgttaga ggagtgctct tccaaacaaa    7080
acaaaaatgt ctctaggttt agtcagagct ttcacaagta ataacctttc tgtattaaaa    7140
tcagagtaac cctttctgta ttgagtgcag tgtttttttac tcttttctca tgcacatgtt    7200
acgttggaga aaatgtttac aaaaatggtt ttgttacact aatgcgcacc acatatttat    7260
ggtttatttt aagtgacttt ttatgggtta tttaggtttt cgtcttagtt gtagcacact    7320
```

```
tacectaatt ttgccaatta ttaatttgct aaatagtaat acaaatgaca aactgcatta   7380
aatttactaa ttataaaagc tgcaaagcag actggtggca agtacacagc cctttttttt   7440
gcagtgctaa cttgtctact gtgtattatg aaaattactg ttgtccccc  acccttttt    7500 ccttaaataa agtaaaaatg acacctaaaa aaaaaaaaa  aaaa                    7544
```

<210> SEQ ID NO 11
<211> LENGTH: 1608
<212> TYPE: PRT
<213> ORGANISM: Canis lupus familiaris

<400> SEQUENCE: 11

```
Met Arg Glu Ala Ala Ala Ala Glu Leu Val Pro Pro Pro Ala Phe
 1               5                  10                  15

Ala Val Thr Pro Ala Ala Ala Met Glu Glu Pro Pro Pro Pro Pro
                20                  25                  30

Pro Gly Pro Glu Pro Glu Pro Glu Pro Glu Pro Glu Pro Arg Cys
            35                  40                  45

Arg Ala Ala Arg Gln Glu Cys Thr Val Gly Asp Ser Ala Cys Lys Asn
    50                  55                  60

Ser Glu Ser Asp Pro Glu Asp Phe Ser Asp Glu Ile Asn Thr Glu Asn
 65                 70                  75                  80

Leu Tyr Gly Thr Ser Pro Pro Ser Thr Pro Arg Gln Met Lys Arg Met
                85                  90                  95

Ser Thr Lys His Gln Arg Asn Asn Val Gly Lys Pro Ala Asn Arg Ser
            100                 105                 110

Gly Leu Lys Glu Lys Met Asn Ala Pro Asn Gln Pro Pro His Lys Asp
        115                 120                 125

Thr Gly Lys Thr Met Glu Asn Val Glu Glu Tyr Ser Tyr Lys Gln Glu
    130                 135                 140

Lys Lys Ile Arg Ala Ala Leu Arg Thr Thr Glu Arg Asp His Lys Lys
145                 150                 155                 160

Asn Val Gln Cys Ser Phe Met Leu Asp Ser Val Gly Gly Ser Leu Pro
                165                 170                 175

Lys Lys Ser Ile Pro Asp Val Asp Leu Asn Lys Pro Tyr Leu Ser Leu
            180                 185                 190

Gly Cys Ser Asn Ala Lys Leu Pro Val Ser Val Pro Met Pro Ile Pro
        195                 200                 205

Arg Thr Ala Arg Gln Thr Ser Arg Thr Asp Cys Pro Ala Asp Arg Leu
    210                 215                 220

Lys Phe Phe Glu Thr Leu Arg Leu Leu Leu Lys Leu Thr Ser Val Ser
225                 230                 235                 240

Lys Lys Lys Asp Arg Glu Thr Gly Glu Thr Lys Asn Thr Ser Ala Phe
                245                 250                 255

Trp Phe Asn Arg Ser Asn Glu Leu Ile Trp Leu Glu Leu Gln Ala Trp
            260                 265                 270

His Ala Gly Arg Thr Ile Asn Asp Gln Asp Leu Phe Leu Tyr Thr Ala
        275                 280                 285

Arg Gln Ala Ile Pro Asp Ile Ile Asn Glu Ile Leu Thr Phe Lys Val
    290                 295                 300

Asn Tyr Gly Ser Phe Ala Phe Val Arg Asn Gly Ala Ser Phe Asn Gly
305                 310                 315                 320

Thr Ser Val Glu Gly Gln Cys Arg Ala Pro His Gly Thr Lys Ile Val
                325                 330                 335
```

-continued

Cys Tyr Ser Thr Tyr His Glu His Leu Gln Arg Gln Arg Val Ser Phe
            340                 345                 350

Glu Gln Val Lys Arg Ile Met Glu Leu Leu Glu Tyr Met Glu Ala Leu
            355                 360                 365

Tyr Pro Ser Leu Gln Ala Leu Gln Lys Asp Tyr Glu Lys Tyr Ala Ala
        370                 375                 380

Lys Asp Phe Gln Asp Arg Val Gln Ala Leu Cys Leu Trp Leu Asn Ile
385                 390                 395                 400

Thr Lys Asp Leu Asn Gln Lys Leu Arg Ile Met Gly Thr Val Leu Gly
                405                 410                 415

Ile Lys Asn Leu Ser Asp Ile Gly Trp Pro Val Phe Glu Ile Pro Ser
            420                 425                 430

Pro Arg Ser Ser Lys Gly Asn Glu Pro Glu Asp Glu Gly Asp Asp Thr
        435                 440                 445

Glu Gly Asp Leu Lys Glu Leu Asp Ser Ser Thr Asp Glu Ser Glu Glu
    450                 455                 460

Glu Gln Leu Ser Gly Pro Arg Ala Pro Glu Pro Thr Gln Pro Ile Asp
465                 470                 475                 480

Thr Asn Phe Ser Ile His Ser Gln Asp Cys Val Leu Lys Lys Leu Glu
                485                 490                 495

Arg Leu Glu Ser Glu Asp Asp Ser Phe Gly Trp Gly Ala Pro Asp Cys
            500                 505                 510

Ser Thr Glu Ala Gly Phe Ser Arg His Cys Leu Thr Ser Ile Tyr Arg
        515                 520                 525

Pro Phe Val Asp Lys Ala Leu Lys Gln Met Gly Leu Arg Lys Leu Ile
    530                 535                 540

Leu Arg Leu His Lys Leu Met Asp Gly Ser Leu Gln Arg Ala Arg Ile
545                 550                 555                 560

Ala Leu Val Lys Ser Asp His Pro Val Glu Phe Ser Glu Phe Pro Asp
                565                 570                 575

Pro Met Trp Gly Ser Asp Tyr Val Gln Leu Ser Arg Thr Pro Pro Ser
            580                 585                 590

Ser Glu Gln Lys Gly Ser Thr Val Ser Trp Asp Glu Leu Lys Ser Met
        595                 600                 605

Asp Leu Pro Ser Phe Glu Pro Ala Phe Leu Val Leu Cys Arg Val Leu
    610                 615                 620

Leu Asn Val Ile His Glu Cys Leu Lys Leu Arg Leu Glu Gln Arg Pro
625                 630                 635                 640

Ala Gly Glu Pro Ser Leu Leu Ser Ile Lys Gln Leu Val Arg Glu Cys
                645                 650                 655

Lys Glu Val Leu Lys Gly Gly Leu Leu Met Lys Gln Tyr Tyr Gln Phe
            660                 665                 670

Met Leu His Glu Val Leu Ala Asp Leu Gln Lys Thr Asp Cys Asn Ile
        675                 680                 685

Asp Ala Phe Glu Glu Asp Leu His Lys Met Leu Met Val Tyr Phe Asp
    690                 695                 700

Tyr Met Arg Ser Trp Ile Gln Met Leu Gln Gln Leu Pro Gln Ala Ser
705                 710                 715                 720

His Ser Leu Lys Asn Leu Leu Glu Glu Glu Trp Asn Phe Thr Lys Glu
                725                 730                 735

Ile Thr His Tyr Ile Arg Gly Gly Glu Ala Gln Ala Gly Lys Leu Phe
            740                 745                 750

```
Cys Asp Ile Ala Gly Met Leu Leu Lys Ser Thr Gly Ser Phe Leu Glu
        755                 760                 765

Phe Gly Leu Gln Glu Ser Cys Ala Glu Phe Trp Thr Ser Ala Asp Asp
    770                 775                 780

Ser Asn Ala Ser Asp Glu Ile Arg Arg Ser Val Ile Glu Ile Ser Arg
785                 790                 795                 800

Ala Leu Lys Glu Leu Phe His Glu Ala Arg Glu Arg Ala Ser Lys Ala
                805                 810                 815

Leu Gly Phe Ala Lys Met Leu Arg Lys Asp Leu Glu Ile Ala Ala Glu
            820                 825                 830

Phe Ile Leu Ser Ala Pro Ile Arg Asp Leu Leu Asp Val Leu Lys Ser
        835                 840                 845

Lys Gln Tyr Val Lys Val Gln Ile Pro Gly Leu Glu Asn Leu Gln Val
    850                 855                 860

Phe Val Pro Asp Thr Leu Ala Glu Glu Lys Asn Ile Ile Leu Gln Leu
865                 870                 875                 880

Leu Asn Ala Ala Ala Gly Lys Asp Cys Ser Lys Glu Ser Asp Asp Val
                885                 890                 895

Leu Ile Asp Ala Tyr Leu Leu Leu Thr Lys Gln Ser Asp Arg Ala Arg
            900                 905                 910

Asp Ser Glu Asp Ser Trp Ala Ser Trp Glu Val Arg Pro Val Lys Ile
        915                 920                 925

Val Pro Gln Val Glu Thr Val Asp Thr Leu Arg Ser Met Gln Val Asp
    930                 935                 940

Asn Leu Leu Leu Val Val Met Gln Ser Ala His Leu Thr Ile Gln Arg
945                 950                 955                 960

Lys Ala Phe Gln Gln Ser Ile Glu Gly Leu Met Thr Leu Arg Gln Glu
                965                 970                 975

Gln Thr Ser Ser Gln Pro Val Ile Ala Arg Ala Leu Gln Gln Leu Lys
            980                 985                 990

Asn Asp Ala Leu Glu Leu Cys Asn Arg Ile Ser Asp Ala Ile Asp Arg
        995                 1000                1005

Val Asp His Met Phe Thr Ser Glu Phe Asp Ala Glu Val Asp Glu Ser
    1010                1015                1020

Glu Ser Val Thr Leu Gln Gln Tyr Tyr Arg Glu Ala Met Ile Gln Gly
1025                1030                1035                1040

Tyr Asn Phe Gly Phe Glu Tyr His Lys Glu Val Val Arg Leu Met Ser
                1045                1050                1055

Gly Glu Phe Arg Gln Lys Ile Gly Asp Lys Tyr Ile Ser Phe Ala Arg
            1060                1065                1070

Lys Trp Met Asn Tyr Val Leu Thr Lys Cys Glu Ser Gly Arg Gly Thr
        1075                1080                1085

Arg Pro Arg Trp Ala Thr Gln Gly Phe Asp Phe Leu Gln Ala Ile Glu
    1090                1095                1100

Pro Ala Phe Ile Ser Ala Leu Pro Glu Asp Asp Phe Leu Ser Leu Gln
1105                1110                1115                1120

Ala Leu Met Asn Glu Cys Ile Gly His Val Ile Gly Lys Pro His Ser
                1125                1130                1135

Pro Val Thr Gly Leu Tyr Leu Ala Ile His Arg Asn Ser Pro Arg Pro
            1140                1145                1150

Val Lys Val Pro Arg Cys His Ser Asp Pro Pro Asn Pro His Leu Ile
        1155                1160                1165

Ile Pro Thr Pro Glu Gly Phe Ser Thr Arg Ser Val Pro Ser Asp Ala
```

```
              1170                1175                1180
Arg Ser His Gly Ser Pro Ala Ala Pro Val Pro Ala Ala Ala
1185                1190                1195                1200

Thr Ala Gly Arg Pro Gly Pro Ala Gly Ser Asp Ser Ala Pro Pro Lys
                1205                1210                1215

Pro Ile Ser Ser Ala His Asp Thr Arg Gly Ser Ser Val Pro Glu Asn
                1220                1225                1230

Asp Arg Leu Ala Ser Ile Ala Ala Glu Leu Gln Phe Arg Ser Leu Ser
                1235                1240                1245

Arg His Ser Ser Pro Thr Glu Glu Arg Asp Glu Pro Ala Tyr Pro Lys
                1250                1255                1260

Gly Asp Ser Ser Gly Ser Ala Arg Arg Ser Trp Glu Leu Arg Thr Leu
1265                1270                1275                1280

Ile Ser Gln Thr Lys Asp Ser Ala Ser Lys Gly Pro Ile Glu Ala
                1285                1290                1295

Ile Gln Lys Ser Val Arg Leu Phe Glu Glu Lys Arg Tyr Arg Glu Met
                1300                1305                1310

Arg Arg Lys Asn Ile Ile Gly Gln Val Cys Asp Thr Pro Lys Ser Tyr
                1315                1320                1325

Asp Asn Val Met His Val Gly Leu Arg Lys Val Thr Phe Lys Trp Gln
                1330                1335                1340

Arg Gly Asn Lys Ile Gly Glu Gly Gln Tyr Gly Lys Val Tyr Thr Cys
1345                1350                1355                1360

Ile Ser Val Asp Thr Gly Glu Leu Met Ala Met Lys Glu Ile Arg Phe
                1365                1370                1375

Gln Pro Asn Asp His Lys Thr Ile Lys Glu Thr Ala Asp Glu Leu Lys
                1380                1385                1390

Ile Phe Glu Gly Ile Lys His Pro Asn Leu Val Arg Tyr Phe Gly Val
                1395                1400                1405

Glu Leu His Arg Glu Glu Met Tyr Ile Phe Met Glu Tyr Cys Asp Glu
                1410                1415                1420

Gly Thr Leu Glu Glu Val Ser Arg Leu Gly Leu Gln Glu His Val Ile
1425                1430                1435                1440

Arg Leu Tyr Ser Lys Gln Ile Thr Ile Ala Ile Asn Val Leu His Glu
                1445                1450                1455

His Gly Ile Val His Arg Asp Ile Lys Gly Ala Asn Ile Phe Leu Thr
                1460                1465                1470

Ser Ser Gly Leu Ile Lys Leu Gly Asp Phe Gly Cys Ser Val Lys Leu
                1475                1480                1485

Lys Asn Asn Ala Gln Thr Met Pro Gly Glu Val Asn Ser Thr Leu Gly
                1490                1495                1500

Thr Ala Ala Tyr Met Ala Pro Glu Val Ile Thr Arg Ala Lys Gly Glu
1505                1510                1515                1520

Gly His Gly Arg Ala Ala Asp Ile Trp Ser Leu Gly Cys Val Val Ile
                1525                1530                1535

Glu Met Val Thr Gly Lys Arg Pro Trp His Glu Tyr Glu His Asn Phe
                1540                1545                1550

Gln Ile Met Tyr Lys Val Gly Met Gly His Lys Pro Pro Ile Pro Glu
                1555                1560                1565

Arg Leu Ser Pro Glu Gly Lys Asp Phe Leu Ser His Cys Leu Glu Ser
                1570                1575                1580

Glu Pro Arg Met Arg Trp Thr Ala Ser Gln Leu Leu Asp His Ser Phe
1585                1590                1595                1600
```

Val Lys Val Cys Thr Asp Glu Glu
              1605

<210> SEQ ID NO 12
<211> LENGTH: 5442
<212> TYPE: DNA
<213> ORGANISM: Canis lupus familiaris

<400> SEQUENCE: 12

| | | | | | |
|---|---|---|---|---|---|
| atggggggtt | tcctcggcgc | cggcacctcg | gggggagtcc | cgggggggcct | cctcccccc | 60 |
| ccgcgcgcgg | tgcgcgccgc | ccgccggccg | gccattgttc | cggatcctgc | tgggattttt | 120 |
| gagctggtgg | aagtggttgg | aaatggcacc | tacggacaag | tctataaggg | tcgacatgtt | 180 |
| aaaacaggtc | agctggcggc | catcaaagtt | atggatgtca | ctgaggatga | agaggaagaa | 240 |
| atcaaactgg | agataaatat | gctgaagaaa | tattctcatc | atagaaatat | tgcaacatat | 300 |
| tatggtgctt | tcattaaaaa | gagccctcca | ggacatgatg | accaactctg | gcttgttatg | 360 |
| gagttctgtg | gggctgggtc | cattacagac | cttgtgaaga | acaccaaagg | gaacacgctc | 420 |
| aaggaagact | ggatagctta | catctccaga | gaaatcctga | ggggactggc | acatcttcac | 480 |
| atccatcacg | tgattcaccg | agacatcaag | ggccagaatg | tgttgctgac | cgagaatgca | 540 |
| gaggtgaagc | ttgttgattt | cggcgtgagt | gctcagcttg | accggaccgt | tgggaggaga | 600 |
| aatacgttca | taggcacccc | ctactggatg | gctcctgagg | ttattgcctg | tgatgagaac | 660 |
| ccagatgcca | cctatgatta | cagaagtgat | ctttggtctt | gtggcatcac | agccattgag | 720 |
| atggcagaag | gtgctccccc | tctctgtgac | atgcatccaa | tgagagcact | gtttctcatt | 780 |
| cccagaaacc | ctcctcccag | gctgaagtca | aaaaaatggt | caaagaaatt | ttttagtttt | 840 |
| atagaagggt | gcctggtgaa | gaattacatg | cagcgaccct | ccacagagca | gcttttgaaa | 900 |
| catcctttta | agggatca | gccaaacgaa | aggcaagtta | gaatccagct | taaggaccat | 960 |
| atagaccgga | ccagaaagaa | gagaggagag | aagagtgaaaa | ccgaatatga | gtacagtggg | 1020 |
| agtgaggaag | aagaggagga | agtgcctgaa | caggaaggag | agccaagctc | cattgtcaat | 1080 |
| gtgcctggtg | agtcgacact | tcgtcgggat | tcttgagac | tgcagcagga | gaacaaggaa | 1140 |
| cgttctgagg | ctcttcggag | gcagcagcta | ctgcaggagc | agcagctccg | ggagcaggaa | 1200 |
| gagtataaga | ggcagctact | ggcagagagg | cagaaacgca | tcgagcagca | gaaagaacag | 1260 |
| aggcggcgac | tagaagagca | acaaaggaga | gagcgggaag | ctagaaggca | acaagaacgt | 1320 |
| gaacagcgaa | ggagagaaca | agaagagaag | aggcgtctgg | aggaactgga | gagaagacgt | 1380 |
| aaagaggaag | aagagaggag | gcgggcagag | gaagaaaaga | ggagagttga | aagagaacag | 1440 |
| gagtatatca | ggcgacagct | agaagaggag | cagcggcact | tggaaatcct | tcagcagcag | 1500 |
| ctgctccagg | agcaggccat | gttactgcat | gaccacagga | ggccgcaccc | gcagcagccg | 1560 |
| ccgccaccgc | agcaggaaag | gagcaagcca | agctatcacg | ctccggagcc | taagccccac | 1620 |
| tatgagcctg | ctgacagagc | tcgagaggtg | gaagatagat | ttaggaaaac | taaccacagc | 1680 |
| tcccctgaag | cccagtctaa | gcagacaggc | agagtattgg | aaccaccagt | gccttccaga | 1740 |
| tcagagtctt | tttccaatgg | caactccgag | tctgtgcatc | ctgccctgca | gagaccagct | 1800 |
| gagccacagg | ttcctgtgag | gacaacgtct | cgttcccctg | ttctgtcccg | tcgggattcc | 1860 |
| ccactgcaag | gcagtggaca | gcaaaatagt | caagcaggtc | aaagaaactc | cactagcagt | 1920 |
| attgagcccc | ggctgctgtg | ggagagagtg | gagaagctgg | tgcccaggcc | tggcagtggc | 1980 |
| agctcctccg | gatccagcaa | ctccggatcc | cagcctgggt | cccaccctgg | gtcccagagt | 2040 |

```
ggctctggag agcgcttcag agtgagatca tcatccaaat ctgaaggctc tccttctcag    2100
cgcctagaaa atgcagtgaa aaaacctgaa gaaaagaaag aagttttcag acctctcaag    2160
cctgccgatt tgactgcact ggccaaagag cttcgagcag tggaagatgt gcgaccacca    2220
cacaaagtga cagactactc ctcatccagt gaggagtccg ggacaacaga tgaggaagac    2280
gatgatgtag aacaagaagg ggctgaggaa gccacctctg gaccagagga caccagagca    2340
gcgtcgtccc tgaatttgag caatggtgaa acagaatccg tgaaaaccat gattgttcat    2400
gacgacgtag aaagtgaacc agccatgacc ccatccaagg agggcactct aatcgtccgc    2460
cagagtacag ttgaccaaaa gcgcgccagc catcatgaga gcaatggctt tgccggtcgc    2520
attcacctct tgccagatct cttacagcaa agccattcct cctccacttc ctccacctcc    2580
tcctccccat cctccagcca gccgacaccc accatgtccc cacagacacc ccaggacaag    2640
ctcactacta atgagactca gtccgctagt agcacactcc agaaacacaa atcttcctcc    2700
tcctttacac cttttataga ccccagatta ctacagattt ctccatctag tgggacaaca    2760
gtgacttctg tggtgggatt ttcctgtgat ggaatgagac cagaagccat aaggcaagat    2820
cctacccgga agggctcagt ggtcaatgtg aatcccacca cactaggcc acagagtgat    2880 accccggaga ttcgtaaata taagaagaga tttaactccg agattctgtg tgctgcctta    2940
tggggagtga atttgctagt gggtacagag agtggcctga tgctgctgga cagaagtggc    3000
caagggaagg tatatcccct gatcaaccga agacgatttc agcaaatgga tgtccttgaa    3060
ggcttgaatg tcttggtgac aatatctggc aaaaaggata agttacgtgt ctactatttg    3120
tcctggttaa gaaataaaat acttcacaat gatccagaag ttgagaagaa gcagggatgg    3180
acgactgtgg gagatttgga aggatgtgta cactataaag ttgtaaaata tgaaagaatc    3240
aaatttctgg taattgcttt gaagagttct gtggaggtct atgcgtgggc acccaagcca    3300
tatcacaaat ttatggcctt taagtcattt gggggaattag tacataagcc attgctggtg    3360
gatctcactg tggaggaagg ccagaggttg aaagtgatct atggatcctg tgctggattc    3420
catgctgttg atgtggattc tggatcagtc tatgacattt atctaccaac acacatccag    3480
tgtagcatca aaccccatgc aatcatcatc ctccccaaca cagatggcat ggagcttctg    3540
gtgtgctatg aagatgaagg ggtttatgtg aatacttatg gaagaatcac caaggatgtg    3600
gttctgcagt ggggagagat gccaacatct gtagcatata ttcgatccaa ccagacgatg    3660
ggctggggag aaaaggccat agagatccga tctgtggaaa ctggtcattt ggatggtgtg    3720
tttatgcaca aaagggctca agactaaaa ttcctatgtg aacgcaatga caaggtcttc    3780
tttgcctctg ttcggtctgg tggcagcagc caggtttatt tcatgacgtt aggcaggact    3840
tctcttctga gctggtaaaa gtggtggaat gaggcttgct ggcccccccag agtcttcaag    3900 atcctgagaa cttggaattc cttgcaactg gagctcagag ctgcaccgat gtagtccagg    3960
acagctgtgt gtgcagacac cgtgtgtggg gtgttttgtt ttgttttgtt ttgtttcctt    4020
tctgcacctc ttacagttta tccccttct tttctttcc ctactcaaaa ataaatcaag    4080
gctgcaatgc agctggtgct gttcatattc taccatcagg tgctataagt gtttgggatt    4140
gagcattaga ccagaaagca aatgcctttc cttcagctcc agaattcctt gtctctgagt    4200
gactctgtct tatgggtatt gaaggtggag accatgaaca tgccattggt tttgttggaa    4260
atgggcacac ggaggtgtaa aatggtgctc taatgagcag cttactgaag cagagagcag    4320
atttaatata gtaacattaa cagtgtattt aattgacatt tctttttgt aatgtgacaa    4380
```

```
tatgtggtca aagaagaagg tgcaggttta agaagttaat atttataaaa tgtgaaagac    4440
acagttacta ggataacttt tttgtgggtg gggccttggg aggcagggtg gggtgggtta    4500
aggggagggt cccatttgt ttatttggat tttttttttt ttttttttt ttggcttgg     4560 ccaaaaactc agtcattttt ctgtgtacca ggttttgcct aaatcatgtg caaatggttc    4620
ttttaaaaaa aaaaaaaaaa aagaaaaaga aatgtgtgc atttgtataa cggccagaac    4680
tttgttgtgt gacagtatta gcactgcctc agtaaaggt ttaatttttg tttaaaccta    4740
gaagtgcgac aacagtttta cccacagtct gcacttgcag aggaaaagaa attttttcaa    4800
ccacatgttt attttttgc ctacctcatt gtttgtaatg cattaagagg tggtttagtt     4860
tatatgtttt tggaggaaaa attaatgttt aatttaatct taataccaaa actatcagat    4920
tgaagtttga ctgttatttt gtcacaggtc tcagtaggca caagagaaat taccccctgaa   4980 gataggaaat agccatatgg cttcatcatg ctgacagatg caatctgttt tctaagttca    5040
gagagcagaa tgcttcgttt tcaccagatt taccattagt ggttgatggg caactatggc    5100
ctacaacata agaggcctca ttgttctcaa tttgggttt ggtagcagac gggtggtcat     5160
attagaatag tcacacaaac tgttcagtgt tgcaggaact ttttcttggg gtgggggagg    5220
ggtgatgttt ccctttcta aaaatgcaat gcactaaaac tatttaaga atgtagttaa      5280 tactgcttat tcataagatg gcatcttcct gtgttttagg tgtaatatca aagccctggc    5340
ttttctcctc tcacttgctc tcttgttctc tctctgttt ttaaaccaat tttactttat     5400
gaatatgttc atgacatttg taataaatgt cttgggtaat aa                      5442
```

<210> SEQ ID NO 13
<211> LENGTH: 20
<212> TYPE: DNA
<213> ORGANISM: Artificial Sequence
<220> FEATURE:
<223> OTHER INFORMATION: Map4k4 antisense oligonucleotide

<400> SEQUENCE: 13
cttctccact ctctcccaca                                              20

<210> SEQ ID NO 14
<211> LENGTH: 21
<212> TYPE: DNA
<213> ORGANISM: Artificial Sequence
<220> FEATURE:
<223> OTHER INFORMATION: Map4k4 antisense oligonucleotide

<400> SEQUENCE: 14
cctcttcttc ctcactccca c                                            21

<210> SEQ ID NO 15
<211> LENGTH: 19
<212> TYPE: DNA
<213> ORGANISM: Artificial Sequence
<220> FEATURE:
<223> OTHER INFORMATION: Map4k4 antisense oligonucleotide

<400> SEQUENCE: 15
cttctccact ctctcccac                                               19

<210> SEQ ID NO 16
<211> LENGTH: 20
<212> TYPE: DNA
<213> ORGANISM: Artificial Sequence
<220> FEATURE:
<223> OTHER INFORMATION: Map4k4 antisense oligonucleotide

```
<400> SEQUENCE: 16
gcttctccac tctctcccac                                              20

<210> SEQ ID NO 17
<211> LENGTH: 21
<212> TYPE: DNA
<213> ORGANISM: Artificial Sequence
<220> FEATURE:
<223> OTHER INFORMATION: Map4k4 antisense oligonucleotide

<400> SEQUENCE: 17
gcttctccac tctctcccac a                                            21

<210> SEQ ID NO 18
<211> LENGTH: 20
<212> TYPE: DNA
<213> ORGANISM: Artificial Sequence
<220> FEATURE:
<223> OTHER INFORMATION: Map4k4 siRNA

<400> SEQUENCE: 18
tgctgtctgg tgaagaatta                                              20

<210> SEQ ID NO 19
<211> LENGTH: 21
<212> TYPE: DNA
<213> ORGANISM: Artificial Sequence
<220> FEATURE:
<223> OTHER INFORMATION: Map4k4 siRNA

<400> SEQUENCE: 19
gaccaactct ggcttgttat t                                            21

<210> SEQ ID NO 20
<211> LENGTH: 19
<212> TYPE: DNA
<213> ORGANISM: Artificial Sequence
<220> FEATURE:
<223> OTHER INFORMATION: Map4k4 siRNA

<400> SEQUENCE: 20
cagaagtggc caagggaaa                                               19

<210> SEQ ID NO 21
<211> LENGTH: 19
<212> TYPE: DNA
<213> ORGANISM: Artificial Sequence
<220> FEATURE:
<223> OTHER INFORMATION: Map4k4 siRNA

<400> SEQUENCE: 21
agaagaaggt gcaggttta                                               19

<210> SEQ ID NO 22
<211> LENGTH: 19
<212> TYPE: DNA
<213> ORGANISM: Artificial Sequence
<220> FEATURE:
<223> OTHER INFORMATION: Map4k4 siRNA

<400> SEQUENCE: 22
agagaaggca atagagata                                               19

<210> SEQ ID NO 23
```

```
<211> LENGTH: 19
<212> TYPE: DNA
<213> ORGANISM: Artificial Sequence
<220> FEATURE:
<223> OTHER INFORMATION: Map4k4 siRNA

<400> SEQUENCE: 23
gcttacatct ccagggaaa                                                 19

<210> SEQ ID NO 24
<211> LENGTH: 21
<212> TYPE: DNA
<213> ORGANISM: Artificial Sequence
<220> FEATURE:
<223> OTHER INFORMATION: Control siRNA

<400> SEQUENCE: 24
cagtcgcgtt tgcgactggt t                                              21
```

UNITED STATES PATENT AND TRADEMARK OFFICE
CERTIFICATE OF CORRECTION

PATENT NO.         : 9,434,951 B2
APPLICATION NO.    : 14/401629
DATED              : September 6, 2016
INVENTOR(S)        : Michael P. Czech and Rachel Roth Flach Page 1 of 1

It is certified that error appears in the above-identified patent and that said Letters Patent is hereby corrected as shown below:

In the Claims

Claim 3
Column 109, line 50, delete "vessel," and insert -- vessel --.

Signed and Sealed this
Twentieth Day of December, 2016

Michelle K. Lee
*Director of the United States Patent and Trademark Office*